United States Patent
Platenburg et al.

(10) Patent No.: US 9,139,828 B2
(45) Date of Patent: *Sep. 22, 2015

(54) METHOD FOR EFFICIENT EXON (44) SKIPPING IN DUCHENNE MUSCULAR DYSTROPHY AND ASSOCIATED MEANS

(75) Inventors: Gerard Johannes Platenburg, Voorschoten (NL); Josephus Johannes de Kimpe, Utrecht (NL); Judith Christina Theodora van Deutekom, Dordrecht (NL); Garrit-Jan Boudewijn van Ommen, Amsterdam (NL); Annemieke Aartsma-Rus, BE Hoofddorp (NL)

(73) Assignees: Prosensa Technologies B.V., Leiden (NL); Academisch Ziekenhuis Leiden, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/992,218

(22) Filed: Nov. 11, 2010

(65) Prior Publication Data

US 2012/0059042 A1 Mar. 8, 2012

Related U.S. Application Data

(63) Continuation of application No. PCT/NL2009/050258, filed on May 14, 2009.

(60) Provisional application No. 61/128,010, filed on May 15, 2008.

(30) Foreign Application Priority Data

May 14, 2008 (EP) ..................... 08156193

(51) Int. Cl.
*C12N 15/11* (2006.01)
*C07H 21/04* (2006.01)
*C12N 15/113* (2010.01)
*A61K 48/00* (2006.01)

(52) U.S. Cl.
CPC .............. *C12N 15/113* (2013.01); *A61K 48/00* (2013.01); *C12N 2310/11* (2013.01); *C12N 2310/111* (2013.01); *C12N 2310/315* (2013.01); *C12N 2310/321* (2013.01); *C12N 2310/346* (2013.01); *C12N 2310/3517* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 5,034,506 A | 7/1991 | Summerton et al. | |
| 5,418,139 A | 5/1995 | Campbell | |
| 5,541,308 A | 7/1996 | Hogan et al. | |
| 5,593,974 A | 1/1997 | Rosenberg et al. | |
| 5,608,046 A | 3/1997 | Cook et al. | |
| 5,627,263 A | 5/1997 | Ruoslahti et al. | |
| 5,658,764 A | 8/1997 | Pergolizzi et al. | |
| 5,741,645 A | 4/1998 | Orr et al. | |
| 5,766,847 A | 6/1998 | Jackle et al. | |
| 5,853,995 A | 12/1998 | Lee | |
| 5,869,252 A | 2/1999 | Bouma et al. | 435/6 |
| 5,916,808 A | 6/1999 | Kole et al. | 435/375 |
| 5,962,332 A | 10/1999 | Singer et al. | 436/94 |
| 5,968,909 A | 10/1999 | Agrawal et al. | |
| 5,976,879 A | 11/1999 | Kole et al. | 435/375 |
| 6,124,100 A | 9/2000 | Jin | |
| 6,130,207 A | 10/2000 | Dean et al. | |
| 6,133,031 A | 10/2000 | Monia et al. | |
| 6,172,208 B1 | 1/2001 | Cook | 536/23.1 |
| 6,172,216 B1 | 1/2001 | Bennett et al. | |
| 6,210,892 B1 | 4/2001 | Bennett et al. | 435/6 |
| 6,251,589 B1 | 6/2001 | Tsuji et al. | |
| 6,280,938 B1 | 8/2001 | Ranum et al. | |
| 6,300,060 B1 | 10/2001 | Kantoff et al. | |
| 6,322,978 B1 | 11/2001 | Kahn et al. | |
| 6,329,501 B1 | 12/2001 | Smith et al. | |
| 6,355,481 B1 | 3/2002 | Li et al. | |
| 6,355,690 B1 | 3/2002 | Tsuji | |
| 6,369,038 B1 | 4/2002 | Blumenfeld et al. | |
| 6,379,698 B1 | 4/2002 | Leamon | |
| 6,399,575 B1 | 6/2002 | Smith et al. | |
| 6,514,755 B1 | 2/2003 | Ranum et al. | |
| 6,623,927 B1 | 9/2003 | Brahmachari et al. | |
| 6,653,466 B2 | 11/2003 | Matsuo | |
| 6,653,467 B1 | 11/2003 | Matsuo et al. | |
| 6,670,461 B1 | 12/2003 | Wengel et al. | |
| 6,727,355 B2 | 4/2004 | Matsuo et al. | 536/24.5 |
| 6,794,192 B2 | 9/2004 | Parums et al. | |

(Continued)

FOREIGN PATENT DOCUMENTS

| | | |
|---|---|---|
| CA | 2319149 | 10/2001 |
| CA | 2526893 | 11/2004 |

(Continued)

OTHER PUBLICATIONS

GenBank accession No. AZ993191.1, 2M0278E12F mouse 10kb plasmid UUGC2M library *Mus muscu* genomic clone UUGC2M0278E12F, genomic survey sequence, entry created and last updated on Apr. 27, 2001.*

(Continued)

*Primary Examiner* — Dana Shin

(74) *Attorney, Agent, or Firm* — Sunstein Kann Murphy & Timbers LLP

(57) ABSTRACT

The invention relates to oligonucleotides that bind to and induce skipping of exon 44 in the human dystrophin pre-mRNA, and methods of use.

15 Claims, 3 Drawing Sheets

(56) References Cited

U.S. PATENT DOCUMENTS

Figure 2A:
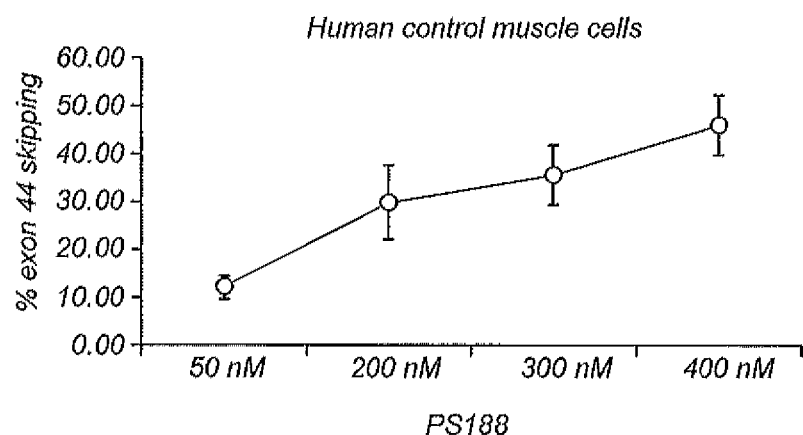

| | | | |
|---|---|---|---|
| 6,902,896 B2 | 6/2005 | Ranum et al. | |
| 6,982,150 B2 | 1/2006 | Sheetz et al. | |
| 7,001,994 B2 | 2/2006 | Zhu | 536/4.1 |
| 7,034,009 B2 * | 4/2006 | Pavco et al. | 514/44 R |
| 7,118,893 B2 | 10/2006 | Ranum et al. | |
| 7,189,530 B2 | 3/2007 | Botstein et al. | |
| 7,202,210 B2 | 4/2007 | Wolfman et al. | |
| 7,250,404 B2 | 7/2007 | Felgner et al. | |
| 7,355,018 B2 | 4/2008 | Glass | |
| 7,405,193 B2 | 7/2008 | Lodish et al. | 514/2 |
| 7,442,782 B2 | 10/2008 | Ranum et al. | 536/23.1 |
| 7,514,551 B2 | 4/2009 | Rabbani et al. | 536/26.6 |
| 7,534,879 B2 | 5/2009 | van Deutekom | 536/24.5 |
| 7,589,189 B2 | 9/2009 | Ichiro et al. | 536/24.5 |
| 7,655,785 B1 * | 2/2010 | Bentwich | 536/24.1 |
| 7,771,727 B2 | 8/2010 | Fuselier et al. | 424/185.1 |
| 7,807,816 B2 | 10/2010 | Wilton et al. | 536/24.5 |
| 7,902,160 B2 | 3/2011 | Matsuo et al. | 514/44 |
| 7,960,541 B2 | 6/2011 | Wilton et al. | 536/24.5 |
| 8,232,384 B2 | 7/2012 | Wilton et al. | 536/24.5 |
| 8,324,371 B2 | 12/2012 | Popplewell et al. | 536/24.5 |
| 8,450,474 B2 | 5/2013 | Wilton et al. | 536/24.5 |
| 8,455,634 B2 | 6/2013 | Wilton et al. | 536/24.5 |
| 8,455,635 B2 | 6/2013 | Wilton et al. | 536/24.5 |
| 8,455,636 B2 | 6/2013 | Wilton et al. | 536/24.5 |
| 8,476,423 B2 | 7/2013 | Wilton et al. | 536/24.5 |
| 8,486,907 B2 | 7/2013 | Wilton et al. | 514/44 |
| 8,524,880 B2 | 9/2013 | Wilton et al. | 536/24.5 |
| 8,637,483 B2 | 1/2014 | Wilton et al. | 514/44 A |
| 2001/0056077 A1 | 12/2001 | Matsuo | |
| 2002/0049173 A1 | 4/2002 | Bennett et al. | |
| 2002/0055481 A1 | 5/2002 | Matsuo et al. | |
| 2002/0115824 A1 | 8/2002 | Engler et al. | |
| 2002/0165150 A1 | 11/2002 | Ben-Sasson | |
| 2003/0073215 A1 | 4/2003 | Baker et al. | |
| 2003/0082763 A1 | 5/2003 | Baker et al. | |
| 2003/0082766 A1 | 5/2003 | Baker et al. | |
| 2003/0109476 A1 | 6/2003 | Kmiec et al. | |
| 2003/0124523 A1 | 7/2003 | Asselbergs et al. | |
| 2003/0134790 A1 | 7/2003 | Langenfeld | |
| 2003/0235845 A1 | 12/2003 | van Ommen et al. | |
| 2003/0236214 A1 | 12/2003 | Wolff et al. | |
| 2004/0101852 A1 | 5/2004 | Bennett et al. | |
| 2004/0132684 A1 | 7/2004 | Sampath et al. | |
| 2004/0226056 A1 | 11/2004 | Roch et al. | |
| 2005/0096284 A1 | 5/2005 | McSwiggen | |
| 2005/0222009 A1 | 10/2005 | Lamensdorf et al. | |
| 2005/0246794 A1 * | 11/2005 | Khvorova et al. | 800/286 |
| 2005/0277133 A1 | 12/2005 | McSwiggen | |
| 2006/0074034 A1 | 4/2006 | Collins et al. | |
| 2006/0148740 A1 | 7/2006 | Platenburg | |
| 2007/0021360 A1 | 1/2007 | Nyce et al. | 514/44 |
| 2007/0082861 A1 | 4/2007 | Matsuo et al. | |
| 2007/0141628 A1 | 6/2007 | Cunningham et al. | 435/7.1 |
| 2007/0275914 A1 | 11/2007 | Manoharan et al. | |
| 2007/0292408 A1 | 12/2007 | Singh et al. | |
| 2008/0015158 A1 | 1/2008 | Ichiro et al. | |
| 2008/0039418 A1 | 2/2008 | Freier | |
| 2008/0113351 A1 | 5/2008 | Naito et al. | 435/6 |
| 2008/0200409 A1 | 8/2008 | Wilton et al. | 514/44 |
| 2008/0207538 A1 | 8/2008 | Lawrence et al. | 514/41 |
| 2008/0249294 A1 | 10/2008 | Haeberli et al. | 536/24.5 |
| 2009/0092981 A1 | 4/2009 | Swayze et al. | 435/6 |
| 2010/0081627 A1 | 4/2010 | Sampath et al. | 514/27 |
| 2010/0099750 A1 | 4/2010 | McSwiggen et al. | 514/44 R |
| 2010/0130591 A1 | 5/2010 | Sazani et al. | 514/44 A |
| 2010/0168212 A1 * | 7/2010 | Popplewell et al. | 514/44 R |
| 2010/0248239 A1 | 9/2010 | Highsmith, Jr. et al. | 435/6 |
| 2011/0015253 A1 | 1/2011 | Wilton et al. | 514/44 A |
| 2011/0015258 A1 | 1/2011 | Wilton et al. | 514/44 R |
| 2011/0046203 A1 | 2/2011 | Wilton et al. | 514/44 A |
| 2011/0166081 A1 | 7/2011 | Campbell et al. | 514/20.9 |
| 2011/0263682 A1 | 10/2011 | De Kimpe et al. | 514/44 A |
| 2011/0263686 A1 | 10/2011 | Wilton et al. | 514/44 A |
| 2011/0294753 A1 * | 12/2011 | De Kimpe et al. | 514/40 |
| 2012/0022144 A1 | 1/2012 | Wilton et al. | 514/44 A |
| 2012/0022145 A1 | 1/2012 | Wilton et al. | 514/44 A |
| 2012/0029057 A1 | 2/2012 | Wilton et al. | 514/44 A |
| 2012/0029058 A1 | 2/2012 | Wilton et al. | 514/44 A |
| 2012/0029059 A1 | 2/2012 | Wilton et al. | 514/44 A |
| 2012/0029060 A1 | 2/2012 | Wilton et al. | 514/44 A |
| 2012/0041050 A1 | 2/2012 | Wilton et al. | 514/44 A |
| 2012/0046348 A1 | 2/2012 | Vaillant et al. | 514/44 R |
| 2012/0108652 A1 | 5/2012 | Popplewell et al. | 514/44 A |
| 2013/0116310 A1 | 5/2013 | Wilton et al. | 514/44 A |
| 2013/0217755 A1 | 8/2013 | Wilton et al. | 514/44 A |
| 2013/0253033 A1 | 9/2013 | Wilton et al. | 514/44 A |
| 2013/0253180 A1 | 9/2013 | Wilton et al. | 536/24.5 |
| 2013/0274313 A1 | 10/2013 | Wilton et al. | 514/44 A |
| 2013/0331438 A1 | 12/2013 | Wilton et al. | 514/44 A |

FOREIGN PATENT DOCUMENTS

| | | | |
|---|---|---|---|
| EP | 558697 | 9/1993 | |
| EP | 614977 A2 | 9/1994 | |
| EP | 850300 | 7/1998 | |
| EP | 1054058 | 5/2000 | |
| EP | 1015628 A1 | 7/2000 | |
| EP | 1133993 | 9/2001 | |
| EP | 1160318 | 12/2001 | |
| EP | 1191097 | 3/2002 | |
| EP | 1191098 | 3/2002 | |
| EP | 1380644 | 1/2004 | |
| EP | 1 487 493 A2 | 12/2004 | |
| EP | 1495769 | 1/2005 | |
| EP | 1501931 | 2/2005 | |
| EP | 1544297 | 6/2005 | |
| EP | 1567667 A1 | 8/2005 | |
| EP | 1568769 | 8/2005 | |
| EP | 1 619 249 A1 | 1/2006 | C12N 15/11 |
| EP | 1619249 | 1/2006 | |
| EP | 1857548 | 11/2007 | |
| EP | 2 119 783 A1 | 11/2009 | C12N 15/11 |
| EP | 2 135 948 A2 | 12/2009 | C12N 15/11 |
| KR | 20030035047 | 5/2003 | |
| WO | WO-9301286 A2 | 1/1993 | |
| WO | WO-9516718 A1 | 6/1995 | |
| WO | WO-9530774 | 11/1995 | |
| WO | WO-9712899 | 4/1997 | |
| WO | WO-9730067 | 8/1997 | |
| WO | WO-9818920 A1 | 5/1998 | |
| WO | WO-9849345 A1 | 11/1998 | |
| WO | WO 98/53804 A1 | 12/1998 | A61K 31/00 |
| WO | WO 00/24885 A2 | 5/2000 | C12N 15/11 |
| WO | WO-0179283 A1 | 10/2001 | |
| WO | WO 01/83503 | 11/2001 | C07H 21/00 |
| WO | WO 01/83503 A2 | 11/2001 | C07H 21/00 |
| WO | WO-0183695 | 11/2001 | |
| WO | WO-0202406 | 1/2002 | |
| WO | WO-0224906 | 3/2002 | |
| WO | WO-0226812 A1 | 4/2002 | |
| WO | WO-0229056 | 4/2002 | |
| WO | WO-03002739 | 1/2003 | |
| WO | WO-03/014145 A2 | 2/2003 | |
| WO | WO-03013437 | 2/2003 | |
| WO | WO-03037172 | 5/2003 | |
| WO | WO-03095647 | 11/2003 | |
| WO | WO-2004/011060 A2 | 2/2004 | |
| WO | WO-2004015106 | 2/2004 | |
| WO | WO-2004016787 | 2/2004 | |
| WO | WO 2004/037854 A1 | 5/2004 | C07K 1/04 |
| WO | WO-2004048570 | 6/2004 | |
| WO | WO-2004083432 | 9/2004 | |
| WO | WO-2004083446 | 9/2004 | |
| WO | WO-2004101787 | 11/2004 | |
| WO | WO-2004108157 | 12/2004 | |
| WO | WO 2005/023836 A2 | 3/2005 | |
| WO | WO-2005019453 A2 | 3/2005 | |
| WO | WO-2005035550 | 3/2005 | |
| WO | WO-2005085476 A1 | 9/2005 | |
| WO | WO-2005086768 | 9/2005 | |
| WO | WO-2005105995 A2 | 11/2005 | |
| WO | WO 2005/115479 A2 | 12/2005 | A61K 48/00 |
| WO | WO-2005115439 | 12/2005 | |

(56) References Cited

FOREIGN PATENT DOCUMENTS

| | | | |
|---|---|---|---|
| WO | WO-2005116204 A1 | 12/2005 | |
| WO | 2006/000057 A1 | 1/2006 | |
| WO | WO-2006007910 | 1/2006 | |
| WO | WO-2006017522 | 2/2006 | |
| WO | WO-2006031267 | 3/2006 | |
| WO | WO-2006031267 A2 | 3/2006 | |
| WO | WO-2006/054262 A2 | 5/2006 | |
| WO | WO-2006083800 | 8/2006 | |
| WO | WO-2006108052 | 10/2006 | |
| WO | WO-2006112705 | 10/2006 | |
| WO | WO-2006121960 A2 | 11/2006 | |
| WO | WO 2007/004979 A1 | 1/2007 | A61K 38/00 |
| WO | WO-2007002904 A2 | 1/2007 | |
| WO | WO-2007044362 | 4/2007 | |
| WO | WO-2007089584 | 8/2007 | |
| WO | WO-2007089611 A2 | 8/2007 | |
| WO | 2007/135105 A1 | 11/2007 | |
| WO | WO-2007123402 | 11/2007 | |
| WO | WO-2008011170 A2 | 1/2008 | |
| WO | WO-2008018795 | 2/2008 | |
| WO | WO-2008021136 A2 | 2/2008 | |
| WO | WO 2008/039418 A2 | 4/2008 | A61K 31/454 |
| WO | WO 2008/043561 | 4/2008 | A61K 48/00 |
| WO | WO 2008/043561 A2 | 4/2008 | A61K 48/00 |
| WO | WO 2008/103060 A1 | 8/2008 | C12N 15/11 |
| WO | WO 2009/005793 A2 | 1/2009 | A61K 48/00 |
| WO | WO 2009/008727 A2 | 1/2009 | A61K 47/48 |
| WO | WO 2009/015384 A1 | 1/2009 | A61K 38/00 |
| WO | 2009/054725 A2 | 4/2009 | |
| WO | WO 2009/099326 A1 | 8/2009 | A61K 48/00 |
| WO | WO 2009/101399 A1 | 8/2009 | A61K 31/712 |
| WO | WO 2009/120887 A2 | 10/2009 | A61K 47/48 |
| WO | WO 2009/135322 A1 | 11/2009 | C12Q 1/68 |
| WO | WO 2009/139630 A2 | 11/2009 | C12N 15/11 |
| WO | WO 2009/144481 A2 | 12/2009 | |
| WO | WO 2009/151600 A2 | 12/2009 | C12N 15/12 |
| WO | WO 2010/044894 A1 | 4/2010 | C07K 19/00 |
| WO | WO 2010/048586 A1 | 4/2010 | C12N 15/113 |
| WO | WO 2010/050802 A2 | 5/2010 | A61K 31/7105 |
| WO | WO 2010/110835 A1 | 9/2010 | C12Q 1/68 |
| WO | WO 2010/115993 A1 | 10/2010 | C12N 15/113 |
| WO | WO 2010/123369 A1 | 10/2010 | C12N 15/113 |
| WO | WO 2011/032045 A1 | 3/2011 | C07H 21/04 |
| WO | WO 2011/057350 A1 | 5/2011 | C12N 15/113 |
| WO | WO 2011/097641 A1 | 8/2011 | C07H 21/04 |

OTHER PUBLICATIONS

GenBank accession No. EW162121.1, rfat0126_k17.y1 fat *Sus scrofa* cDNA5-, mRNA sequence, entry created on Aug. 13, 2007, last updated on Mar. 3, 2011.*

Wilton et al., "Antisense Oligonucleotide-induced Exon Skipping Across the Human Dystrophin Gene Transcript", Molecular Therapy: The Journal of the American Society of Gene Therapy, vol. 15, No. 7, 1288-1296, Jul. 2007.

Aartsma-rus et al., "Targeted exon skipping as a potential gene correction therapy for Duchenne muscular dystrophy", Neuromuscular Disorders 12 (2002) S71-S77.

Aartsma-rus et al., "Functional Analysis of 114 Exon-Internal AONs for Targeted DMD Exon Skipping: Induction for Steric Hindrance of SR Protein Binding Sites", Oligonucleotides 15: 284-297 (2005).

Aartsma-rus et al.,"Therapeutic antisense-induced exon skipping in cultured muscle cells from six different DMD pateints", Human Molecular Genetics, 2003, vol. 12, No. 8, 907-914.

van Deutekom et al.,"Advance in Duchenne Muscular Dystrophy gene therapy", Nature Reviews Genetics, vol. 4, Oct. 2003, 774-783.

van Ommen et al., "The therapeutic potential of antisense-mediated exon skipping", Current Opinion in Molecular Therapeutics 2008, 10(2); 140-149.

Aartsma-Rus et al. "Antisense Mediated exon skipping; A Versatile Tool with Therapeutic and Research Applications" *RNA* 2007 pp. 1609-1624 vol. 13 No. 10.

Aartsma-Rus et al. Antisense-Induced Exon Skipping for Duplications in Duchenne Muscular Dystrophy Jul. 5, 2007 BMC Med. Genet. 8:43.

Aartsma-Rus et al. Therapeutic Modulation of DMD splicing by Blocking Exonic Splicing Enhancer Sites with Antisense Oligonucleotides Ann NY Acad Sci 2006 pp. 74-76 vol. 1082.

Aartsma-Rus, et al., Antisense-Induced Multiexon Skipping for Duchenne Muscular Dystrophy Makes More Sense, Am. J. Hum. Genet, 2004 pp. 83-92, vol. 74.

Aartsma-Rus, et al., Exploring the Frontiers of Therapeutic Exon Skipping for Duchenne Muscular Dystrophy by Double Targeting within One or Multiple Exons, Molecular Therapy, 2006, pp. 1-7.

Abbs et al., A convenient multiplex PCR system for the detection of dystrophin gene deletions: a comparative analysis with cDNA hybridisation shows mistypings by both methods, J. Med. Genet, 1991, pp. 304-311, vol. 28.

Agrawal and Kandimalla, et al., "Antisense therapeutics: is it as simple as complementary base recognition?" Mol. Med. Today, Feb. 2000, vol. 6., pp. 72-81.

Anderson et al., Correlated NOS-I[mu] and myf5 expression by satellite cells in mdx mouse muscle regeneration during NOS manipulation and deflazacort treatment. Neuromusccular Disorders, Jun. 2003, vol. 13(5): 388-396.

Arechavala-Gomeza et al., . "Comparative Analysis of Antisense Oligonucleotide Sequences for Targeted Skipping of Exon 51 During Dystrophin pre-mRNA Splicing in Human Muscle" *Hum Gene Ther* 2007 pp. 798-810 vol. 18 No. 9.

Arruda V R, The role of immunosuppression in gene and cell based treatments for Duchenne Muscular Dystrophy. Molecular Therapy, Jun. 2007, vol. 15(6): 1040-1041.

Arzumanov, et al. Inhibition of HIV-1 Tat-dependent trans activation by steric block chimeric 2'-O-methyl/LNA oligoribonucleotides. Biochemistry, 2001, vol. 40, pp. 14645-14654.

Austin et al. "Cloning and characterization of alternatively spliced isoforms of Dp71." *Hum Mol Genetics* 1995 vol. 4 No. 9 1475-1483.

Austin, et al., "Expression and synthesis of alternatively spliced variants of Dp71 in adult human brain." *Neuromuscular Disorders*. 10(2000) 187-193.

Australian Office Action for AU 2009240879, dated Jun. 22, 2011.

Barabino et al. (1992) "Antisense probes targeted to an internal domain in US snRNP specifically inhibit the second step of pre-mRNA splicing" Nucleic Acids Res. 20(17):4457-4464.

Bionity.Com NEWS-Center, Leiden University Medical Center and Prosensa B.V. Announce First Successful Clinical Study with RNA-based Therapeutic PRO051, dated Jan. 3, 2008, <http://www.bionity.com/news/e/76185>.

Biopharmaceutiques, Merging Pharma & Biotech, Edition 48, Jan. 10, 2008. <http://www.biopharmaceutiques.com/en/num>, visited Jan. 11, 2008.

Bremmer-Bout, et al., Targeted exon skipping in transgenic hDMD mice: A model for direct preclinical screening of human-specific antisense oligonucleotides. Mol Ther. Aug. 2004; 10(2):232-40.

Brett et al., EST comparison indicates 38% of human m RNAs contain possible alternative splice forms. FEBS Lett 474(1): 83-86.

Brown, et al., "Structure and mutation of the dystrophin gene" in Dystrophin: Gene, protein and cell biology, (Brown and Lucy, eds). Cambridge University Press, Cambridge, 1997, pp. 1-16.

Burnett, et al., "DNA sequence-specific polyamides alleviate transcription inhibition associated with long GAA. TTC repeats in Friedreich's ataxia," *PNAS*, 2006, pp. 11497-11502, vol. 103, No. 31.

Canadian Office Action for CA 2,524,255, dated Jul. 6, 2011.

Caplen, et al., "Rescue of polyglutamine-mediated cytotoxicity by double-stranded RNA-mediated RNA interference," *Human molecular genetics*, 2002, pp. 175-184, vol. 11, No. 2.

Cartegni, et al., Abstract, Listening to silence and understanding nonsense: exonic mutations that affect splicing, Nature Reviews Genetics, Apr. 2002, pp. 285-298, vol. 3.

Chaubourt et al., Muscular nitric oxide synthase ([mu]NOS) and utrophin. J. of Physiology Paris, Jan.-Mar. 2002; vol. 96(1-2): 43-52.

Coulter et al. Identification of a new class of exonic splicing enhancers by in vivo selection. Mol. Cell. Biol. 17(4) 2143-50 (1997).

Crooke. in Basic Principles of Antisense Therapeutics, Springer-Verlag, Eds, New York, 1998, pp. 1-50.

Dahlqvist, et al., "Functional notch signaling is required for BMP4-induced inhibition of myogenic differentiation," Development 130:6089-6099 (2003).

(56) References Cited

OTHER PUBLICATIONS

De Angelis, et al., Chimeric snRNA molecules carrying antisense sequences against the splice junctions of exon 51 of the dystrophin pre-mRNA exon skipping and restoration of a dystrophin synthesis in delta 48-50 DMD cells, PNAS, Jul. 9, 2002, pp. 9456-9461, vol. 99, No. 14.
Declaration of Dr. Adrian Krainer (submitted in Third Party's Stmt for JP Appl. No. 2002-529499, dated Oct. 29, 2010).
Dickson, et al., Screening for antisense modulation of dystrophin pre-mRNA splicing, Neuromuscul. Disord., 2002, S67-70, Suppl. 1.
Dirkson, et al., Mapping the SF2/ASF Binding Sites in the Bovine Growth Hormone Exonic Splicing Enhancer, The Journal of Biological Chemistry, Sep. 15, 2000, pp. 29170-29177, vol. 275, No. 37.
Dunckley, et al., Modification of splicing in the Dsytrophin gene in cultured Mdx muscle cells by antisense oligoribonucleotides. Hum Mol Genet. 1995 7(7):1083-90.
Dunckley, et al., Modulation of Splicing in the DMD Gene by Antisense Oligoribonucleotides, Nucleosides & Nucleotides, 1997, pp. 1665-1668, vol. 16, No. 7-9.
Erba et al., Structure, chromosome location, and expression of the human gamma-actin gene: differential evolution, location, and expression of the cytoskeletal beta- and gamma-actin genes. Mol. Cell. Biology, 1988, 8(4):1775-89.
Errington, et al., Target selection for antisense oligonucleotide induced exon skipping in the dystrophin gene. J Gene Med. Jun. 2003; 5(6):518-27.
European Patent Office Action dated Jan. 29, 2007.
Feener et al., Alternative splicing of human dystrophin mRNA generates isoforms at the carboxy terminus. Nature, 338 (6215): 509-511 (1989).
Fluiter, K., "In Vivo tumor growth inhibition and biodistribution studies of locked nucleic acid (LNA) antisense oligonucleotides," Nucl. Acids Research 2003, vol. 31., No. 3., pp. 953-962.
Fu, et al., "An Unstable Triplet Repeat in a Gene Related to Myotonic Muscular Dystrophy", *Science*, vol. 255, 1256-1258. 1992.
Furling. et al., "Viral vector producing antisense RNA restores myotonic dystrophy myoblast functions", *Gene Therapy* (2003) 10, 795-802.
Galderisi, et al., "Myotonic dystrophy: antisense oligonucleotide inhibition of DMPK gene expression in vitro." *Biochem Biophys Res Commun* 221:750-754 (1996).
Genes VII, Jan. 2000, Benjamin Lewin, Chapter 22, Nuclear Splicing, pp. 704-705.
Ginjaar, et al., Dystrophin nonsense mutation induces different levels of exon 29 skipping and leads to variable phenotypes within one BMD family, European Journal of Human Genetics (2000) 8, 793-796.
Grady, "Early drug test shows promise in treating muscular dystrophy" International Herald Tribune, Jan. 3, 2008, Health & Science, p. 9.
Grady, Promising Dystrophy Drug Clears Early Test, The New York Times, Dec. 27, 2007.
Granchelli et al., Pre-clinical screening of drugs using the mdx mouse. Neuromuscular Disorders, Pergamon Pres. vol. 10(4-5): 235-239, Jun. 2000.
Gryaznov, "Oligonucleotide N3'—> P5' phosphoramidates as potential therapeutic agents." Biochemistry et Biophys. Acta, 1999, vol. 1489, pp. 131-140/.
Hagiwara, et al. "A novel point mutation (G-1 to T) in a 5' splice donor site of intron 13 of the dystrophin gene results in exon skipping and is responsible for Becker muscular dystrophy." Am J. Hum Genet. Jan. 1994;54(1):53-61.
Handa, et al., "The AUUCU repeats responsible for spinocerebellar ataxia type 10 form unusual RNA hairpins." *Journal of Biological Chemistry* 280(32):29340-29345 (2005).
Hansen, "Product Development—Addition by subtraction." BioCentury, The Bernstein Report on BioBusiness, Jan. 7, 2008, p. A28 of 38.

Hasholt, et al., "Antisense downregulation of mutant huntingtin in a cell model," *Journal of Gene Medicine*, 2003, pp. 528-538, vol. 5, No. 6.
Hoffman, et al. ,"Somatic reversion/suppression of the mouse mdx phenotype in vivo." *J. of the Neurological Sciences*, 1990, 99: 9-25.
Hoffman, Skipping toward Personalized Molecular Medicine, N. England J. Med., Dec. 27, 2007, pp. 2719-2722, vol. 357, No. 26.
Hope for muscular dystrophy drug, The Daily Telegraph, Dec. 28, 2007.
Hussey, et al., Analysis of five Duchenne muscular dystrophy exons and gender determination using conventional duplex polymerase chain reaction on single cells, Molecular Human Reproduction, 1999, pp. 1089-1094, vol. 5, No. 11.
Iezzi, et al. "Deacetylase inhibitors increase muscle cell size by promoting myoblast recruitment and fusion through induction of follistation," Development Cell 6:673-684 (2004).
International Preliminary Examination Report, International Application No. PCT/NL01/00697, dated Aug. 1, 2002.
International Search Report, International Application No. PCT/NL 2008/050470, dated Jul. 2, 2009.
International Search Report, International Application No. PCT/NL 2008/050475, dated Jun. 25, 2009.
International Search Report, International Application No. PCT/NL 2008/050673, dated Feb. 9, 2009.
International Search Report, International Application No. PCT/NL01/00697, dated Dec. 21, 2002.
International Search Report, International Application No. PCT/NL2004/000196, dated Oct. 28, 2004.
International Search Report, International Application No. PCT/NL2006/000209, dated Oct. 5, 2006.
Karras, et al., Deletion of Individual Exons and Induction of Soluble Murine Interleukin-5 Receptor-alpha Chain Expression through Antisense Oligonucleotide-Mediated Redirection of Pre-mRNA Splicing, Molecular Pharmacology, 2000, pp. 380-387, vol. 58.
Kerr, et al., "BMP Regulates Skeletal Myogenesis at Two Steps," Molecular Cellular Proteomics 2.9:976. 123.8 (2003) (Abstract Only).
Kurrek, et al., "Design of antisense oligonucleotides stabilized by locked nucleic acids." Nucleic Acids Research, 2002, vol. 30, No. 9, pp. 1911-1918.
Langlois, et al., "Hammerhead ribozyme-mediated destruction of nuclear foci in myotonic dystrophy myoblasts," *Molecular therapy*, 2003, pp. 670-680, vol. 7, No. 5.
Laptev et al., (1994) "Specific inhibition of expression of a human collagen gene (COL1A1) with modified antisense oligonucleotides. The most effective target sites are clustered in double-stranded regions of the predicted secondary structure for the mRNA" Biochemistry 33(36):11033-11039.
Lee et al., "Receptor mediated uptake of peptides that bind the human transferrin receptor", Eur. J. Biochem. 268, 2004-2012 (2001).
Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.
Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided).
Letter from Prosensa Therapeutics B.V. To Federal Agency for Medicines and Health Products dated Jan. 9, 2008, regarding a Phase I/II, open label, escalating dose, pilot study to assess the effect, safety, tolerability and pharmacokinetics of multiple subcutaneous doses of PRO051 in patients with Duchenne muscular dystrophy.
Liu et al., "A mechanism for exon skipping caused by nonsense or missense mutations in BRCA1 and other genes." Nat Genet. Jan. 2001;27(1):55-8.
Liu, et al., "Specific inhibition of Huntington's disease gene expression by siRNAs in cultured cells", *Proc. Japan Acad.* 79, Ser. B (2003), 293-298.

(56) References Cited

OTHER PUBLICATIONS

Liu, et al., Identification of functional exonic splicing enhancer motifs recognized by individual SR proteins, Genes & Development, 1998, pp. 1998-2012, vol. 12.
Lu et al. Functional Amounts of Dystrophin Produced by Skipping the Mutated Exon in the MDX Dystrophic Mouse 2003 Nat Med 8: 1009-1014.
Lu, et al., Massive Idiosyncratic Exon Skipping Corrects the Nonsense Mutation in Dystrophic Mouse Muscle and Produces Functional Revertant Fibers by Clonal Expansion, The Journal Cell Biology, Mar. 6, 2000, pp. 985-995, vol. 148, No. 5.
LUMC and Prosensa report positive results of DMD study, Pharmaceutical Business Review Online, dated Dec. 28, 2007, <http://www.pharmaceutical-business-review.com/article_news_print.asp?guid=8462FD44-F35D-4EOB-BC>.
Mann, et al., Antisense-induced exon skipping and synthesis of dystrophin in the mdx mouse. Proc Natl Acad Sci USA Jan. 2, 2001: 98(1):42-7.
Mann, et al., Improved antisense oligonucleotide induced exon skipping in the mdx mouse model of muscular dystrophy. J Gene Med. Nov.-Dec. 2002:4(6):644-54.
Matsuo et al. (1992) "Partial deletion of a dystrophin gene leads to exon skipping and to loss of an intra-exon hairpin structure from the predicted mRNA precursor" Biochem. Biophys. Res. Commun. 182(2):495-500.
Matsuo, et al., "Duchenne/Becker muscular dystrophy: from molecular diagnosis to gene therapy." Brain Dev. (1996) 18(3):167-172.
Matsuo, et al., Exon Skipping during Splicing of Dystrophin mRNA Precursor due to an Intraexon Deletion in the Dystrophin Gene of Duchenne Muscular Dystrophe Kobe. *J. Clin. Invest.* 87, 2127-2131.
McClorey et al. Induced Dystrophin Exon Skipping in Human Muscle Explants Neuromuscul Disord 2006 pp. 583-590 vol. 16 No. 9-10.
Monaco, et al., An Explanation for the Phenotypic Differences between Patients Bearing Partial Deletions of the DMD Locus, Genomics, 1988, pp. 90-95, vol. 2.
Moon, et. al., "Target site Search and effective inhibition of leukaemic cell growth by a covalently closed multiple anti-sense oligonucleotide to c-myb" The Biochemical Journal, Mar. 1, 2000, vol. 346 Pt 2, pp. 295-303.
Munroe (1988) "Antisense RNA inhibits splicing of pre-mRNA in vitro" EMBO J. 7(8):2523-2532.
Muntoni et al. "A Mutation in the Dystrophin Gene Selectively Affecting Dystrophin Expression in the Heart." *J. Clin Invest.* vol. 96 Aug. 1995. 693-699.
Muntoni, et al., 149th ENMC International Workshop and 1st TREAT-NMD Workshop on: "Planning Phase I/II Clinical trials using Systemically Delivered Antisense Oligonucleotides in Duchenne Muscular Dystrophy," Neuromuscular Disorders, 2008, pp. 268-275, vol. 18.
New Clinical Trial Results Show How Personalized Medicine Will Alter Treatment of Genetic Disorders, Medical News Today, Dec. 29, 2007 <http://www.medicalnewstoday.com/article/92777.php>.
Nishio, et al., Identification of a novel first exon in the human dystrophin gene and of a new promoter located more than 500 kb upstream of the nearest known promoter. (1994) J. Clin. Invest. 94:1037-1042.
Notice of Opposition filed against EP 1 619 249 B, dated Jun. 23, 2009.
Office Action for U.S. Appl. No. 10/395,031, dated Apr. 2, 2009.
Office Action for U.S. Appl. No. 10/395,031, dated Aug. 23, 2007.
Office Action for U.S. Appl. No. 10/395,031, dated Feb. 6, 2006.
Office Action for U.S. Appl. No. 10/395,031, dated Jul. 8, 2005.
Office Action for U.S. Appl. No. 10/395,031, dated May 30, 2008.
Office Action for U.S. Appl. No. 10/395,031, dated Nov. 30, 2006.
Office Action for U.S. Appl. No. 10/395,031, dated Oct. 16, 2009.
Office Action for U.S. Appl. No. 11/233,495, dated Dec. 1, 2008.
Office Action for U.S. Appl. No. 11/233,495, dated Jun. 25, 2009.
Office Action for U.S. Appl. No. 11/233,507, dated Jun. 15, 2007.
Office Action for U.S. Appl. No. 11/233,507, dated Mar. 19, 2008.
Office Action for U.S. Appl. No. 11/233,507, dated May 29, 2009.
Office Action for U.S. Appl. No. 11/233,507, dated Nov. 12, 2008.
Office Action for U.S. Appl. No. 11/982,285, dated May 4, 2009.
Office Action for U.S. Appl. No. 11/982,285, dated Sep. 18, 2009.
Opalinska and Gewirtz. "Nucleic-acid therapeutics: basic principles and recent applications." Nature Reviews Drug Discovery, 2002, vol. 1, pp. 503-514.
Oxford Dictionary of English, 2nd Edition, Revised, Oxford University Press, p. 158.
Patel, et al., "The Function of Myostatin and strategies of Myostatin blockade-new hope for therapies aimed at promoting growth of skeletal muscle," Neuromuscular Disorders 15(2):117-126 (2005).
Patentee's response during prosecution of opposed patent, dated Jan. 27, 2010.
Pramono, et al., Abstract, Induction of Exon Skipping of the Dystrophin Transcript in Lymphoblastoid Cells by Transfecting an Antisense Oligodeoxynucleotide Complementary to an Exon Recognition Sequence, Biochemical and Biophysical Research Communications, Sep. 13, 1996, pp. 445-449, vol. 226, No. 2.
Radley et al., Duchenne muscular dystrophy: Focus on pharmaceutical and nutritional interventions. International J. of Biochem. and Cell Biol., vol. 39(3):469-477, Oct. 2006.
Rando, Thomas A., "Oligonucleotide-mediated gene therapy for muscular dystrophies." Neuromuscular Disorders, 2002, vol. 12, pp. S55-S60.
Request for an Opinion under Section 74(A) in relation to Patent No. EP (UK) 1 619 249B in the name of Academisch Ziekenhuis Leiden, opinion issued on Jun. 4, 2009.
Request for UK IPO Opinion (Section 74A & Rule 93)—EP(UK) 1619249 dated Mar. 9, 2009.
Roberts et al., Direct detection of dystrophin gene rearrangements by analysis of dystrophin mRNA in peripheral blood lymphocytes. Am. J. Hum. Genet. 49(2): 298-310 (1991).
Roberts, et al., "Exon structure of the human dystrophin gene." Genomics, 1993, vol. 16, No. 2, pp. 536-538. (1993).
Roberts, et al., Direct diagnosis of carriers of Duchenne and Becker muscular dystrophy by amplification of lymphocyte RNA. Lancet, 336 (8730-8731): 1523-6 (1990).
Roberts, et al., Searching for the 1 in 2,400,000: a review of dystrophin gene point mutations. Hum. Mut. 4:1-11 (1994).
Rolland et al., Overactivity of exercise-sensitive cation channels and their impaired modulation by IGF-1 in mdx native muscle fibers: beneficial effect of pentoxifylline. Dec. 2006; Epub Sep. 28, Neurobiology Disease, vol. 24(3): 466-474.
Scanlon, "Anti-genes: siRNA, ribozymes, and antisense." Curr. Pharmaceutical Biotechnology, 2004, vol. 5, pp. 415-420.
Segalat et al., Capon expression in skeletal muscle is regulated by position, repair, NOS activity, and dystrophy. Experimental Cell Research, Jan. 2005, vol. 302(2): 170-179.
Sertic, et al., "Deletion screening of the Duchenne/Becker muscular dystrophy gene in Croatian population" Coll. Antropol. 1997, 1:151-156.
Shapiro and Senapathy, "RNA splice junctions of different classes of eukaryotes: sequence statistics and functional implications in gene expression." Nucleic Acids Research, 1987, vol. 15. No. 17, pp. 7155-7174.
Sherratt, et al., Exon Skipping and Translation in Patients with Frameshift Deletions in the Dystrophin Gene, Am. J. Hum. Genet, 1993, pp. 1007-1015, vol. 53.
Shiga, et al., Disruption of the Splicing Enhancer Sequence within Exon 27 of the Dystrophin Gene by a Nonsense Mutation Induces Partial Skipping of the Exon and Is Responsible for Becker Muscular Dystrophy, J. Clin. Invest., Nov. 1997, pp. 2204-2210, vol. 100, No. 9.
Simoes-Wust, et al., bcl-xL Antisense Treatment Induces Apoptosis in Breast Carcinoma Cells, Int. J. Cancer, 2000, pp. 582-590, vol. 87.
Sterrenburg, et al., "Gene expression of profiling highlights defective myogenesis in DMD patients and a possible role for bone morphogenetic protein 4," Neurobiology of Disease 23(1):228-236 (2006).
Surono et al. Chimeric RNA/ethylene-Bridged Nucleic Acids Promote Dystrophin Expression in Myocytes of Duchenne Muscular

(56) References Cited

OTHER PUBLICATIONS

Dystrophy by Inducing Skipping of the Nonsense Mutation-Encoding Exon Hum Gene Ther. vol. 15(8) pp. 749-757 (2004).
Surono et al. "Six Novel Transcripts that Remove a Huge Intron Ranging from 250 to 800 kb Are Produced by Alternative Splicing of the 5' Region of the Dystrophin Gene in Human Skeletal Muscle." *BBRC* 239 895-899 (1997).
Suter, et al., Double-target antisense U7 snRNAs promote efficient skipping of an aberrant exon in three human B-thalassemic mutations, Human Molecular Genetics, 1999, pp. 2415-2423, vol. 8, No. 13.
Suwanmanee et al. (2002) "Restoration of Human b-globin Gene Expression in Murine and Human IVS2-654 Thalassemic Erythroid Cells by Free Uptake of Antisense Oligonucleotides" Mol. Pharmacology 62(3):545-553.
Takashima et al. Oligonucleotides Against a Splicing Enhancer Sequence Led to Dystrophin Production in Muscle Cells From a Duchenne Muscular Dystrophy Patient Brain Dev Dec. 2001; 23:788-90.
Takeshima, et al., Modulation of In Vitro Splicing of the Upstream Intron by Modifying an Intra-Exon Sequence Which is Deleted from the Dystrophin Gene in Dystrophin Kobe, J. Clin. Invest., Feb. 1995, pp. 515-520, vol. 95.
Tanaka, et al., Polypurine Sequences within a Downstream Exon Function as a Splicing Enhanced, Molecular and Cellular Biology, Feb. 1994, pp. 1347-1354, vol. 14, No. 2.
Thanh, et al., "Characterization of revertant muscle fibers in Duchenne muscular dystrophy, using exon-specific monoclonal antibodies against dystrophin." Am. J. Hum. Genet. 1995, vol. 56, pp. 725-731.
Third Party's Statement for Japan Appl. No. 2002-529499, dated Oct. 29, 2010.
Tian H, Kole R, "Selection of novel exon recognition elements from a pool of random sequences." Mol Cell Biot 15(11):6291-8. (1995).
TREAT-NMD Neuromuscular Network, Jan. 11, 2008.
Tsuchida "Peptides, Proteins & Antisense: the role of myostatin and bone morphogenetic proteins in muscular disorders," Expert Opinion of Biologica Therapy 6(2):147-153 (2006).
Van Deutekom, et al., Antisense-induced exon skipping restores dystrophin expression in DMD patient derived muscle cells. Hum Mol Genet. Jul. 15, 2001:10(15:1547-54).
Van Deutekom, et al., Local Dystrophin Restoration with Antisense Oligonucleotide PRO051, N. England J. Med., Dec. 27, 2007, pp. 2677-2686.
Verreault, et al. "GENE silencing in the development of personalized cancer treatment: the targets, the agents and the delivery systems." Curr. Gene Therapy, 2006, vol. 6, pp. 505-553.
Vickers, et al., "Efficient reduction of target RNAs by small interfering RNA and RNase H-dependent antisense agents. A comparative analysis." *J. Biol. Chem.* 278(9):7108-7118 (2003).
Watakabe, et al., The role of exon sequences in splice site selection, Genes & Development, 1993, pp. 407-418, vol. 7.
Wells et al. Enhanced in Vivo Delivery of Antisense Oligonucleotide to Restore Dystrophin Expression in Adult MDX Mouse Muscle FEBS Letters 2003 552: 145-149.
Wheway and Roberts. "The Dystrophin Lymphocyte promoter revisited: 4.5-megabase intron, or artefact?" *Neuromuscular Disorders* 13(2003) 17-20.
Wilton, et al., "Specific removal of the nonsense mutation from the mdx dystrophin protein mRNA using antisense oligonucleotides." Neuromuscular Disorders, 1999, vol. 9, pp. 330-338.
Wilton, et al., "Antisense oligonucleotides, exon skipping and the dystrophin gene transcript," Acta Myologica XXIV:222-229 (2005).
Yen, et al., "Sequence-specific cleavage of Huntingtin MRNA by catalytic DNA," *Animals of Neurology*, 1999, pp. 366-373, vol. 46, No. 3.
Zhou et al., Current understanding of dystrophin-related muscular dystrophy and therapeutic challenges ahead. Chinese Medical J., Aug. 2006, vol. 119(16): 1381-1391.

International Search Report, International Application No. PCT/NL2009/050006, dated Jul. 31, 2009.
International Search Report, International Application No. PCT/NL2009/050113, dated Jun. 30, 2010.
Aartsma-Rus et al. "Theoretic Applicability of Antisense-Mediated Exon Skipping for Duchenne Muscular Dystrophy" Human Mutation 2009 pp. 293-299 vol. 30 No. 3.
Alter et al., "Systemic delivery of morpholino oligonucleotide restores dystrophin expression bodywide and improves dystrophic pathology." Nature Medicine. Feb. 2006;12(2):175-7. Epub Jan. 29, 2006.
Barany "The ligase chain reaction in a PCR world." PCR Methods Appl. Aug. 1991;1(1):5-16.
Buck et al., "Design Strategies and Performance of Custom DNA Sequencing Primers" Biotechniques. 27:528-536, 1999.
Denny et al., "Oligo-riboprobes. Tools for in situ hybridisation". Histochemistry (1988) 89:481-493.
Duboc et al., "Effect of Perindopril on the Onset and Progression of Left Ventricular Dysfunction in Duchenne Muscular Dystrophy." *Journal of Amer. Coll. Cardiology*, 45(6):855-7, Mar. 15, 2005.
GenBank accession No. AZ993191.1, 2MO278E12F mouse 10kb plasmid UUGC2M library *Mus muscu* genomic clone UUGC2MO278E12F, genomic survey sequence, entry created and last updated on Apr. 27, 2001.
Heemskerk et al. 2009 Development of Antisense-Mediated Exon Skipping as a Treatment for Duchenne Muscular Dystrophy Ann NY Acad Sci vol. 1175 pp. 71-79.
Heemskerk et al. 2010 Preclinical PK and PD Studies on 2' O-methylphosphorothioate RNA antisense Oligonucleotides in the MDX Mouse Model Mol. Ther vol. 18(6) pp. 1210-1217.
Ikezawa et al. "Dystrophin gene analysis on 130 patients with Duchenne Muscular dystrophy with a special reference to muscle mRNA analysis." Brain & Develop. 20:165-168, 1998.
International Preliminary Report on Patentability and Written Opinion for PCT/EP2007/054842, mailed on Nov. 21, 2008, 8 pages.
International Search Report for PCT/EP2007/054842, mailed on Aug. 21, 2007, 3 pages.
International Search Report for PCT/NL2009/050006 dated Jul. 31, 2009.
International Search Report for PCT/NL2009/050113 dated Jun. 30, 2010.
International Search Report, PCT/NL2006/000209, Oct. 5, 2006.
Ito, et al., "Purine-Rich Exon Sequences Are Not Necessarily Splicing Enhancer Sequence in the Dystrophin Gene." *Kobe J. Med. Sci.* 47, 193/202, Oct. 2001.
Kinali et al. 2009 Local Restoration of Dystrophin Expression With the Morpholino Oligomer AVI-4658 in Duchenne Muscular Dystrophy: A Single-blind, Placebo-Controlled Dose-Escalation, Proof-of Concept Study. Lancet Neurol. vol. 8(10) pp. 918-928.
Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutan.
Nakamura et al. 2009 Exon Skipping Therapy for Duchenne Muscular Dystrophy Neuropathology vol. 29(4) pp. 494-501.
O'Shaughnessy et al., "Superior Survival With Capecitabine Plus Docetaxel Combination Therapy in Anthracycline-Pretreated Patients With Advanced Breast Cancer: Phase III Trial Results." *Journal of Clinical Oncology*, vol. 20, No. 12 (Jun. 15), 2002: pp. 2812-2823.
Politano et al., "Gentamicin administration in Duchenne patients with Premature stop codon. Preliminary results." Acta Myologica 22:15-21, 2003.
Popplewell et al. 2009 Design of Phosphorodiamidate Morpholino Oligomers (PMOs) for the Induction of Exon Skipping of the Human DMD Gene Mol. Ther vol. 17(3) pp. 554-561.
Reitter B. "Deflazacort vs. prednisone in Duchenne muscular dystrophy: trends of an ongoing study." Brain Dev. 1995;17 Suppl:39-43.
Rosen et al., "Combination Chemotherapy and Radiation Therapy in the Treatment of Metastatic Osteogenic Sarcoma." *Cancer* 35: 622-630, 1975.

(56) References Cited

OTHER PUBLICATIONS

Smith et al., "Muscle-specific peptide #5", Mar. 23, 1999. From http://www.ebi.ac.uk/cgi-bin/epo/epofetch?AAW89659, downloaded Jul. 16, 2007. XP 002442550.

Spitali et al. 2009 Exon skipping mediated dystrophin reading frame restoration for small mutations Hum Mut vol. 30(11) pp. 1527-1534.

Takeshima et al "Intravenous Infusion of an Antisense Oligonucleotide Results in Exon Skipping in Muscle Dystrophin mRNA of Duchenne Muscular Dystrophy." Pediatric Research. May 2006, 59, 5, p. 690-694.

Van Vliet, et al., "Assessment of the feasibility of exon 45-55 multiexon skipping for duchenne muscular dystrophy." BMC Medical Genetics, Dec. 2008, vol. 9:105 (7 pages).

Verhaart et al., "Prednisolone treatment does not interfere with 2'-O-methyl phosphorothioate antisense-mediated exon skipping in Duchenne muscular dystrophy." *Hum Gene Ther.* Mar. 2012;23(3):262-73. Epub Jan. 26, 2012.

Wang et al. "Adeno-associated virus vector carrying human minidystrophin genes effectively ameliorates muscular dystrophy in mdx mouse model", Dec. 5, 2000, P.N.A.S. 97(25):13714-13719.

Yokota, et al., Efficacy of Systemic Morpholino Exon-Skipping in Duchenne Dystrophy Dogs, Ann Neurol., 2009, pp. 667-676, vol. 65.

Aartsma-Rus et al., "Comparative analysis of antisense oligonucleotide analogs for targeted DMD exon 46 skipping in muscle cells," *Gene Ther.*, vol. 11, No. 18, pp. 1391-1398 (Jul. 2004).

Arap et al., "Steps toward mapping the human vasculature by phage display," *Nat. Med*, vol. 8, No. 2, pp. 121-127 (Feb. 2002).

Bijvoet et al., "Recombinant human acid α-glucosidase: high level production in mouse milk, biochemical characteristics, correction of enzyme deficiency in GSDII KO mice," *Hum. Mol. Genet.*, vol. 7, No. 11, pp. 1815-1824 (Oct. 1998).

Brown et al., "Gene delivery with synthetic (non viral) carriers," *Int. J. Pharm.*, vol. 229, Nos. 1-2, pp. 1-21 (Oct. 2001) [Abstract].

El-Andaloussi et al., "Induction of splice correction by cell-penetrating peptide nucleic acids," *J. Gene Med.*, vol. 8, No. 10, pp. 1262-1273 (Oct. 2006) [Abstract].

Garcia-Blanco et al., "Alternative splicing in disease and therapy," *Nat. Biotechnol.*, vol. 22, No. 5, pp. 535-546 (May 2004).

Ghosh et al., "Mannose 6-phosphate receptors: new twists in the tale," *Nat. Rev. Mol. Cell Biol.*, vol. 4, No. 3, pp. 202-212 (Mar. 2003).

Gollins et al., "High-efficiency plasmid gene transfer into dystrophic muscle," *Gene Ther,*, vol. 10, No. 6, pp. 504-512 (Mar. 2003).

Hassan, "Keys to the Hidden Treasures of the Mannose 6-Phosphate/Insulin-Like Growth Factor 2 Receptor," *Am. J. Path.*, vol. 162, No. 1, pp. 3-6 (Jan. 2003).

Lu et al., "Systemic delivery of antisense oligoribonucleotide restores dystrophin expression in body-wide skeletal muscles," *Proc. Natl. Acad. Sci. U.S.A.*, vol. 102, No. 1, pp. 198-203 (Jan. 2005).

Lu et al., "Non-viral gene delivery in skeletal muscle: a protein factory," *Gene Ther.*, vol. 10, No. 2, pp. 131-142 (Jan. 2003).

Martiniuk et al., "Correction of glycogen storage disease type II by enzyme replacement with a recombinant human acid maltase produced by over-expression in a CHO-DHFR(neg) cell line," *Biochem. Biophys. Res. Commun.*, vol. 276, No. 3, pp. 917-923 (Oct. 2000) [Abstract].

Reuser et al., "Uptake and Stability of Human and Bovine Acid α-Glucosidase in Cultured Fibroblasts and Skeletal Muscle Cells from Glycogenosis Type II Patients," *Exp. Cell Res.*, vol. 155, No. 1, pp. 178-189 (Nov. 1984).

Samoylova et al., "Elucidation of muscle-binding peptides by phage display screening," *Muscle Nerve*, vol. 22, No. 4, pp. 460-466 (Apr. 1999).

Varani et al., "The G•U wobble base pair: A fundamental building block of RNA structure crucial to RNA function in diverse biological systems," *EMBO Rep.*, vol. 1, No. 1, pp. 18-23 (Jul. 2000).

Weisbart et al., "Cell type specific targeted intracellular delivery into muscle of a monoclonal antibody that binds myosin llb.," *Mol. Immunol.*, vol. 39, No. 13, pp. 783-789 (Mar. 2003) [Abstract].

Wenk et al., "Quantitation of Mr 46000 and Mr 300000 mannose 6-phosphate receptors in human cells and tissues.," *Biochem. Int.*, vol. 23, No. 4, pp. 723-731 (Mar. 1991) [Abstract].

Yin et al., "Effective Exon Skipping and Restoration of Dystrophin Expression by Peptide Nucleic Acid Antisense Oligonucleotides in mdx Mice," *Mol. Ther.*, vol. 16, No. 1, pp. 38-45 (Jan. 2008).

Zhang et al., "Efficient expression of naked DNA delivered intraarterially to limb muscles of nonhuman primates," *Hum. Gene. Ther.*, vol. 12, No. 4, pp. 427-438 (Mar. 2001) [Abstract].

European Patent Office, Partial European Search Report—Application No. EP 03 07 7205, dated Dec. 10, 2003 (6 pages).

European Patent Office, Annex to the European Search Report on European Patent Application No. EP 03 07 7205, dated Dec. 10, 2003 (1 page).

European Patent Office, Office Action—Application No. EP 05 076 770.6, dated Jan. 29, 2007 (5 pages).

Academisch Ziekenhuis Leiden, EPO-Munich, Translation of Japanese Patent Application No. 2000-125448 (D59), 31 pages, dated Sep. 27, 2000.

Academisch Ziekenhuis Leiden, EPO-Munich, Translation of Japanese Patent Application No. 2000-256547(D61), 42 pages, dated Aug. 23, 2001.

Authorized Officer: Romano, Alper, International Search Report for PCT/NL2010/050230, 5 pages, dated Jun. 24, 2010.

Authorized Officer: Lee W. Young, International Search Report, International Application No. PCT/US10/48532, 4 pages, dated Jan. 26, 2011.

GSK Press Release, "GSK and Prosensa Announce Primary Endpoint Not Met in Phase III Study of Drisapersen in Patients With Duchenne Muscular Dystrophy," *Prosensa Press Release*, 3 pages, Sep. 20, 2013.

C. Pallard, Letter from C. Pallard re: Patentee in the Above-Identified Opposition Appeal Proceedings, 25 pages, Jun. 10, 2014.

Aartsma-Rus et al., "Guidelines for Antisense Oligonucleotide Design and Insight into Splice-modulation Mechanisms." *Molecular Therapy*, vol. 17, No. 3, pp. 548-553 Mar. 2009.

Beggs, et al., "Detection of 98% of DMD/BMD gene deletions by polymerase chain reaction," *Human Genetics*, vol. 86, pp. 45-48 (1990).

Cavanaugh, Third-Party Submission Under 35 U.S.C. § 122(e) and 37 C.F.R. § 1.290 for U.S. Appl. No. 11/233,495, 6 pages, Jun. 5, 2013.

Dubowitz, Foreword, *Neuromuscular Disorders* 12 www.elsevier.com/locate/nmd, pp. S1-S2 (2002).

Dubowitz, "Special Centennial Workshop—101st ENMC International Workshop: Therapeutic possibilities in Duchenne Muscular Dystrophy, Nov. 30-Dec. 2, 2001, Naarden, The Netherlands" *Neuromuscul Disord.*, 12(4):421-31, May 2002.

Espinos, E., et al., "Efficient Non-Viral DNA-Mediated Gene Transfer to Human Primary Myoblasts Using Electroporation," *Neuromuscular Disorders*, 10, pp. 341-349 (2001).

Fainsod A, et al., "The dorsalizing and neural inducing gene follistatin is an antagonist of BMP-4" *Mech Dev.*, 63(1): 39-50 (1997).

Galderisi et al., "Antisense Oligonucleotides as Therapeutic Agents," *Journal of Cellular Physiology*, vol. 181, pp. 251-257 (1999).

Harding, et al., "The Influence of Antisense Oligonucleotide Length on Dystrophin Exon Skipping," *Molecular Therapy*, vol. 15, No. 1, pp. 157-166, Jan. 2007.

Heemskerk et al., "In vivo comparison of 2'-O-methyl phosphorothioate and morpholino antisense oligonucleotides for Duchenne muscular dystrophy exon skipping," *J. Gene Medicine*, 11:257-266. (2009).

Hyndman, "High affinity binding of transferrin in cultures of embryonic neurons from the chick retina," *Brain Res.*, 564(1):127-31 (1991).

Ito et al., "One of three examined purine-rich sequences selected from dystrophin exons exhibits splicing enhancer activity," *Acta Myologica*, vol. XX, pp. 151-153 (2001).

J.A. Kemp, Request for an Opinion under Section 74(A) in relation to Patent No. EP (UK) 1619249B in the name of Academisch Ziekenhuis Leiden, 33 pages, dated Apr. 20, 2009.

Jou, et al., "Deletion Detection in the Dystrophin Gene by Multiplex Gap Ligase Chain Reaction and Immunochromatographic Strip Technology," *Human Mutation*, 5:86-93 (1995).

(56) References Cited

OTHER PUBLICATIONS

Liu, et al., "Efficiency of DNA Transfection of Rat Heart Myoblast Cells H9c2(2-1) by Either Polyethyleneimine or Electroporation," *Appl Biochem Biotechnol*, 164: 1172-1182 (2011).
Lonza, "Amaxa Cell Line Nucleofector® Kit V" for C2C12, 4 pages [date unknown].
Ludolph, D., et al., "Transcription Factor Families: Muscling in on the Myogenic Program," *Dept. of Biological Sciences*, 9(15): 1595-604 (1995).
Matsuo, "Duchenne and Becker Muscular Dystrophy: From Gene Diagnosis to Molecular Therapy", *IUBMB Life*, vol. 53, pp. 147-152 (2002).
Matteucci, "Structural modifications toward improved antisense oligonucleotides" *Perspectives in Drug Disc and Design*, vol. 4, pp. 1-16 (1996).
Miller KJ et al., "Antisense oligonucleotides: strategies for delivery" *PSST* vol. 1, No. 9; pp. 377-386 (1988).
Onlo, Comparative Analysis of AONs for inducing the skipping of exon 53 from the dystrophin gene in human control muscle cells., EP1619249, 3 pages, Jan. 8, 2014.
Onlo, Comparative analysis of AONs for inducing the skipping of exon 45 and 53 from the dystrophin gene in human control muscle cells, EP1619249, 3 pages, Aug. 23, 2013.
Onlo Nederlandsch Octrooibureau, Exon 53 Alignment—EP1619249, 1 page, Jan. 8, 2014.
Onlo Nederlandsch Octrooibureau, Grounds of Appeal,—EP1619249, 16 pages, Aug. 23, 2013.
Onlo Nederlandsch Octrooibureau, List of all submitted documents—EP1619249, 4 pages, Aug. 23, 2013.
Onlo Nederlandsch Octrooibureau, Reply to the Grounds of Appeal filed in Opposition Proceedings of EP1619249, 35 pages, dated Jan. 8, 2014.
Peterson TC, et al., "Selective Down-Regulation of c-jun Gene Expression by Pentoxifylline and c-jun Antisense Interrupts Platelet-Derived Growth Factor Signaling: Pentoxifylline Inhibits Phosphorylation of c-Jun on Serine 73" *Mol Pharmacol.*, 61(6): 1476-88 (2002).
Phillips MI, "Antisense Inhibition and Adeno-Associated Viral Vector Delivery for Reducing Hypertension" *Hypertension*, vol. 29, 177-187 (1997).
Sarepta Therapeutics Inc., "Sarepta Therapeutics and University of Western Australia Announce Exclusive Worldwide Licensing Agreement for Exon-Skipping Program in Duchenne Muscular Dystrophy," *News Release*, EP1619249, 3 pages (2013).
Schnell, "Declaration of Dr. Fred Schnell in Support of Appeal of the Opposition Division's Decision to Maintain EP-B1 1 619 249 in amended form," 6 pages, Jan. 8, 2014.
Squires, "An Introduction to Nucleside and Nucelotide Analogues," Antiviral Therapy6 (Suppl. 3): 1-14, 2001.
Summerton et al., "Morpholino Antisense Oligomers: Design, Preparation, and Properties," *Antisense & Nucleic Acid Drug Development*, vol. 7, pp. 187-195 (1997).
Takeshima Y, et al., "Expression of Dystrophin Protein in Cultured Duchenne Muscular Dystrophy Cells by Exon Skipping Induced by Antisense Oligonucleotide" (Abstract); Abstract of the Japan Society of Human Genetics General Meeting Program, 8 pages, Nov. 17-19, 1999.
Takeshima, et al., "Basic research for treatment of Duchene muscular dystrophy using induction of exon skipping by means of antisense oligo DNA: effect of in vivo administration in mice," *Park IP Translations*, vol. 15, No. 2, 6 pages (2012).
van Deutekom, Declaration of Dr. JCT Van Deutekom, EP1619249, 6 pages, Jan. 7, 2014.
van Deutekom, Declaration of Dr. JCT van Deutekom, EP1619249, 2 pages, Aug. 23, 2013.
van Deutekom, J., Declaration of Dr. Judith van Deutekom, 8 pages, Jun. 10, 2014.
Vossius & Partners, "Statement of Grounds of Appeal" filed in the opposition proceeding of EP1619249; dated Aug. 23, 2013, 41 pages.
Vossius & Partners, Reply of the Opponent to the Grounds of Appeal, 31 pages, Jan. 8, 2014.
Weiler et al., "Identical mutation in patients with limb girdle muscular dystrophy type 2B or Miyoshi myopathy suggests a role for modifier gene(s)," *Human Molecular Genetics*, vol. 8, No. 5, pp. 871-877 (1999).
University of Western Australia, *University of Western Australia* (U.S. Pat. No. 7,960,541 and 7,807,816) v. *Academisch Ziekenhuis Leiden* (U.S. Appl. No. 13/550,210), University of Western Australia Motion 3 (for judgment that Claims 11-12, 14-15, and 17-29 of U.S. Appl. No. 13/55,210 are barred under 35 U.S.C. §135(b)); 25 pages, filed Nov. 18, 2014.
University of Western Australia, *University of Western Australia* (U.S. Pat. No. 7,960,541 and 7,807,816) v. *Academisch Ziekenhuis Leiden* (U.S. Appl. No. 13/550,210), University of Western Australia Motion 2 (for Judgment Under 35 U.S.C. §112(b)), 32 pages, filed Nov. 18, 2014.
University of Western Australia, *University of Western Australia* (U.S. Pat. No. 7,960,541 and 7,807,816) v. *Academisch Ziekenhuis Leiden* (U.S. Appl. No. 13/550,210), University of Western Australia Motion 1 (for Judgment Under 35 U.S.C. §112(a)), 38 pages, filed Nov. 18, 2014.
University of Western Australia, *University of Western Australia* (U.S. Pat. No. 8,455,636, 7,960,541, 7,807,816, 8,486,907) v. *Academisch Ziekenhuis Leiden* (U.S. Appl. Nos. 11/233,495, 13/550,210, 14/198,992), Declaration of Matthew J.A. Wood, M.D. ,D. Phil.—UVA Exhibit 2081, 184 pages, filed Sep. 19, 2014.
University of Western Australia, *University of Western Australia* (U.S. Pat. No. 7,960,541, 7,807,816) v. *Academisch Ziekenhuis Leiden* (U.S. Appl. No. 13/550,210), University of Western Australia List of Proposed Motions, 6 pages, filed Sep. 10, 2014.
Academisch Ziekenhuis Leiden, *University of Western Australia* (U.S. Pat. No. 7,960,541, 7,807,816) v. *Academisch Ziekenhuis Leiden* (U.S. Appl. No. 13/550,210), Academisch Ziekenhuis Leiden's List of Proposed Motions, 8 pages, filed Sep. 10, 2014.
Academisch Ziekenhuis Leiden, *University of Western Australia* (U.S. Pat. No. 7,960,541, 7,807,816) v. *Academisch Ziekenhuis Leiden* (U.S. Appl. No. 13/550,210), Academisch Ziekenhuis Leiden's Substantive Motion 1 (for Judgment that UWA's Claims are Unpatentable Under 35 U.S.C. §§ 102 and 103) 69 pages, filed Nov. 18, 2014.
Academisch Ziekenhuis Leiden, *University of Western Australia* (U.S. Pat. No. 7,960,541, 7,807,816) v. *Academisch Ziekenhuis Leiden* (U.S. Appl. No. 13/550,210), Academisch Ziekenhuis Leiden's Substantive Motion 2 (to Deny UWA the Benefit of AU2004903474, 24 pages, filed Nov. 18, 2014.
Academisch Ziekenhuis Leiden, *University of Western Australia* (U.S. Pat. No. 7,960,541, 7,807,816) v. *Academisch Ziekenhuis Leiden* (U.S. Appl. No. 13/550,210), Academisch Ziekenhuis Leiden's Substantive Motion 3 (for Judgment of Unpatentability Based on Myriad), 20 pages, filed Nov. 18, 2014.
Academisch Ziekenhuis Leiden, *University of Western Australia* (U.S. Pat. No. 7,960,541, 7,807,816) v. *Academisch Ziekenhuis Leiden* (U.S. Appl. No. 13/550,210), Declaration of Erik Sontheimer, Ph.D., 112 pages, filed Nov. 17, 2014.
University of Western Australia, *University of Western Australia* (U.S. Pat. No. 8,455,636) v. *Academisch Ziekenhuis Leiden* (U.S. Appl. No. 11/233,495), University of Western Australia List of Proposed Motions, 7 pages, filed Sep. 10, 2014.
University of Western Australia, *University of Western Australia* (U.S. Pat. No. 8,455,636) v. *Academisch Ziekenhuis Leiden* (U.S. Appl. No. 11/233,495), University of Western Australia Motion 1 (for Judgment Under 35 U.S.C. §112(a)), 40 pages, filed Nov. 18, 2014.
University of Western Australia, *University of Western Australia* (U.S. Pat. No. 8,455,636) v. *Academisch Ziekenhuis Leiden* (U.S. Appl. No. 11/233,495), University of Western Australia Motion 2 (for Judgment Under 35 U.S.C. §112(b)), 34 pages, filed Nov. 18, 2014.
University of Western Australia, *University of Western Australia* (U.S. Pat. No. 8,455,636) v. *Academisch Ziekenhuis Leiden* (U.S. Appl. No. 11/233,495), University of Western Australia Motion 3 (Requesting an Additional Interference Between UWA US Patent No. 8,455,636 and Academisch Ziekenhuis Leiden's U.S. Appl. No. 14/248,279), 36 pages, filed Nov. 18, 2014.

(56) References Cited

OTHER PUBLICATIONS

Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 1 (for Judgment that UWA Claims are Unpatentable Under 35 U.S.C. §§ 102 and 103) 69 pages, filed Nov. 18, 2014.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's Substantive Motion 3 (for Judgment of Unpatentability based on Myriad), 19 pages, filed Nov. 18, 2014.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Substantive Motion 2 (to Deny UWA the Benefit of AU 2004903474), 23 pages, filed Nov. 18, 2014.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden's List of Proposed Motions, 6 pages, filed Sep. 10, 2014.
University of Western Australia, *University of Western Australia* (U.S. Pat. No. 8,486,907) v. *Academisch Ziekenhuis Leiden* (U.S. Appl. No. 14/198,992),University of Western Australia Motion 1 (to Maintain Interference Between UWA US Patent No. 8,486,907 and Academisch Ziekenhuis Leiden's U.S. Appl. No. 14/198,992), 45 pages, filed Nov. 18, 2014.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Responsive Motion 4 (to Add Two New Claims), 65 pages, filed Dec. 23, 2014.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Responsive Motion 4 (to Add Two New Claims), 57 pages, filed Dec. 23, 2014.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Second Declaration of Erik Sontheimer, Ph.D., 44 pages, filed Dec. 23, 2014.
University of Western Australia, *University of Western Australia* (U.S. Pat. No. 8,455,636) v. *Academisch Ziekenhuis Leiden* (U.S. Appl. No. 11/233,495), University of Western Australia Exhibit List as of Feb. 17, 2015, 8 pages, filed Feb. 17, 2015.
University of Western Australia, *University of Western Australia* (U.S. Pat. No. 8,455,636) v. *Academisch Ziekenhuis Leiden* (U.S. Appl. No. 11/233,495), University of Western Australia Opposition 1 (Regarding Patentability Under 35 U.S.C. § 102/103), 38 pages, filed Feb. 17, 2015.
University of Western Australia, *University of Western Australia* (U.S. Pat. No. 8,455,636) v. *Academisch Ziekenhuis Leiden* (U.S. Appl. No. 11/233,495), University of Western Australia Opposition 2 (to Retain UWA's Benefit of AU 2004903474), 37 pages, filed Feb. 17, 2015.
University of Western Australia, *University of Western Australia* (U.S. Pat. No. 8,455,636) v. *Academisch Ziekenhuis Leiden* (U.S. Appl. No. 11/233,495), University of Western Australia Opposition 3 (Regarding Patentability Under 35 U.S.C. § 101), 22 pages, filed Feb. 17, 2015.
University of Western Australia, *University of Western Australia* (U.S. Pat. No. 8,455,636) v. *Academisch Ziekenhuis Leiden* (U.S. Appl. No. 11/233,495), University of Western Australia Opposition 4 (to deny entry of AZL's Proposed New Claims 104 and 105), 36 pages, filed Feb. 17, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Feb. 17, 2015), 18 pages, filed Feb. 17, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 1 (35 U.S. C. § 112(a)), 93 pages, filed Feb. 17, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 2 (Indefiniteness), 31 pages, filed Feb. 17, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Opposition 3 (Standing Order ¶ 203.1 and 37 C.F.R. § 41.202(a) and (e)), 20 pages, filed Feb. 17, 2015.
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Exhibit List as of Feb. 17, 2015, 8 pages, filed Feb. 17, 2015.
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 1 (Regarding Patentability Under 35 U.S.C. § 102/103), 39 pages, filed Feb. 17, 2015.
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 2 (to Retain UWA's Benefit of AU 2004903474), 31 pages, filed Feb. 17, 2015.
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 3 (Regarding Patentability Under 35 U.S.C. § 101), 22 pages, filed Feb. 17, 2015.
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Opposition 4 (to deny entry of AZL's Proposed New Claims 30 and 31), 36 pages, filed Feb. 17, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden List of Exhibits (as of Feb. 17, 2015) 18 pages, filed Feb. 17, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden Opposition 1 (35 U.S.C. § 112(a)), 83 pages, filed Feb. 17, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden Opposition 2 (Indefiniteness), 32 pages, filed Feb. 17, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210) Academisch Ziekenhuis Leiden Opposition 3 (U.S.C. § 135(b)), 44 pages, filed Feb. 17, 2015.
Academisch Ziekenhuis Leiden, *University of Western Australia* (U.S. Pat. No. 8,486,907) v. *Academisch Ziekenhuis Leiden* (U.S. Appl. No. 14/198,992) Academisch Ziekenhuis Leiden List of Exhibits (as of Feb. 17, 2015) 3 pages, filed Feb. 17, 2015.
Academisch Ziekenhuis Leiden, *University of Western Australia* (U.S. Pat. No. 8,486,907) v. *Academisch Ziekenhuis Leiden* (U.S. Appl. No. 14/198,992) Academisch Ziekenhuis Leiden Opposition 1 (Standing Order ¶ 203.1 and 37 C.F.R. § 41.202 (a) and (e)) 20 pages, filed Feb. 17, 2015.
University of Western Australia, *University of Western Australia* (U.S. Pat. No. 8,455,636) v. *Academisch Ziekenhuis Leiden* (U.S. Appl. No. 11/233,495) and *University of Western Australia* (Patent Nos. 7,960,541 and 7,807,816) v. *Academisch Ziekenhuis Leiden* (U.S. Appl. No. 13/550,210), Second Declaration of Matthew J.A. Wood, M.D., D. Phil., 78 pages, filed Feb. 17, 2015.
Academisch Ziekenhuis Leiden, *University of Western Australia* (U.S. Pat. No. 8,455,636) v. *Academisch Ziekenhuis Leiden* (U.S. Appl. No. 11/233,495) and *University of Western Australia* (Patent Nos. 7,960,541 and 7,807,816) v. *Academisch Ziekenhuis Leiden* (U.S. Appl. No. 13/550,210), 3$^{rd}$ Declaration of Erik J. Sontheimer, Ph.D., 123 pages, filed Feb. 17, 2015.

(56) References Cited

OTHER PUBLICATIONS

Academisch Ziekenhuis Leiden, *University of Western Australia* (U.S. Pat. No. 8,455,636) v. *Academisch Ziekenhuis Leiden* (U.S. Appl. No. 11/233,495) and *University of Western Australia* (Patent Nos. 7,960,541 and 7,807,816) v. *Academisch Ziekenhuis Leiden* (U.S. Appl. No. 13/550,210), Declaration of Judith Van Deutekom, 45 pages, filed Feb. 17, 2015.
University of Western Australia, *University of Western Australia* (U.S. Pat. No. 8,455,636) v. *Academisch Ziekenhuis Leiden* (U.S. Appl. No. 11/233,495) University of Western Australia Objections (to Opposition Evidence) 15 pages, filed Feb. 24, 2015.
University of Western Australia, *University of Western Australia* (U.S. Pat. Nos. 7,960,541 and 7,807,816) v. *Academisch Ziekenhuis Leiden* (U.S. Appl. No. 13/550,210) University of Western Australia Objections (to Opposition Evidence) 15 pages, filed Feb. 24, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 1 (for Judgment that UWA's Claims are Unpatentable Under 35 U.S.C. §§ 102 and 103) 17 pages, filed Apr. 3, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 2 (to Deny the Benefit of AU 2004903474) 11 pages, filed Apr. 3, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 3 (for Judgment of Unpatentability based on Myriad) 12 pages, filed Apr. 3, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Reply 4 (in Support of Responsive Motion 4 to Add Two New Claims) 17 pages, filed Apr. 3, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden List of Exhibits (as of Apr. 3, 2015) 18 pages, filed Apr. 3, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 1 (for Judgment that UWA's Claims are Unpatentable Under 35 U.S.C. §§ 102 and 103) 17 pages, filed Apr. 3, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 2 (to Deny the Benefit of AU 2004903474) 12 pages, filed Apr. 3, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 3 (for Judgment of Unpatentability based on Myriad) 13 pages, filed Apr. 3, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 4 (in Support of Responsive Motion 4 to Add Two New Claims) 17 pages, filed Apr. 3, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden List of Exhibits (as of Apr. 3, 2015) 18 pages, filed Apr. 3, 2015.
University of Western Australia, *University of Western Australia* (U.S. Pat. No. 8,455,636) v. *Academisch Ziekenhuis Leiden* (U.S. Appl. No. 11/233,495), University of Western Australia Reply 1 (to AZL Opposition 1) 28 pages, filed Apr. 3, 2015.
University of Western Australia, *University of Western Australia* (U.S. Pat. No. 8,455,636) v. *Academisch Ziekenhuis Leiden* (U.S. Appl. No. 11/233,495), University of Western Australia Reply 2 (to AZL Opposition 2) 22 pages, filed Apr. 3, 2015.
University of Western Australia, *University of Western Australia* (U.S. Pat. No. 8,455,636) v. *Academisch Ziekenhuis Leiden* (U.S. Appl. No. 11/233,495), University of Western Australia Reply 3 (to Institute an Interference) 17 pages, filed Apr. 3, 2015.
University of Western Australia, *University of Western Australia* (U.S. Pat. No. 8,455,636) v. *Academisch Ziekenhuis Leiden* (U.S. Appl. No. 11/233,495), University of Western Australia Exhibit List , 10 pages, filed Apr. 3, 2015.
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Request for Oral Argument, 3 pages, filed Apr. 10, 2015.
University of Western Australia, *University of Western Australia* (U.S. Pat. No. 8,455,636) v. *Academisch Ziekenhuis Leiden* (U.S. Appl. No. 11/233,495 University of Western Australia Request for Oral Argument, 4 pages, filed Apr. 10, 2015.
University of Western Australia, *University of Western Australia* (U.S. Pat. No. 8,455,636) v. *Academisch Ziekenhuis Leiden* (U.S. Appl. No. 11/233,495 University of Western Australia Miscellaneous Motion 4 (to exclude evidence), 21 pages, filed Apr. 10, 2015.
University of Western Australia, *University of Western Australia* (U.S. Pat. No. 8,455,636) v. *Academisch Ziekenhuis Leiden* (U.S. Appl. No. 11/233,495 University of Western Australia Exhibit List, 10 pages, filed Apr. 10, 2015.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 1 (to AZL Opposition 1) 28 pages, filed Apr. 3, 2015.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 2 (to AZL Opposition 2) 22 pages, filed Apr. 3, 2015.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 3 (for judgment under 35 U.S.C. § 135(b)) 19 pages, filed Apr. 3, 2015.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List, 10 pages, filed Apr. 3, 2015.
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Request for Oral Argument, 3 pages, filed Apr. 10, 2015.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Request for Oral Argument, 4 pages, filed Apr. 10, 2015.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Miscellaneous Motion 4 (to exclude evidence), 21 pages, filed Apr. 10, 2015.
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List, 10 pages, filed Apr. 10, 2015.

\* cited by examiner

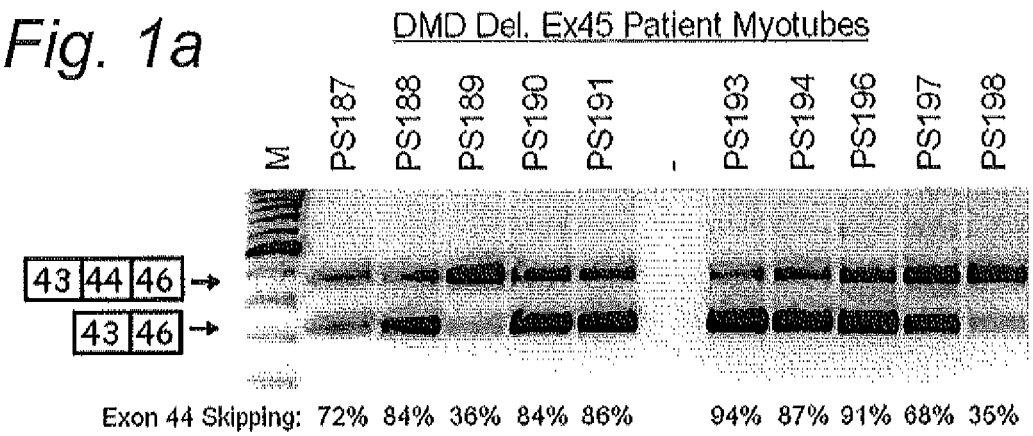
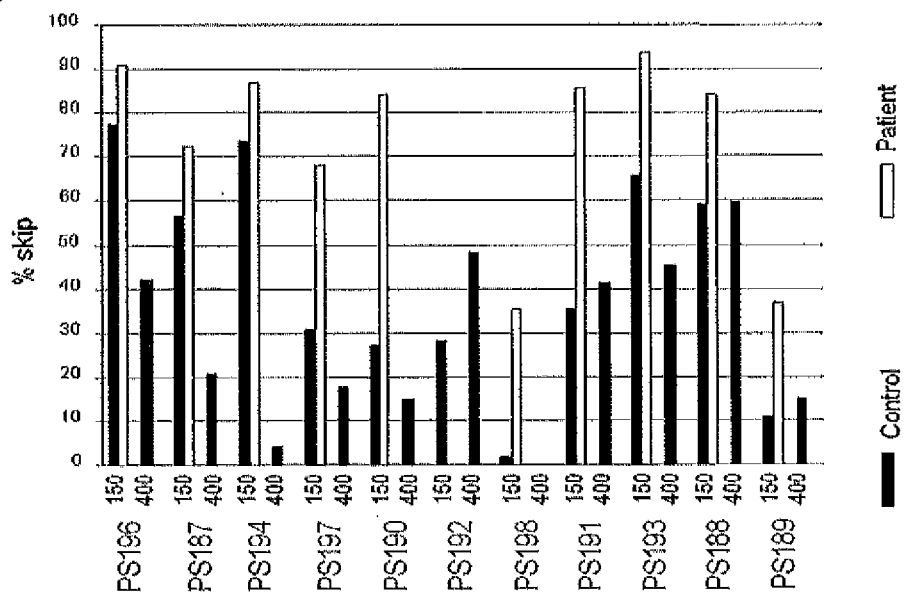
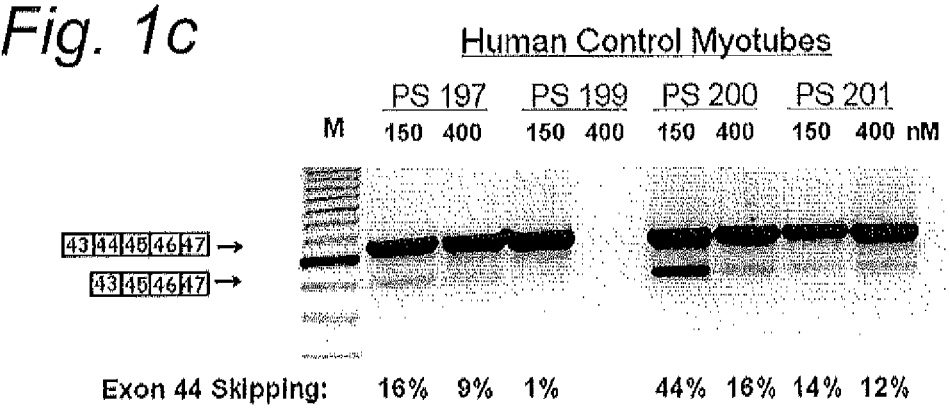

Human control PB-MNCs

Monkey PB-MNCs
T: IV 6 mg/kg PS188

METHOD FOR EFFICIENT EXON (44) SKIPPING IN DUCHENNE MUSCULAR DYSTROPHY AND ASSOCIATED MEANS

CROSS-REFERENCE TO RELATED APPLICATIONS

This application is a continuation of PCT International Application No. PCT/NL2009/050258, filed May 14, 2009, which claims the benefit of European Application No. 08156193.8, filed May 14, 2008 and U.S. Provisional Application No. 60/128,010, filed May 15, 2008, the contents of which are incorporated herein by reference in their entirety.

FIELD OF THE INVENTION

The invention relates to the field of genetics, more specifically human genetics. The invention in particular relates to the modulation of splicing of the human Duchenne Muscular Dystrophy gene.

BACKGROUND

Myopathies are disorders that result in functional impairment of muscles. Muscular dystrophy (MD) refers to genetic diseases that are characterized by progressive weakness and degeneration of skeletal muscles. Duchenne muscular dystrophy (DMD) and Becker muscular dystrophy (BMD) are the most common childhood forms of muscular dystrophy. They are recessive disorders and because the gene responsible for DMD and BMD resides on the X-chromosome, mutations mainly affect males with an incidence of about 1 in 3500 boys.

DMD and BMD are caused by genetic defects in the DMD gene encoding dystrophin, a muscle protein that is required for interactions between the cytoskeleton and the extracellular matrix to maintain muscle fiber stability during contraction. DMD is a severe, lethal neuromuscular disorder resulting in a dependency on wheelchair support before the age of 12 and DMD patients often die before the age of thirty due to respiratory- or heart failure. In contrast, BMD patients often remain ambulantory until later in life, and have near normal life expectancies. DMD mutations in the dystrophin gene are characterized by frame shifting insertions or deletions or nonsense point mutations, resulting in the absence of functional dystrophin. BMD mutations in general keep the reading frame intact, allowing synthesis of a partly functional dystrophin.

Several possible treatments have been investigated over the last 20 years, including myoblast-transplantation, DNA-targeted gene therapy, and antisense-mediated exon skipping (van Deutekom and van Ommen, (2003), Nat. Rev. Genet., 4(10):774-83). Antisense-mediated exon skipping aims at transforming out-of-frame mutations present in DMD patients into in-frame BMD-like mutations that result in synthesis of an at least partially functional dystrophin, which will prolong the viability of the muscles (Aartsma-Rus and van Ommen, (2007), RNA, 13(10): 1609-24).

Exon skipping can be induced by antisense oligonucleotides (AON) directed against the splice donor or splice acceptor site of a splice junction that are involved in the enzymatic process of exon joining, or against exon-internal sequences. In general, splice donor and splice acceptor sites comprise conserved sequences and targeting these sequences has the inevitable risk of co-targeting splice sites of additional exons from DMD or other gene transcripts.

Exon 44 of the DMD gene consists of 148 base pairs. Therapeutic skipping of exon 44 would restore the correct reading frame in DMD patients having deletions including but not limited to exons 03-43, 05-43, 06-43, 10-43, 13-43, 14-43, 17-43, 19-43, 28-43, 30-43, 31-43, 33-43, 34-43, 35-43, 36-43, 37-43, 38-43, 40-43, 41-43, 42-43, 43, 45, 45-54, and 45-68, or having a duplication of exon 44. Furthermore, for some DMD patients the mutations are such that the simultaneous skipping of one or more exons is required in addition to exon 44 skipping to restore the reading frame. Non-limiting examples of such mutations are nonsense point mutations in the flanking exons 43 or 45, requiring exon 43+44 skipping or exon 44+45 skipping respectively. The aforementioned mutations in total occur in about 6-8% of all DMD patients. The majority of resulting dystrophin proteins will be truncated in the central rod domain of the protein, leaving the essential N-terminal actin-binding domain and the C-terminal domain binding to dystrobrevin and syntrophin, and the β-dystroglycan-binding C-terminal cysteine-rich domain, intact.

DESCRIPTION

The present invention identifies four different regions in exon 44 that are particularly suited for inducing skipping of exon 44. The invention thus provides a method for modulating splicing of exon 44 of the DMD gene in a cell, the method comprising providing said cell with a molecule that binds to a nucleotide sequence comprising SEQ ID NO. 1: 5'-GUG-GCUAACAGAAGCU; SEQ ID NO. 2: 5'-GGGAACAUGC-UAAAUAC, SEQ ID NO. 3: 5'-AGACACAAAUUC-CUGAGA, or SEQ ID NO. 4: 5'-CUGUUGAGAAA. This molecule preferably binds or is complementary to any of SEQ ID NO: 1, 2, 3, or 4 when SEQ ID NO:1, 2, 3, or 4 is present within exon 44 of the DMD pre-mRNA.

Throughout the application, the expression "inducing skipping" is synonymous of "modulating splicing".

It was found that a molecule that binds to a nucleotide sequence comprising SEQ ID NO. 1: 5'-GUGGCUAACA-GAAGCU; SEQ ID NO. 2: 5'-GGGAACAUGCUAAAUAC, SEQ ID NO. 3: 5'-AGACACAAAUUCCUGAGA, or SEQ ID NO. 4: 5'-CUGUUGAGAAA results in highly efficient skipping of exon 44 in cells provided with this molecule. Furthermore, none of the indicated sequences is derived from conserved parts of splice junction sites. Therefore, said molecule is not likely to mediate differential splicing of other exons from the DMD pre-mRNA or exons from other genes. In addition, other (immuno)toxicity is preferably avoided by avoiding CpG pairs in the molecule that binds to a nucleotide sequence as defined herein above.

Exon skipping refers to the induction in a cell of a mature mRNA that does not contain a particular exon that is normally present therein. Exon skipping is achieved by providing a cell expressing the pre-mRNA of said mRNA, with a molecule capable of interfering with sequences such as, for example, the splice donor or splice acceptor sequence required for allowing the enzymatic process of splicing, or that is capable of interfering with an exon inclusion signal required for recognition of a stretch of nucleotides as an exon to be included into the mRNA. The term pre-mRNA refers to a non-processed or partly processed precursor mRNA that is synthesized from a DNA template in the cell nucleus by transcription.

Certain methods of the invention will alleviate one or more characteristics of a myogenic cell or muscle cell of a DMD patient having deletions including, but not limited to, exons 03-43, 05-43, 06-43, 10-43, 13-43, 14-43, 17-43, 19-43, 28-43, 30-43, 31-43, 33-43, 34-43, 35-43, 36-43, 37-43, 38-43, 40-43, 41-43, 42-43, 43, 45, 45-54, and 45-68, or having a duplication of exon 44. Furthermore, the removal of a flanking exon, such as, for example, exon 43 or exon 45, because of a nonsense point mutation in the flanking exon, will result in an out of frame transcript. The additional skipping of exon 44, in combination with skipping of the flanking exon, will restore the reading frame of the DMD gene in myogenic cells or muscle cells of DMD patients. Non-limiting examples of such mutations are nonsense point mutations in the flanking exons 43 or 45, requiring exon 43+44 skipping or exon 44+45 skipping respectively.

In an embodiment, a method of the invention may also alleviate one or more characteristics of a myogenic cell or muscle cell of a strong BMD patient, to the characteristics of a mild BMD patient. The characteristics of a cell of a DMD or BMD patient include increased calcium uptake by muscle cells, increased collagen synthesis, altered morphology, altered lipid biosynthesis, increased oxidative stress, and/or damaged sarcolemma. Preferred embodiments of a method of the invention are later defined herein.

In one embodiment, a molecule as defined herein can be a compound molecule that binds and/or is complementary to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zinc-finger proteins that bind specific nucleotide sequences are disclosed by Friesen and Darby, Nature Structural Biology 5: 543-546 (1998) which is herein incorporated by reference. Binding to one of the specified SEQ ID NO: 1, 2, 3, or 4 sequence, preferably in the context of exon 44 of DMD may be assessed via techniques known to the skilled person. A preferred technique is gel mobility shift assay as described in EP 1 619 249. In a preferred embodiment, a molecule is said to bind to one of the specified sequences as soon as a binding of said molecule to a labelled sequence SEQ ID NO: 1, 2, 3 or 4 is detectable in a gel mobility shift assay. Alternatively or in combination with previous embodiment, a molecule is an oligonucleotide which is complementary or substantially complementary to SEQ ID NO:1, 2, 3, or 4 or part thereof as later defined herein. The term "substantially" complementary used in this context indicates that one or two or more mismatches may be allowed as long as the functionality, i.e. inducing skipping of exon 44, is still acceptable.

The invention provides a method for designing a molecule, preferably an oligonucleotide able to induce the skipping of exon 44 of the DMD gene. First said oligonucleotide is selected to bind to one of SEQ ID NO: 1, 2, 3, or 4 or parts thereof as earlier defined herein. Subsequently, in a preferred method at least one of the following aspects has to be taken into account for designing, improving said molecule any further:

The molecule does not contain a CpG,
The molecule does not contain a G-quartet motif,
The molecule has acceptable RNA binding kinetics and/or thermodynamic properties.

The presence of a CpG in an oligonucleotide is usually associated with an increased immunogenicity of said oligonucleotide (Dorn and Kippenberger, Curr Opin Mol Ther 2008 10(1) 10-20). This increased immunogenicity is undesired since it may induce the breakdown of muscle fibers. Immunogenicity may be assessed in an animal model by assessing the presence of $CD4^+$ and/or $CD8^+$ cells and/or inflammatory mononucleocyte infiltration in muscle biopsy of said animal. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person. An increase in immunogenicity may be assessed by detecting the presence or an increasing amount of a neutralizing antibody or an antibody recognizing said oligonucleotide using a standard immunoassay.

An oligonucleotide comprising a G-quartet motif has the tendency to form a quadruplex, a multimer or aggregate formed by the Hoogsteen base-pairing of four single-stranded oligonucleotides (Cheng and Van Dyke, Gene. 1997 Sep. 15;197(1-2):253-60), which is of course not desired: as a result the efficiency of the oligonucleotide is expected to be decreased. Multimerisation or aggregation is preferably assessed by standard polyacrylamide non-denaturing gel electrophoresis techniques known to the skilled person. In a preferred embodiment, less than 20% or 15%, 10%, 7%, 5% or less of a total amount of an oligonucleotide of the invention has the capacity to multimerise or aggregate assessed using the assay mentioned above.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (world wide web at unc.edu/~cail/biotool/oligo/index.html) for single stranded RNA using the basic Tm and the nearest neighbour model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 65° C. and an acceptable free energy may be ranged between 15 and 45 kcal/mol.

The skilled person may therefore first choose an oligonucleotide as a potential therapeutic compound as binding and/or being complementary to SEQ ID NO:1, 2, 3, or 4 of exon 44 or parts thereof as defined herein. The skilled person may check that said oligonucleotide is able to bind to said sequences as earlier defined herein. Optionally in a second step, he may use the invention to further optimise said oligonucleotide by checking for the absence of CpG, the absence of a G-quartet motif, and/or by optimizing its Tm and/or free energy of the AON-target complex. He may try to design an oligonucleotide wherein no CpG and/or no G-quartet motif are present and/or wherein a more acceptable Tm and/or free energy are obtained by choosing a distinct sequence of exon 44 (for example SEQ ID NO:1, 2, 3, or 4) to which the oligonucleotide is complementary. Alternatively, if an oligonucleotide complementary to a given stretch within SEQ ID NO:1, 2, 3 or 4 of exon 44, comprises a CpG, a G-quartet motif and/or does not have an acceptable Tm and/or free energy, the skilled person may improve any of these parameters by decreasing the length of the oligonucleotide, and/or by choosing a distinct stretch within any of SEQ ID NO: 1, 2, 3, or 4 to which the oligonucleotide is complementary and/or by altering the chemistry of the oligonucleotide.

As an example, if one chooses SEQ ID NO:1, several oligonucleotides were designed which were found to bind this sequence: SEQ ID NO: 5, 49, and 54. The oligonucleotide comprising SEQ ID NO:5 was found to have the most optimal RNA binding kinetics and/or thermodynamic properties, such as the most optimal Tm. When we tested the functionality of these oligonucleotides to induce the skipping of exon 44, it was confirmed that an oligonucleotide comprising SEQ ID NO:5 is the most efficient of these four oligonucleotides. Each of these oligonucleotides is functional in the sense of the invention. However, an oligonucleotide comprising SEQ ID NO:5 is the most preferred oligonucleotide identified that binds and/or is complementary to SEQ ID NO:1.

At any step of the method, an oligonucleotide of the invention is preferably an olignucleotide, which is still able to exhibit an acceptable level of a functional activity. A functional activity of said oligonucleotide is preferably to induce the skipping of exon 44 of the DMD gene to a certain extent, to provide an individual with a functional dystrophin protein and/or mRNA and/or at least in part decreasing the production of an aberrant dystrophin protein and/or mRNA. Each of these features is later defined herein. Such functional activity may be measured in a muscular tissue or in a muscular cell of an individual or in vitro in a cell. The assessment of the functionality may be carried out at the mRNA level, preferably using RT-PCR. The assessment of the functionality may be carried out at the protein level, preferably using western blot analysis or immunofluorescence analysis of cross-sections. In a preferred embodiment, an oligonucleotide is said to induce skipping of exon 44 of a DMD gene, when tested in a muscle cell of a DMD patient, by RT-PCR, the exon 44 skipping percentage is of at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

In a preferred embodiment, such oligonucleotide is preferably a medicament. More preferably, said medicament is for preventing or treating Duchenne Muscular Dystrophy or Becker Muscular Dystrophy in an individual or a patient. As defined herein a DMD pre-mRNA preferably means the pre-mRNA of a DMD gene of a DMD or BMD patient. A patient is preferably intended to mean a patient having DMD or BMD or a patient susceptible to develop DMD or BMD due to his or her genetic background.

In the case of a DMD patient, an oligonucleotide used will preferably correct at least one of the DMD mutations as present in the DMD gene of said patient and therefore will preferably create a dystrophin that will look like a BMD dystrophin: said dystrophin will preferably be a functional dystrophin as later defined herein.

In the case of a BMD patient, an oligonucleotide as used will preferably correct at least one of the BMD mutations as present in the DMD gene of said patient and therefore will preferably create a, or more of a, dystrophin, which will be more functional than the dystrophin which was originally present in said BMD patient. Even more preferably, said medicament increases the production of a functional or more functional dystrophin protein and/or mRNA and/or at least in part decreases the production of an aberrant or less functional dystrophin protein and/or mRNA in an individual.

Preferably, a method of the invention increases production of a more functional dystrophin protein and/or mRNA and/or decreases the production of an aberrant or less functional dystrophin protein and/or mRNA in a patient, by inducing and/or promoting skipping of at least exon 44 of the DMD pre-mRNA as identified herein in one or more cells, preferably muscle cells of said patient. Increasing the production of a more functional dystrophin protein and/or mRNA and/or decreasing the production of an aberrant dystrophin protein and/or mRNA in a patient is typically applied in a DMD patient. Increasing the production of a more functional or functional dystrophin and/or mRNA is typically applied in a BMD patient.

Therefore a preferred method is a method, wherein in a patient or in one or more cells of said patient, production of a more functional or functional dystrophin protein and/or mRNA is increased and/or the production of an aberrant dystrophin protein and/or mRNA in said patient is decreased, wherein the level of said aberrant or more functional dystrophin protein and/or mRNA is assessed by comparison to the level of said dystrophin and/or mRNA in said patient at the onset of the method.

As defined herein, a functional dystrophin is preferably a wild type dystrophin corresponding to a protein having the amino acid sequence as identified in SEQ ID NO: 55. A functional dystrophin is preferably a dystrophin, which has an actin binding domain in its N terminal part (first 240 amino acids at the N terminus), a cystein-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO: 55. In another embodiment, a functional dystrophin is a dystrophin, which exhibits at least to some extent an activity of a wild type dystrophin. "At least to some extent" preferably means at least 30%, 40%, 50%, 60%, 70%, 80%, 90%, 95% or 100% of a corresponding activity of a wild type functional dystrophin. In this context, an activity of a wild type dystrophin is preferably binding to actin and to the dystrophin-associated glycoprotein complex (DGC) (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144.). Binding of dystrophin to actin and to the DGC complex may be visualized by either co-immunoprecipitation using total protein extracts or immunofluorescence analysis of cross-sections, from a biopsy of a muscle suspected to be dystrophic, as known to the skilled person. Individuals suffering from Duchenne muscular dystrophy typically have a mutation in the gene encoding dystrophin that prevents synthesis of the complete protein, i.e. a premature stop prevents the synthesis of the C-terminus of the protein. In Becker muscular dystrophy the dystrophin gene also comprises a mutation compared to the wild type but the mutation does typically not include a premature stop and the C-terminus of the protein is typically synthesized. As a result a functional dystrophin protein is synthesized that has at least the same activity in kind as a wild type protein, although not necessarily the same amount of activity. In a preferred embodiment, a functional dystrophin protein means an in frame dystrophin gene. The genome of a BMD individual typically encodes a dystrophin protein comprising the N terminal part (first 240 amino acids at the N terminus), a cystein-rich domain (amino acid 3361 till 3685) and a C terminal domain (last 325 amino acids at the C terminus) but its central rod shaped domain may be shorter than the one of a wild type dystrophin(Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). The amino acids indicated herein correspond to amino acids of the wild type dystrophin being represented by SEQ ID NO: 55. Exon—skipping for the treatment of DMD is preferably but not exclusively directed to overcome a premature stop in the pre-mRNA by skipping an exon in the rod-domain shaped domain to correct the reading frame and allow synthesis of remainder of the dystrophin protein including the C-terminus, albeit that the protein is somewhat smaller as a result of a smaller rod domain. In a preferred embodiment, an individual having DMD and being treated using an oligonucleotide as defined herein will be provided a dystrophin, which exhibits at least to some extent an activity of a wild type dystrophin. More preferably, if said individual is a Duchenne patient or is suspected to be a Duchenne patient, a functional dystrophin is a dystrophin comparable in functionality to a dystrophin from an individual having BMD: preferably said dystrophin is able to interact with both actin and the DGC, but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). The central rod domain of wild type dystrophin comprises 24 spectrin-like repeats (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). For example, a central rod shaped domain of a dystrophin as provided herein may comprise 5 to 23, 10 to 22 or 12 to 18 spectrin-like repeats as long as it can bind to actin and to DGC.

Decreasing the production of an aberrant dystrophin in said patient or in a cell of said patient may be assessed at the mRNA level and preferably means that 99%, 90%, 80%, 70%, 60%, 50%, 40%, 30%, 20%, 10%, 5% or less of the initial amount of aberrant dystrophin mRNA, is still detectable by RT PCR. An aberrant dystrophin mRNA or protein is also referred to herein as a non-functional or less to non-functional or semi-functional dystrophin mRNA or protein. A non-functional pre-mRNA dystrophin is preferably leads to an out of frame dystrophin protein, which means that no dystrophin protein will be produced and/or detected. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein.

Increasing the production of a functional dystrophin in a patient or in a cell of said patient may be assessed at the mRNA level (by RT-PCR analysis) and preferably means that a detectable amount of a functional or in frame dystrophin mRNA is detectable by RT PCR. In another embodiment, 1%, 5%, 10%, 20%, 30%, 40%, 50%, 60%, 70%, 80%, 90% or more of the detectable dystrophin mRNA is a functional or in frame dystrophin mRNA.

Increasing the production of a functional dystrophin in a patient or in a cell of said patient may be assessed at the protein level (by immunofluorescence and western blot analyses) and preferably means that a detectable amount of a functional dystrophin protein is detectable by immunofluorescence or western blot analysis. In another embodiment, 1%, 5%, 10%, 20%, 30%, 40%, 50%, 60%, 70%, 80%, 90% or more of the detectable dystrophin protein is a functional dystrophin protein.

An increase or a decrease is preferably assessed in a muscular tissue or in a muscular cell of an individual or a patient by comparison to the amount present in said individual or patient before treatment with said molecule or composition of the invention. Alternatively, the comparison can be made with a muscular tissue or cell of said individual or patient, which has not yet been treated with said oligonucleotide or composition in case the treatment is local.

In a further aspect, there is provided a method for alleviating one or more symptom(s) of Duchenne Muscular Dystrophy or Becker Muscular Dystrophy in an individual or alleviate one or more characteristic(s) of a myogenic or muscle cell of said individual, the method comprising administering to said individual an oligonucleotide or a composition as defined herein.

There is further provided a method for enhancing, inducing or promoting skipping of an exon from a dystrophin pre-mRNA in a cell expressing said pre-mRNA in an individual suffering from Duchenne Muscular Dystrophy or Becker Muscular Dystrophy, the method comprising administering to said individual an oligonucleotide or a composition as defined herein.

Further provided is a method for increasing the production of a functional dystrophin protein and/or decreasing the production of an aberrant dystrophin protein in a cell, said cell comprising a pre-mRNA of a dystrophin gene encoding an aberrant dystrophin protein, the method comprising providing said cell with an oligonucleotide or composition of the invention and allowing translation of mRNA produced from splicing of said pre-mRNA. In one embodiment, said method is performed in vivo, for instance using a cell culture. Preferably, said method is in vivo in said individual.

In this context, increasing the production of a functional dystrophin protein has been defined herein.

Alleviating one or more symptom(s) of Duchenne Muscular Dystrophy or Becker Muscular Dystrophy in an individual using a molecule or a composition of the invention may be assessed by any of the following assays: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur at al (Manzur A Y et al, (2008), Glucocorticoid corticosteroids for Duchenne muscular dystrophy (review), Wiley publishers, The Cochrane collaboration.) gives an extensive explanation of each of these assays. For each of these assays, as soon as a detectable improvement or prolongation of a parameter measured in an assay has been found, it will preferably mean that one or more symptoms of Duchenne Muscular Dystrophy or Becker Muscular Dystrophy has been alleviated in an individual using a molecule or composition of the invention. Detectable improvement or prolongation is preferably a statistically significant improvement or prolongation as described in Hodgetts et al (Hodgetts S., et al, (2006), Neuromuscular Disorders, 16: 591-602).

Alternatively, the alleviation of one or more symptom(s) of Duchenne Muscular Dystrophy or Becker Muscular Dystrophy may be assessed by measuring an improvement of a characteristic of a muscle fiber relating to its function, integrity and/or survival, said characteristic being assessed on the patient self. Such characteristics may be assessed at the cellular, tissue level of a given patient. An alleviation of one or more characteristics may be assessed by any of the following assays on a myogenic cell or muscle cell from a patient: reduced calcium uptake by muscle cells, decreased collagen synthesis, altered morphology, altered lipid biosynthesis, decreased oxidative stress, and/or improved muscle fiber function, integrity, and/or survival. These parameters are usually assessed using immunofluorescence and/or histochemical analyses of cross sections of muscle biopsies.

An oligonucleotide as used herein preferably comprises an antisense oligonucleotide or antisense oligoribonucleotide. In a preferred embodiment an exon skipping technique is applied. Exon skipping interferes with the natural splicing processes occurring within a eukaryotic cell. In higher eukaryotes the genetic information for proteins in the DNA of the cell is encoded in exons which are separated from each other by intronic sequences. These introns are in some cases very long. The transcription machinery of eukaryotes generates a pre-mRNA which contains both exons and introns, while the splicing machinery, often already during the production of the pre-mRNA, generates the actual coding region for the protein by splicing together the exons present in the pre-mRNA.

Exon-skipping results in mature mRNA that lacks at least one skipped exon. Thus, when said exon codes for amino acids, exon skipping leads to the expression of an altered product. Technology for exon-skipping is currently directed towards the use of antisense oligonucleotides (AONs). Much of this work is done in the mdx mouse model for Duchenne muscular dystrophy. The mdx mouse carries a nonsense mutation in exon 23. Despite the mdx mutation, which should preclude the synthesis of a functional dystrophin protein, rare, naturally occurring dystrophin positive fibers have been observed in mdx muscle tissue. These dystrophin-positive fibers are thought to have arisen from an apparently naturally occurring exon-skipping mechanism, either due to somatic mutations or through alternative splicing. AONs directed to, respectively, the 3' and/or 5' splice sites of introns 22 and 23 in dystrophin pre-mRNA, have been shown to interfere with factors normally involved in removal of intron 23 so that also exon 23 was removed from the mRNA (Alter J, et al. Systemic delivery of morpholino oligonucleotide restores dystrophin expression bodywide and improves dystrophic pathology. Nat Med 2006; 12(2):175-7, Lu Q L, et al. Functional amounts of dystrophin produced by skipping the mutated exon in the mdx dystrophic mouse. Nat Med 2003; 6:6, Lu Q L, et al. Systemic delivery of antisense oligoribonucleotide restores dystrophin expression in body-wide skeletal muscles. Proc Natl Acad Sci USA 2005; 102(1):198-203, Mann C J, et al, Improved antisense oligonucleotide induced exon skipping in the mdx mouse model of muscular dystrophy. J Gene Med 2002; 4(6):644-54 or Graham I R, et al, Towards a therapeutic inhibition of dystrophin exon 23 splicing in mdx mouse muscle induced by antisense oligoribonucleotides (splicomers): target sequence optimisation using oligonucleotide arrays. J Gene Med 2004; 6(10):1149-58).

By the targeted skipping of a specific exon, a DMD phenotype is converted into a milder BMD phenotype. The skipping of an exon is preferably induced by the binding of AONs targeting exon-internal sequences. An oligonucleotide directed toward an exon internal sequence typically exhibits no overlap with non-exon sequences. It preferably does not overlap with the splice sites at least not insofar, as these are present in the intron. An oligonucleotide directed toward an exon internal sequence preferably does not contain a sequence complementary to an adjacent intron. Further provided is thus an oligonucleotide according to the invention, wherein said oligonucleotide, or a functional equivalent thereof, is for inhibiting inclusion of an exon of a dystrophin pre-mRNA into mRNA produced from splicing of said pre-mRNA. An exon skipping technique is preferably applied such that the absence of an exon from mRNA produced from dystrophin pre-mRNA generates a coding region for a more functional—albeit shorter—dystrophin protein. In this context, inhibiting inclusion of an exon preferably means that the detection of the original, aberrant dystrophin mRNA and/or protein is decreased as earlier defined herein.

Within the context of the invention, a functional equivalent of an oligonucleotide preferably means an oligonucleotide as defined herein wherein one or more nucleotides have been substituted and wherein an activity of said functional equivalent is retained to at least some extent. Preferably, an activity of said functional equivalent is providing a functional dystrophin protein. Said activity of said functional equivalent is therefore preferably assessed by quantifying the amount of a functional dystrophin protein or by quantifying the amount of a functional dystrophin mRNA. A functional dystrophin protein (or a functional dystrophin mRNA) is herein preferably defined as being a dystrophin protein (or a dystrophin protein encoded by said mRNA) able to bind actin and members of the DGC protein. The assessment of said activity of an oligonucleotide is preferably done by RT-PCR (m-RNA) or by immunofluorescence or Western blot analyses (protein). Said activity is preferably retained to at least some extent when it represents at least 50%, or at least 60%, or at least 70% or at least 80% or at least 90% or at least 95% or more of corresponding activity of said oligonucleotide the functional equivalent derives from. Such activity may be measured in a muscular tissue or in a muscular cell of an individual or in vitro in a cell by comparison to an activity of a corresponding oligonucleotide of said oligonucleotide the functional equivalent derives from. Throughout this application, when the word oligonucleotide is used it may be replaced by a functional equivalent thereof as defined herein.

In a preferred embodiment, an oligonucleotide of the invention, which comprises a sequence that binds and/or is complementary to a sequence of exon 44 of dystrophin pre-mRNA as earlier defined herein is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% or even more preferably at least 99%, or even more preferably 100%. In a most preferred embodiment, an oligonucleotide of the invention consists of a sequence that is complementary to part of dystrophin pre-mRNA as defined herein. As an example, an oligonucleotide may comprise a sequence that is complementary to part of dystrophin pre-mRNA as defined herein and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides. Preferably, additional flanking sequences are used to modify the binding of a protein to the oligonucleotide, or to modify a thermodynamic property of the oligonucleotide, more preferably to modify target RNA binding affinity.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridising to the complementary part. In this context, "sufficiently" preferably means that using a gel mobility shift assay as described in example 1 of EP 1 619 249, binding of an oligonucleotide is detectable. Optionally, said oligonucleotide may further be tested by transfection into muscle cells of patients. Skipping of the targeted exon may be assessed by RT-PCR (as described in EP 1 619 249). The complementary regions are preferably designed such that, when combined, they are specific for the exon in the pre-mRNA. Such specificity may be created with various lengths of complementary regions as this depends on the actual sequences in other (pre-)mRNA in the system. The risk that also one or more other pre-mRNA will be able to hybridise to the oligonucleotide decreases with increasing size of the oligonucleotide. It is clear that oligonucleotides comprising mismatches in the region of complementarity but that retain the capacity to hybridise and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridisation strengths, (i.e. increasing number of interactions with the opposing strand) are favourable in increasing the efficiency of the process of interfering with the splicing machinery of the system. Preferably, the complementarity is between 90 and 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides.

A preferred molecule of the invention comprises or consists of a nucleotide-based sequence that is antisense to a sequence selected from exon 44 of the DMD pre-mRNA. The sequence of the DMD pre-mRNA is preferably selected from SEQ ID NO 1: 5'-GUGGCUAACAGAAGCU; SEQ ID NO 2: 5'-GGGAACAUGCUAAAUAC, SEQ ID NO 3: 5'-AGACACAAAUUCCUGAGA, and SEQ ID NO 4: 5'-CUGUUGAGAAA.

A molecule of the invention is preferably an isolated molecule.

A molecule of the invention is preferably a nucleic acid molecule or a nucleotide-based molecule or an oligonucleotide or an antisense oligonucleotide which binds and/or is complementary to a sequence of exon 44 selected from SEQ ID NO:1, 2, 3 or 4.

A preferred molecule of the invention comprises or consists of from about 8 to about 60 nucleotides, more preferred from about 10 to about 50 nucleotides, more preferred from about 17 to about 40 nucleotides, more preferred from about 18 to about 30 nucleotides, more preferred from about 18 to about 24 nucleotides, most preferred about 20 nucleotides, such as 18 nucleotides, 19 nucleotides, 20 nucleotides, 21 nucleotides, 22 nucleotides or 23 nucleotides.

A preferred molecule of the invention comprises or consists of from 8 to 60 nucleotides, more preferred from 10 to 50 nucleotides, more preferred from 17 to 40 nucleotides, more preferred from 18 to 30 nucleotides, more preferred from 21 to 60, more preferred from 22 to 55, more preferred from 23 to 53, more preferred from 24 to 50, more preferred from 25 to 45, more preferred from 26 to 43, more preferred from 27 to 41, more preferred from 28 to 40, more preferred from 29 to 40, more preferred from 18 to 24 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In certain embodiments, the invention provides a molecule comprising or consisting of an antisense nucleotide sequence selected from the antisense nucleotide sequences depicted in Table 1A.

A molecule or nucleic acid molecule of the invention that binds and/or is complementary and/or is antisense to a nucleotide having nucleotide sequence: SEQ ID NO 1: 5'-GUGGCUAACAGAAGCU preferably comprises or consists of the antisense nucleotide sequence of SEQ ID NO 5; SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO:39, SEQ ID NO:41, SEQ ID NO:42, SEQ ID NO:49 or SEQ ID NO: 54. A preferred molecule that targets this region of the DMD pre-mRNA comprises or consists of the antisense nucleotide sequence of SEQ ID NO:5, SEQ ID NO 49, or SEQ ID NO 54. Most preferred oligonucleotide comprises or consists of the antisense nucleotide sequence of SEQ ID NO:5.

In a more preferred embodiment, the invention provides a molecule comprising or consisting of the antisense nucleotide sequence SEQ ID NO 5: 5'-UCAGCUUCUGUUAGC-CACUG. It was found that this molecule is very efficient in modulating splicing of exon 44 of the DMD gene in muscle cells. This preferred molecule of the invention comprising SEQ ID NO:5 comprises from 21 to 60, more preferred from 22 to 55, more preferred from 23 to 53, more preferred from 24 to 50, more preferred from 25 to 45, more preferred from 26 to 43, more preferred from 27 to 41, more preferred from 28 to 40, more preferred from 29 to 40, or preferably comprises or consists of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In another preferred embodiment, the invention provides a molecule comprising or consisting of the antisense nucleotide sequence SEQ ID NO 49 or 54. These preferred molecules of the invention comprising either SEQ ID NO:49 or SEQ ID NO:54 further comprise from 18 to 60, more preferred from 18 to 55, more preferred from 20 to 53, more preferred from 24 to 50, more preferred from 25 to 45, more preferred from 26 to 43, more preferred from 27 to 41, more preferred from 28 to 40, more preferred from 29 to 40, or preferably comprises or consists of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In a further embodiment, a molecule of the invention that is antisense to SEQ ID NO 2: 5'-GGGAACAUGCUAAAUAC preferably comprises or consists of the antisense nucleotide sequence of SEQ ID NO 43 or SEQ ID NO 44. These preferred molecules of the invention comprising either SEQ ID NO: 43 or SEQ ID NO:44, further comprise from 17 to 60 nucleotides, more preferred from 18 to 30 nucleotides, more preferred from 21 to 60, more preferred from 22 to 55, more preferred from 23 to 53, more preferred from 24 to 50, more preferred from 25 to 45, more preferred from 26 to 43, more preferred from 27 to 41, more preferred from 28 to 40, more preferred from 29 to 40, more preferred from 18 to 24 nucleotides, or preferably comprises or consists of 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In yet a further embodiment, a molecule of the invention that is antisense to SEQ ID NO 3: 5'-AGACACAAAUUC-CUGAGA preferably comprises or consists of the antisense nucleotide sequence of SEQ ID NO 47 or SEQ ID NO 48.

These preferred molecules of the invention comprising either SEQ ID NO:47 or SEQ ID NO:48 further comprise from 17 to 60 nucleotides, more preferred from 18 to 30 nucleotides, more preferred from 17 to 60, more preferred from 22 to 55, more preferred from 23 to 53, more preferred from 24 to 50, more preferred from 25 to 45, more preferred from 26 to 43, more preferred from 27 to 41, more preferred from 28 to 40, more preferred from 29 to 40, more preferred from 18 to 24 nucleotides, or preferably comprises or consists of 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In still a further embodiment, a molecule of the invention that is antisense to SEQ ID NO 4: 5'-CUGUUGAGAAA preferably comprises or consists of the antisense nucleotide sequence of SEQ ID NO 45 or SEQ ID NO 46. These preferred molecules of the invention comprising either SEQ ID NO:45 or SEQ ID NO:46 further comprise from 11 to 60 nucleotides, more preferred from 11 to 30 nucleotides, more preferred from 11 to 60, or preferably comprises or consists of 11, 12, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

A nucleotide sequence of a molecule of the invention may contain RNA residues, or one or more DNA residues, and/or one or more nucleotide analogues or equivalents, as will be further detailed herein below.

It is preferred that a molecule of the invention comprises one or more residues that are modified to increase nuclease resistance, and/or to increase the affinity of the antisense nucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10)alkyl, alkenyl, alkynyl, alkaryl, allyl, or aralkyl, that may be interrupted by one or more heteroatoms; O—, S—, or N-alkyl; O—, S—, or N-alkenyl; O—, S— or N-alkynyl; O—, S—, or N-allyl; O-alkyl-O-alkyl, -methoxy, -aminopropoxy; methoxyethoxy; -dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred antisense oligonucleotide according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

A most preferred antisense oligonucleotide according to the invention comprises a 2'-O-methyl phosphorothioate ribose.

It will also be understood by a skilled person that different antisense oligonucleotides can be combined for efficiently skipping of exon 44. In a preferred embodiment, a combination of at least two antisense oligonucleotides are used in a method of the invention, such as two different antisense oligonucleotides, three different antisense oligonucleotides, four different antisense oligonucleotides, or five different antisense oligonucleotides.

An antisense oligonucleotide can be linked to a moiety that enhances uptake of the antisense oligonucleotide in cells, preferably myogenic cells or muscle cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

A preferred antisense oligonucleotide comprises a peptide-linked PMO.

An oligonucleotide of the invention may be indirectly administrated using suitable means known in the art. An oligonucleotide may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of a molecule as identified herein. A cell can be provided with a molecule capable of interfering with essential sequences that result in highly efficient skipping of exon 44 by plasmid-derived antisense oligonucleotide expression or viral expression provided by adenovirus- or adeno-associated virus-based vectors. Expression is preferably driven by a polymerase III promoter, such as a U1, a U6, or a U7 RNA promoter. A preferred delivery vehicle is a viral vector such as an adeno-associated virus vector (AAV), or a retroviral vector such as a lentivirus vector (Goyenvalle A, et al. Rescue of dystrophic muscle through U7 snRNA-mediated exon skipping. Science 2004; 306(5702): 1796-9, De Angelis F G, et al. Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 2002; 99(14):9456-61 or Denti M A, et al. Chimeric adeno-associated virus/antisense U1 small nuclear RNA effectively rescues dystrophin synthesis and muscle function by local treatment of mdx mice. Hum Gene Ther 2006; 17(5):565-74) and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript (see the same Goyenvalle A et al, De Angelis F G et al or Denti M A et al). Such fusions may be generated as described (Gorman L, et al, Stable alteration of pre-mRNA splicing patterns by modified U7 small nuclear RNAs. Proc Natl Acad Sci U S A 1998; 95(9):4929-34 or Suter D, et al, Double-target antisense U7 snRNAs promote efficient skipping of an aberrant exon in three human beta-thalassemic mutations. Hum Mol Genet. 1999; 8(13):2415-23).

The oligonucleotide may be delivered as is. However, the oligonucleotide may also be encoded by the viral vector. Typically, this is in the form of an RNA transcript that comprises the sequence of the oligonucleotide in a part of the transcript.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of exon 44 of DMD.

A preferred AAV-based vector comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of an antisense oligonucleotide of the invention for inducing skipping of exon 44 of the DMD gene.

Improvements in means for providing an individual or a cell, tissue, organ of said individual with an oligonucleotide and/or an equivalent thereof, are anticipated considering the progress that has already thus far been achieved. Such future improvements may of course be incorporated to achieve the mentioned effect on restructuring of mRNA using a method of the invention. An oligonucleotide and/or an equivalent thereof can be delivered as is to an individual, a cell, tissue or organ of said individual. When administering an oligonucleotide and/or an equivalent thereof, it is preferred that an oligonucleotide and/or an equivalent thereof is dissolved in a solution that is compatible with the delivery method. Muscle or myogenic cells can be provided with a plasmid for antisense oligonucleotide expression by providing the plasmid in an aqueous solution. Alternatively, a plasmid can be provided by transfection using known transfection agentia. For intravenous, subcutaneous, intramuscular, intrathecal and/or intraventricular administration it is preferred that the solution is a physiological salt solution. Particularly preferred in the invention is the use of an excipient or transfection agentia that will aid in delivery of each of the constituents as defined herein to a cell and/or into a cell, preferably a muscle cell. Preferred are excipients or transfection agentia capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), lipofectin™, DOTAP and/or viral capsid proteins that are capable of self assembly into particles that can deliver each constituent as defined herein to a cell, preferably a muscle cell. Such excipients have been shown to efficiently deliver an oligonucleotide such as antisense nucleic acids to a wide variety of cultured cells, including muscle cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an oligonucleotide for use in the current invention to deliver it for the treatment of Duchenne Muscular Dystrophy or Becker Muscular Dystrophy in humans.

In addition, an oligonucleotide could be covalently or non-covalently linked to a targeting ligand specifically designed to facilitate the uptake in to the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an oligonucleotide is formulated in a composition or a medicament or a composition, which is provided with at least an excipient and/or a targeting ligand for delivery and/or a delivery device thereof to a cell and/or enhancing its intracellular delivery. Accordingly, the invention also encompasses a pharmaceutically acceptable composition comprising an oligonucleotide and further comprising at least one excipient and/or a targeting ligand for delivery and/or a delivery device of said oligonucleotide to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an oligonucleotide and a further adjunct compound as later defined herein.

A preferred oligonucleotide is for preventing or treating Duchenne Muscular Dystrophy (DMD) or Becker Muscular Dystrophy (BMD) in an individual. An individual, which may be treated using an oligonucleotide of the invention may already have been diagnosed as having a DMD or a BMD. Alternatively, an individual which may be treated using an oligonucleotide of the invention may not have yet been diagnosed as having a DMD or a BMD but may be an individual having an increased risk of developing a DMD or a BMD in the future given his or her genetic background. A preferred individual is a human being.

If required, a molecule or a vector expressing an antisense oligonucleotide of the invention can be incorporated into a pharmaceutically active mixture by adding a pharmaceutically acceptable carrier.

Therefore, the invention also provides a pharmaceutical composition comprising a molecule comprising an antisense oligonucleotide according to the invention, or a viral-based vector expressing the antisense oligonucleotide according to the invention.

In a further aspect, there is provided a composition comprising an oligonucleotide as defined herein. Preferably, said composition comprises at least two distinct oligonucleotides as defined herein. More preferably, these two distinct oligonucleotides are designed to skip one or two or more exons. Multi-skipping is encompassed by the present invention, wherein an oligonucleotide of the invention inducing the skipping of exon 44 is used in combination with another oligonucleotide inducing the skipping of another exon. In this context, another exon may be exon 43, 45 or 52. Multi exon skipping has been already disclosed in EP 1 619 249. The DMD gene is a large gene, with many different exons. Considering that the gene is located on the X-chromosome, it is mostly boys that are affected, although girls can also be affected by the disease, as they may receive a bad copy of the gene from both parents, or are suffering from a particularly biased inactivation of the functional allele due to a particularly biased X chromosome inactivation in their muscle cells. The protein is encoded by a plurality of exons (79) over a range of at least 2.4 Mb. Defects may occur in any part of the DMD gene. Skipping of a particular exon or particular exons can, very often, result in a restructured mRNA that encodes a shorter than normal but at least partially functional dystrophin protein. A practical problem in the development of a medicament based on exon-skipping technology is the plurality of mutations that may result in a deficiency in functional dystrophin protein in the cell. Despite the fact that already multiple different mutations can be corrected for by the skipping of a single exon, this plurality of mutations, requires the generation of a series of different pharmaceuticals as for different mutations different exons need to be skipped. An advantage of an oligonucleotide or of a composition comprising at least two distinct oligonucleotide as later defined herein capable of inducing skipping of two or more exons, is that more than one exon can be skipped with a single pharmaceutical. This property is not only practically very useful in that only a limited number of pharmaceuticals need to be generated for treating many different DMD or particular, severe BMD mutations. Another option now open to the person skilled in the art is to select particularly functional restructured dystrophin proteins and produce compounds capable of generating these preferred dystrophin proteins. Such preferred end results are further referred to as mild phenotype dystrophins.

In a preferred embodiment, said composition being preferably a pharmaceutical composition said pharmaceutical composition comprising a pharmaceutically acceptable carrier, adjuvant, diluent and/or excipient. Such a pharmaceutical composition may comprise any pharmaceutically acceptable carrier, filler, preservative, adjuvant, solubilizer, diluent and/or excipient is also provided. Such pharmaceutically acceptable carrier, filler, preservative, adjuvant, solubilizer, diluent and/or excipient may for instance be found in Remington: The Science and Practice of Pharmacy, 20th Edition. Baltimore, Md.: Lippincott Williams & Wilkins, 2000. Each feature of said composition has earlier been defined herein.

If several oligonucleotides are used, concentration or dose already defined herein may refer to the total concentration or dose of all oligonucleotides used or the concentration or dose of each oligonucleotide used or added. Therefore in one embodiment, there is provided a composition wherein each or the total amount of oligonucleotide used is dosed in an amount ranged between 0.5 mg/kg and 10 mg/kg.

The invention further provides the use of an antisense oligonucleotide according to the invention, or a viral-based vector that expresses an antisense oligonucleotide according to the invention, for modulating splicing of the DMD mRNA. The splicing is preferably modulated in human myogenic cells or muscle cells in vitro. More preferred is that splicing is modulated in human myogenic cells or muscle cells in vivo.

A preferred antisense oligonucleotide comprising one or more nucleotide analogs or equivalents of the invention modulates splicing in one or more muscle cells, including heart muscle cells, upon systemic delivery. In this respect, systemic delivery of an antisense oligonucleotide comprising a specific nucleotide analog or equivalent might result in targeting a subset of muscle cells, while an antisense oligonucleotide comprising a distinct nucleotide analog or equivalent might result in targeting of a different subset of muscle cells. Therefore, in one embodiment it is preferred to use a combination of antisense oligonucleotides comprising different nucleotide analogs or equivalents for modulating skipping of exon 44 of the DMD mRNA.

The invention furthermore provides the use of an antisense oligonucleotide according to the invention, or of a viral-based vector expressing the antisense oligonucleotide according to the invention, for the preparation of a medicament for the treatment of a DMD or BMD patient.

Therefore in a further aspect, there is provided the use of a oligoucleotide or of a composition as defined herein for the manufacture of a medicament for preventing or treating Duchenne Muscular Dystrophy or Becker Muscular Dystrophy in an individual. Each feature of said use has earlier been defined herein.

A treatment in a use or in a method according to the invention is at least one week, at least one month, at least several months, at least one year, at least 2, 3, 4, 5, 6 years or more. Each molecule or oligonucleotide or equivalent thereof as defined herein for use according to the invention may be suitable for direct administration to a cell, tissue and/or an organ in vivo of individuals affected by or at risk of developing DMD or BMD, and may be administered directly in vivo, ex vivo or in vitro. The frequency of administration of an oligonucleotide, composition, compound or adjunct compound of the invention may depend on several parameters such as the age of the patient, the mutation of the patient, the number of molecules (i.e. dose), the formulation of said molecule. The frequency may be ranged between at least once in two weeks, or three weeks or four weeks or five weeks or a longer time period.

Dose ranges of oligonucleotide according to the invention are preferably designed on the basis of rising dose studies in clinical trials (in vivo use) for which rigorous protocol requirements exist. A molecule or an oligonucleotide as defined herein may be used at a dose which is ranged between 0.1 and 20 mg/kg, preferably 0.5 and 10 mg/kg.

In a preferred embodiment, a concentration of an oligonucleotide as defined herein, which is ranged between 0.1 nM and 1 µM is used. Preferably, this range is for in vitro use in a cellular model such as muscular cells or muscular tissue. More preferably, the concentration used is ranged between 0.3 to 400 nM, even more preferably between 1 to 200 nM. If several oligonucleotides are used, this concentration or dose may refer to the total concentration or dose of oligonucleotides or the concentration or dose of each oligonucleotide added. The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimised any further.

An oligonucleotide as defined herein for use according to the invention may be suitable for administration to a cell, tissue and/or an organ in vivo of individuals affected by or at risk of developing DMD or BMD, and may be administered in vivo, ex vivo or in vitro. Said oligonucleotide may be directly or indirectly administered to a cell, tissue and/or an organ in vivo of an individual affected by or at risk of developing DMD or BMD, and may be administered directly or indirectly in vivo, ex vivo or in vitro. As Duchenne and Becker muscular dystrophy have a pronounced phenotype in muscle cells, it is preferred that said cells are muscle cells, it is further preferred that said tissue is a muscular tissue and/or it is further preferred that said organ comprises or consists of a muscular tissue. A preferred organ is the heart. Preferably, said cells comprise a gene encoding a mutant dystrophin protein. Preferably, said cells are cells of an individual suffering from DMD or BMD.

Unless otherwise indicated each embodiment as described herein may be combined with another embodiment as described herein.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

The expression "in vivo" as used herein may mean in a cellular system which may be isolated from the organism the cells derive from. Preferred cells are muscle cells. In vivo may also mean in a tissue or in a multicellular organism which is preferably a patient as defined herein. Through out the invention, in vivo is opposed to in vitro which is generally associated with a cell free system.

All patent and literature references cited in the present specification are hereby incorporated by reference in their entirety. Each embodiment as identified herein may be combined together unless otherwise indicated.

The invention is further explained in the following examples. These examples do not limit the scope of the invention, but merely serve to clarify the invention.

FIGURE LEGENDS

FIG. 1. Evaluation of AONs designed to induce the skipping of exon 44 from the DMD gene in transfected muscle cells from healthy control or a DMD patient with an exon 45 deletion.
(A) In differentiated muscle cells (myotubes) from a patient with an exon 45 deletion, all tested (transfected) AONs induced exon 44 skipping at a concentration of 150 nM, with PS188 (SEQ ID NO:5), PS190 (previously published as h44AON2; Aartsma-Rus et al. Neuromuscul Disord 2002; 12 Suppl: S71), PS191 (SEQ ID NO: 47), PS193 (SEQ ID NO: 48), PS194 (SEQ ID NO: 46), and PS196 (SEQ ID NO: 51) demonstrating highest efficiencies (between 84% and 94%).
(B) The majority of AONs was also tested by transfection into healthy human control cells at 150 and 400 nM concentrations. The results are summarized in this column chart. PS188 (SEQ ID NO:5), PS190, PS191 (SEQ ID NO: 47), PS193 (SEQ ID NO: 48), PS194 (SEQ ID NO: 46), and PS196 (SEQ ID NO: 51) were confirmed to be most efficient in inducing exon 44 skipping. Note that the exon 44 skipping levels in patient cells are typically higher than in control cells as a result of the fact that, in contrast to healthy cells, in patient cells exon 44 skipping is frame-restoring and giving rise to a more functional and stable. No exon 44 skipping was observed in non-transfected muscle cells in all experiments (data not shown).
(C) Examples of PS197 (SEQ ID NO 52) and three additional AONs, PS199 (SEQ ID NO 44), PS200 (SEQ ID NO 49), and PS201 (SEQ ID NO 50), similarly tested in control muscle cells, at transfection concentrations 150 nM and 400 nM. The exon 44 skipping percentages varied between 1% (PS199) and 44% (PS200). M: DNA size marker (100 by ladder).

FIG. 2. Further evaluation of PS188 (SEQ ID NO:5) by transfection of human control muscle cells or peripheral blood mononuclear cells (PB-MNCs).
(A) Dose-response experiment. In human control muscle cells, PS188 showed increasing levels of exon 44 skipping at transfection doses increasing from 50 nM to 400 nM (in triplo), up to 45% at 400 nM.
(B) PB-MNCs of a healthy individual were transfected with 200 nM PS188. Despite the fact that dystrophin is only expressed at low levels in this type of cells, exon 44 skipping was clearly observed. These results confirm the efficiency of PS188 in inducing exon 44 skipping from the DMD gene. M: DNA size marker.

FIG. 3. Further evaluation of PS188 (SEQ ID NO:5) by administration to transgenic hDMD mice expressing the full length human DMD gene, and to cynomolgus monkeys included in extensive toxicity studies.
(A) Following intramuscular injection of 2×40 μg PS188 into both gastrocnemius muscles (G1 and G2) of an hDMD mouse, exon 44 skipping was observed, albeit at low levels. This confirms the capacity of PS188 to induce human exon 44 skipping in muscle tissue in vivo. The low levels were expected given the fact that this mouse model has healthy muscle fibers typically showing lower levels of AON uptake when compared to dystrophic muscle fibers. NT: in non-treated hDMD muscle no exon 44 skipping was observed. M: DNA size marker
(B) In monkeys included in toxicity studies on PS188, exon 44 skipping was observed in peripheral blood mononuclear cells (PB-MNCs) after 1-hour intravenous infusions every fourth day for 29 days at a dose-level of 6 mg/kg PS188. No exon 44 skipping was observed in non-treated monkeys (NT). M: DNA size marker.

EXAMPLES

Example 1

Material and Methods

AON design was based on (partly) overlapping open secondary structures of the target exon RNA as predicted by the m-fold program (Mathews et al., J Mol Biol 1999; 288(5): 911-40), on (partly) overlapping putative SR-protein binding sites as predicted by the ESE-finder software (rulai.cshl.edu/tools/ESE/) (Cartegni et al., Nucleic Acids Res 2003; 31(13): 3568-71), and on avoiding G-stretches of 3 or more nucleotides or CpG pairs. AONs (see Table 1) were synthesized by Eurogentec (Belgium) and Prosensa Therapeutics BV (Leiden, Netherlands), and contain 2'-O-methyl RNA and full-length phosphorothioate backbones.

Tissue Culturing, Transfection and RT-PCR Analysis

Myotube cultures derived from a healthy individual ("human control") or a DMD patient with an exon 45 deletion were processed as described previously (Aartsma-Rus et al. Hum Mol Genet. 2003; 12(8): 907-14; Havenga et al. J Virol 2002; 76(9): 4612-20). For the screening of AONs, myotube cultures were transfected with 150 and/or 400 nM of each AON. Transfection reagent polyethylenimine (PEI, ExGen500 MBI Fermentas) or a derivative (UNIFectylin, Prosensa Therapeutics BV, Netherlands) was used, with 2 μl ExGen500 or UNIFectylin per μg AON. A control AON with a fluorescein label was used to confirm optimal transfection efficiencies (typically over 90% fluorescent nuclei were obtained). RNA was isolated 24 to 48 hours after transfection as described (Aartsma-Rus et al. Neuromuscul Disord 2002; 12 Suppl: S71). Exon skipping efficiencies were determined by nested RT-PCR analysis using primers in the exons flanking exon 44 (Aartsma-Rus et al. Neuromuscul Disord 2002; 12 Suppl: S71). PCR fragments were isolated from agarose gels (using the QIAquick Gel Extraction Kit (QIAGEN) for sequence verification (by the Leiden Genome Technology Center (LGTC) using the BigDye Terminator Cycle Sequencing Ready Reaction kit (PE Applied Biosystems), and ABI 3700 Sequencer (PE Applied Biosystems). For quantification, the PCR products were analyzed using the DNA 1000 LabChips Kit on the Agilent 2100 bioanalyzer (Agilent Technologies, USA).

Results

A series of AONs targeting sequences within exon 44 were designed and tested both in healthy control and patient-derived myotube cultures, by transfection and subsequent RT-PCR and sequence analysis of isolated RNA. In myotubes derived from a DMD patient with a deletion of exon 45, specific exon 44 skipping was induced at 150 nM for every AON(PS187 to PS201) tested, with PS188 (SEQ ID NO:5), PS190 (previously published as h44AON2, Aartsma-Rus et al. Neuromuscul Disord 2002; 12 Suppl: S71), PS191 (SEQ ID NO: 47), PS193 (SEQ ID NO: 48), PS194 (SEQ ID NO: 46), and PS196 (SEQ ID NO: 51) demonstrating highest levels of skipping (between 84% and 94% at 150 nM) (FIG. 1A).

Similar transfection experiments were done in control cells from a healthy individual. Percentages of exon 44 skipping were assessed and compared to those in the patient cell cultures (FIG. 1B). Inherent to nonsense-mediated RNA decay of the control transcript after exon 44 skipping, the control percentages were typically lower than those in the patient cells (see for instance results with PS197 in FIG. 1A (patient cells) vs FIG. 1C (control cells)).

Three additional AONs (PS199 (SEQ ID NO 44), PS200 (SEQ ID NO 49), and PS201 (SEQ ID NO 50) were tested in control muscle cells, at concentrations of 150 nM and 400 nM. The exon 44 skipping percentages varied between 1% (PS199) and 44% (PS200) (FIG. 1C). Based on all transfection experiments, the AONs PS187, PS188, PS190, PS191, PS192, PS193, PS194, PS196 and PS200 were considered most efficient, and AONs PS189, PS197, PS198, PS199, and PS201 least efficient.

PS188 (SEQ ID NO 5) was further tested in dose-response experiments in healthy human control muscle cells, applying increasing doses from 50 to 400 nM in triplo. Increasing levels of exon 44 skipping were accordingly observed, up to 45% at 400 nMPS188 (FIG. 2A).

Example 2

Materials and Methods

A fresh healthy human control blood sample, collected in an EDTA tube, was layered on top of a HistoPaque gradient. Upon centrifugation, the second layer (of the four layers, from top to bottom) with the mononuclear cells was collected, washed, and centrifuged again. The cell pellet was resuspended in proliferation culturing medium and counted. In a 6-wells plate, $8 \times 10^6$ cells per well were plated and incubated at 37° C., 5% $CO_2$ for 3 hrs. The cells were then transfected with 0 or 200 nM PS188 (SEQ ID NO:5; 2'OMePS RNA; Prosensa Therapeutics BV), in duplo, per dish. RNA was isolated 72 hrs after transfection, and analysed by RT-PCR analysis using DMD-gene specific primers flanking exon 44 (Aartsma-Rus et al. Neuromuscul Disord 2002; 12 Suppl: S71). Sequence analysis (by the Leiden Genome Technology Center (LGTC) using the BigDye Terminator Cycle Sequencing Ready Reaction kit (PE Applied Biosystems), and ABI 3700 Sequencer (PE Applied Biosystems) was performed on isolated PCR products (using the QIAquick Gel Extraction Kit (QIAGEN) to confirm the specific exon 44 skipping on RNA level.

Results

Figure 2B:
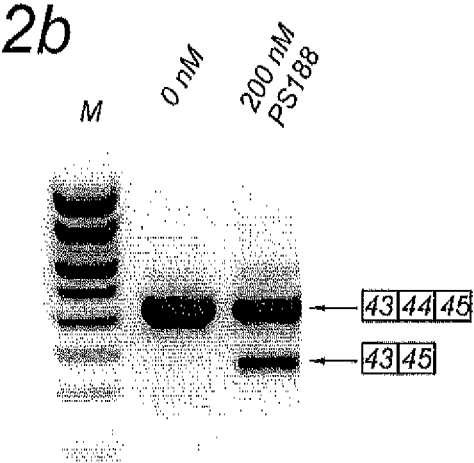

In transfected peripheral blood mononuclear cells (PB-MNCs) from a healthy control individual, PS188 induced the production of a novel shorter transcript fragment when applied at 200 nM (FIG. 2B). This fragment was isolated an sequenced and confirmed due to the specific skipping of exon 44. In non-transfected PB-MNCs no exon 44 skipping was observed. These results indicate that PS188 is an efficient compound inducing human exon 44 skipping in vitro.

Example 3

Materials and Methods
Antisense Oligoribonucleotides (AONs).

Normal and mdx mice (Sicinski et al. (1989). Science 244: 1578-1580) were injected with the mouse-specific m46AON4 (van Deutekom et al. (2001) Hum Mol Genet. 10: 1547-1554), whereas the hDMD mice with the human-specific PS196 (SEQ ID NO 51) or PS188 (SEQ ID NO 5). Both AONs contained a full-length phosphorothioate backbone and 2'-O-methyl modified ribose molecules (PS196: Eurogentec, Belgium; PS188: Prosensa Therapeutics BV).
Normal, mdx and Transgenic hDMD Mice Normal mice (C57B1/6NCrL) and mdx mice (C57B1/10ScSn-mdx/J) were obtained from Charles River Laboratories (The Netherlands). Transgenic hDMD mice were engineered in our own LUMC laboratories. Briefly, embryonic stem (ES) cells were genetically modified through fusions with yeast spheroplasts carrying a YAC of 2.7 Mb that contained the full-length (2.4 Mb) human DMD gene. This YAC was previously reconstructed by homologous recombination of smaller overlapping YACs in yeast (Den Dunnen et al. (1992). Hum Mol Genet. 1: 19-28). ES-cells showing integration of one copy of the full-size YAC, as assessed by PFGE mapping, exon-PCR analysis across the entire gene, and metaphase FISH analysis, were then used to generate homozygous hDMD mice ('t Hoen et al., J. Biol. Chem. 2008). Transgenic hDMD mice do not appear to be physically affected by the genetic modification. Appropriate expression of the human DMD gene could be demonstrated in muscle, both at RNA and protein level. The engineering of these mice was authorised by the Dutch Ministry of Agriculture (LNV); project nr. VVA/BD01.284 (E21).
Administration of AONs.

The experiments on intramuscular AON-injections in mice were authorised by the animal experimental commission (UDEC) of the Medical Faculty of the Leiden University (project no. 00095, 03027). AONs were injected, either pure, or complexed to the cationic polymer polyethylenimine (PEI; ExGen 500 (20×), MBI Fermentas) at ratios of 1 ml PEI per nmol AON in a 5% w/v glucose solution, or to 15 nmol SAINT-18™ (Synvolux Therapeutics B.V., The Netherlands), according to the manufacturers' instructions. The SAINT-18™ delivery system is based on a cationic pyridinium head group and allows non-toxic delivery of antisense oligonucleotides. Mice were anaesthetised by intraperitoneal injection of a 1:1 (v/v) Hypnorm/Dormicum solution (Janssen Pharmaceutica, Belgium/Roche, The Netherlands). Pure AON(PS188) was administered in a final injection volume of 40 ml by intramuscular injection into both gastrocnemius muscles of the mice using a Hamilton syringe with a 22-Gauge needle. The mice received two injections of 40 mg at a 24 h interval. They were sacrificed at different time-points post-injection; for PS188-injected hDMD mice ten days after the last injection. Muscles were isolated and frozen in liquid nitrogen-cooled 2-methylbutane.
RT-PCR Analysis.

Muscle samples were homogenized in RNA-Bee solution (Campro Scientific, The Netherlands). Total RNA was isolated and purified according to the manufacturer's instructions. For cDNA synthesis with the reverse transcriptase C. therm polymerase or Transcriptor (Roche Diagnostics, The Netherlands), 300 ng of RNA was used in a 20 •l reaction at 60° C. for 30 min, reverse primed with either mouse- or human-specific primers. First PCRs were performed with outer primer sets (flanking exons 43-45 for PS188-injected mice), for 20 cycles of 94° C. (40 sec), 60° C. (40 sec), and 72° C. (60 sec). One ml of this reaction (diluted 1:10) was then re-amplified using nested primer combinations in the exons directly flanking the target exon (exon 44 for PS188-injected mice), with 30 cycles of 94° C. (40 sec), 60° C. (40 sec), and 72° C. (60 sec). PCR products were analysed on 2% agarose gels. Skipping efficiencies were determined by quantification of PCR products using the DNA 1000 LabChip® Kit and the Agilent 2100 bioanalyzer (Agilent Technologies, The Netherlands). Primer sets and sequences were described previously (Aartsma-Rus et al. (2002) Neuromuscul Disord 12 Suppl: S71.8,17; van Deutekom et al. (2001) Hum Mol Genet. 10: 1547-1554).

Sequence Analysis.

RT-PCR products were isolated from 2% agarose gels using the QIAquick Gel Extraction Kit (QIAGEN). Direct DNA sequencing was carried out by the Leiden Genome Technology Center (LGTC) using the BigDye Terminator Cycle Sequencing Ready Reaction kit (PE Applied Biosystems), and analyzed on an ABI 3700 Sequencer (PE Applied Biosystems).

MALDI-TOF Mass-spectrometry.

RNA-Bee muscle homogenates were purified using a nucleic acid purification kit (Nucleic Acid Purification Kit for Sequazyme™ Pinpoint SNP Kit, Applied Biosystems) with 96 well spin plates (Applied Biosystems) following the manufacturer's instructions. Matrix solution (50 mg/ml 3-hydroxy picolinic acid and 25 mM dibasic ammonium citrate in 50% acetonitrile) was applied in 1 ml aliquots to an Anchor Chip™ sample target (Bruker Daltonics, Germany) and air-dried. Samples were spotted in 0.5 ml aliquots onto the matrix crystals and air-dried. Mass determinations were performed on a Reflex III MALDI-TOF mass-spectrometer (Bruker Daltonics, Germany). Spectra were acquired in reflector mode and accumulated for approximately 900 laser shots. Samples of labelled and unlabelled m46AON4 were analyzed for comparison.

Results

Exon Skipping in Wild-type Muscle

We first set up targeted exon skipping in mouse muscle in vivo and optimised different parameters of administration. Initial experiments were performed in wild type mice, and, while nonsense-mediated RNA decay will cause underestimation of the exon skipping efficiencies, the effect of the AONs was monitored on mRNA level only. We injected increasing dosages from 0.9 nmol to 5.4 nmol of each antisense oligonucleotide. RT-PCR analysis of total muscle RNA demonstrated the occurrence of a novel shorter transcript fragment in all samples injected. Sequence analysis confirmed the precise skipping of exon 44 in this product (data not shown).

Cross-sections of the contra-lateral injected muscles were analysed for dispersion and persistence of a fluorescein-labelled control AON. Following injection of pure AON, we observed fluorescent signals within some fibres for up to one week. At later time points only weak signals were observed, and mainly within the interstitial spaces. The use of PEI clearly enhanced both dispersion and persistence of the fluorescent signal, even after 3 weeks. However, it also induced fibre degeneration and monocyte infiltration absorbing most fluorescence. Using SAINT, most of the signal was detected in the interstitial spaces for up to one week, indicating that this reagent did not efficiently deliver the AON into the muscle fibres. Since the fluorescent signal may not correspond to the presence of intact and functional AONs, we performed MALDI-TOF mass-spectrometry of injected muscle samples. The analyses indicated that the fluorescent label was removed from the AON within 24 hours. The labelled AON was only detectable for up to two weeks when using PEI. The interstitial AONs were probably more vulnerable to degradation than the intracellular AONs. The unlabelled AON was observed for three to four weeks post-injection in all three series, but it may only be functional when present intracellularly, i.e. in the PEI series.

Human-specific Exon Skipping in hDMD Muscle

Figure 3A:
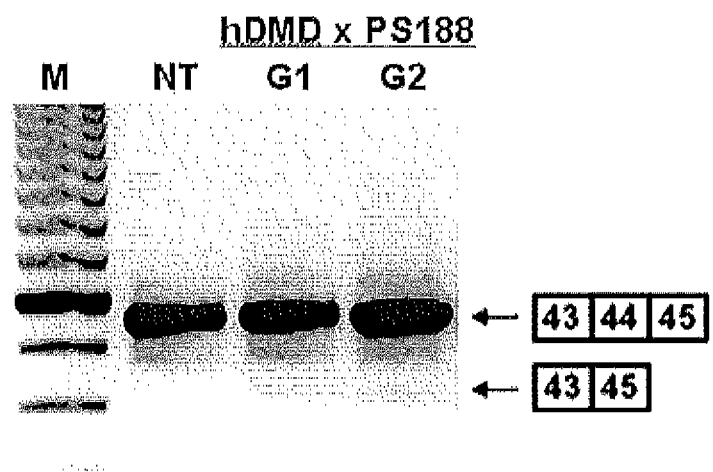
Figure 3B:
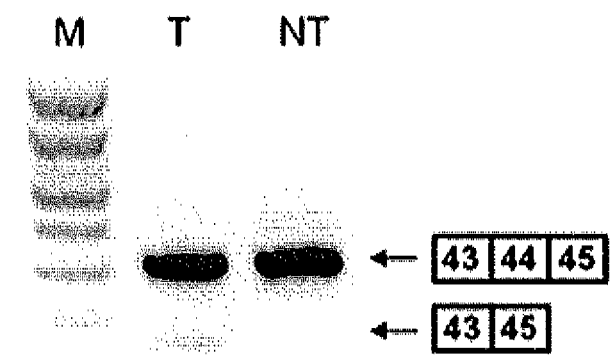

Since the exon skipping strategy is a sequence-specific therapeutic approach, the ideal pre-clinical validation would be a target human DMD gene, in a mouse experimental background. We have engineered such transgenic, "humanised" DMD (hDMD) mice carrying an integrated and functional copy of the full-length human DMD gene. Expression of human dystrophin in hDMD mouse muscle was specifically detected by immunohistochemical analysis of cross-sections, using a human-specific antibody (MANDYS106). On muscle RNA level, RT-PCR analyses using either mouse- or human-specific primers demonstrated correct transcription of the human DMD gene. Furthermore, upon crossing with mdx mice, the hDMD construct showed to complement the dystrophic defect, as was assessed by histological and cDNA microarray analysis ('t Hoen et al., J. Biol. Chem. 2008). hDMD mice have healthy muscle fibers typically exhibiting a limited uptake of naked AONs. We injected the human-specific AON PS196 (SEQ ID NO 51) complexed to PEI, or PS188 (SEQ ID NO 5) without PEI, into the gastrocnemius muscles of the hDMD mice (2×40 µg injections within 24 hrs). At 7 to 10 days post-injection we clearly observed the skipping of the targeted exon 44 from the human DMD transcript (FIG. 3A). Although the human-specific AONs are highly homologous to the corresponding mouse sequences, with only 2 or 3 mismatches in the respective 20-mers, the mouse endogenous transcripts were not affected to any detectable level. PS188 induced exon 44 skipping, as confirmed by sequence analysis. No exon 44 skipping was observed in non-treated hDMD muscle. These results indicate that PS188 is an efficient compound inducing human exon 44 skipping in muscle tissue.

Example 4

Material and Methods

As part of an extensive toxicity program for PS188, non-fasted cynomolgus monkeys were treated by 1-hour intravenous infusion (5 mL/kg/h) every fourth day for 29 days at the dose-level of 6 mg/kg PS188 (SEQ ID NO 5; 2'OMePS RNA; Agilent Life Sciences, USA). The PS188 formulations were freshly prepared on each treatment day (on test days 1, 5, 9, 13, 17, 21, 25 and 29) shortly before initiation of the administration (as soon as possible before, at the most within one hour before start of administration). Formulations were prepared by dissolving PS188 in phosphate buffer; the purity and water content were taken into account as provided in the Certificate of Analysis of the drug substance. The amount of PS188 was adjusted to each animal's current body weight. The animals were sacrificed 96 hours after the last administration (day 33). Whole blood samples (10 ml) were collected in EDTA tubes, and (after overnight shipment at room temperature) layered on top of a HistoPaque gradient. Upon centrifugation, the second layer (of the four layers, from top to bottom) with the mononuclear cells was collected, washed, and centrifuged again. RNA was isolated from the resulting cell pellet and analysed by RT-PCR analysis using DMD-gene specific primers flanking exon 44 (Aartsma-Rus et al.

Neuromuscul Disord 2002; 12 Suppl: S71). Sequence analysis (by the Leiden Genome Technology Center (LGTC) using the BigDye Terminator Cycle Sequencing Ready Reaction kit (PE Applied Biosystems), and ABI 3700 Sequencer (PE Applied Biosystems) was performed on isolated PCR products (using the QIAquick Gel Extraction Kit (QIAGEN) to confirm the specific exon 44 skipping on RNA level.

Results

In monkeys treated by 1-hour intravenous infusions every fourth day for 29 days at the dose-level of 6 mg/kg PS188, exon 44 skipping was observed in peripheral blood mononuclear cells (FIG. 3B), despite the fact that these cells express only low levels of dystrophin. The human and monkey DMD sequence targeted by PS188 is in fact 100% identical. No exon 44 skipping was observed in non-treated monkeys. These results indicate that PS188 is an efficient compound inducing exon 44 skipping in vivo.

TABLE 1

Antisense oligonucleotide sequences.

Table 1A

| | | |
|---|---|---|
| 1 (PS188) | UCAGCUUCUGUUAGCCACUG | SEQ ID NO 5 |
| 2 | UUCAGCUUCUGUUAGCCACU | SEQ ID NO 6 |
| 3 | UUCAGCUUCUGUUAGCCACUG | SEQ ID NO 7 |
| 4 | UCAGCUUCUGUUAGCCACUGA | SEQ ID NO 8 |
| 5 | UUCAGCUUCUGUUAGCCACUGA | SEQ ID NO 9 |
| 6 | UCAGCUUCUGUUAGCCACUGA | SEQ ID NO 10 |
| 7 | UUCAGCUUCUGUUAGCCACUGA | SEQ ID NO 11 |
| 8 | UCAGCUUCUGUUAGCCACUGAU | SEQ ID NO 12 |
| 9 | UUCAGCUUCUGUUAGCCACUGAU | SEQ ID NO 13 |
| 10 | UCAGCUUCUGUUAGCCACUGAUU | SEQ ID NO 14 |
| 11 | UUCAGCUUCUGUUAGCCACUGAUU | SEQ ID NO 15 |
| 12 | UCAGCUUCUGUUAGCCACUGAUUA | SEQ ID NO 16 |
| 13 | UUCAGCUUCUGUUAGCCACUGAUA | SEQ ID NO 17 |
| 14 | UCAGCUUCUGUUAGCCACUGAUUAA | SEQ ID NO 18 |
| 15 | UUCAGCUUCUGUUAGCCACUGAUUAA | SEQ ID NO 19 |
| 16 | UCAGCUUCUGUUAGCCACUGAUUAAA | SEQ ID NO 20 |
| 17 | UUCAGCUUCUGUUAGCCACUGAUUAAA | SEQ ID NO 21 |
| 18 | CAGCUUCUGUUAGCCACUG | SEQ ID NO 22 |
| 19 | CAGCUUCUGUUAGCCACUGAU | SEQ ID NO 23 |
| 20 | AGCUUCUGUUAGCCACUGAUU | SEQ ID NO 24 |
| 21 | CAGCUUCUGUUAGCCACUGAUU | SEQ ID NO 25 |
| 22 | AGCUUCUGUUAGCCACUGAUUA | SEQ ID NO 26 |
| 23 | CAGCUUCUGUUAGCCACUGAUUA | SEQ ID NO 27 |

TABLE 1-continued

Antisense oligonucleotide sequences.

| | | |
|---|---|---|
| 24 | AGCUUCUGUUAGCCACUGAUUAA | SEQ ID NO 28 |
| 25 | CAGCUUCUGUUAGCCACUGAUUAA | SEQ ID NO 29 |
| 26 | AGCUUCUGUUAGCCACUGAUUAAA | SEQ ID NO 30 |
| 27 | CAGCUUCUGUUAGCCACUGAUUAAA | SEQ ID NO 31 |
| 28 | AGCUUCUGUUAGCCACUGAUUAAA | SEQ ID NO 32 |
| 29 | AGCUUCUGUUAGCCACUGAU | SEQ ID NO 33 |
| 30 | GCUUCUGUUAGCCACUGAUU | SEQ ID NO 34 |
| 31 | AGCUUCUGUUAGCCACUGAUU | SEQ ID NO 35 |
| 32 | GCUUCUGUUAGCCACUGAUUA | SEQ ID NO 36 |
| 33 | AGCUUCUGUUAGCCACUGAUUA | SEQ ID NO 37 |
| 34 | GCUUCUGUUAGCCACUGAUUAA | SEQ ID NO 38 |
| 35 | AGCUUCUGUUAGCCACUGAUUAA | SEQ ID NO 39 |
| 36 | GCUUCUGUUAGCCACUGAUUAAA | SEQ ID NO 40 |
| 37 | AGCUUCUGUUAGCCACUGAUUAAA | SEQ ID NO 41 |
| 38 | GCUUCUGUUAGCCACUGAUUAAA | SEQ ID NO 42 |
| 39 (PS 192) | CCAUUUGUAUUUAGCAUGUUCCC | SEQ ID NO 43 |
| 40 (PS 199) | AGAUACCAUUUGUAUUUAGC | SEQ ID NO 44 |
| 41 (PS 187) | GCCAUUUCUCAACAGAUCU | SEQ ID NO 45 |
| 42 (PS 194) | GCCAUUUCUCAACAGAUCUGUCA | SEQ ID NO 46 |
| 43 (PS 191) | AUUCUCAGGAAUUUGUGUCUUUC | SEQ ID NO 47 |
| 44 (PS 193) | UCUCAGGAAUUUGUGUCUUUC | SEQ ID NO 48 |
| 45 (PS 200) | GUUCAGCUUCUGUUAGCC | SEQ ID NO 49 |
| 46 (PS 201) | CUGAUUAAAUAUCUUUAUAU C | SEQ ID NO 50 |

Table 1B

| | | |
|---|---|---|
| 47 (PS196) | GCCGCCAUUUCUCAACAG | SEQ ID NO 51 |
| 48 (PS 197) | GUAUUUAGCAUGUUCCCA | SEQ ID NO 52 |
| 49 (PS 198) | CAGGAAUUUGUGUCUUUC | SEQ ID NO 53 |
| 50 (PS189) | UCUGUUAGCCACUGAUUAAAU | SEQ ID NO 54 |

SEQ ID NO:55 *Homo sapiens* DMD Amino Acid Sequence

MLWWEEVEDCYEREDVQKKTFTKWVNAQFSKFGKQHIENLFSDLQDGRRLLDLLEGLTG

QKLPKEKGSTRVHALNNVNKALRVLQNNNVDLVNIGSTDIVDGNHKLTLGLIWNIILHWQ

-continued

VKNVMKNIMAGLQQTNSEKILLSWVRQSTRNYPQVNVINFTTSWSDGLALNALIHSHRPDL

FDWNSVVCQQSATQRLEHAFNIARYQLGIEKLLDPEDVDTTYPDKKSILMYITSLFQVLPQQ

VSIEAIQEVEMLPRPPKVTKEEHFQLHHQMHYSQQITVSLAQGYERTSSPKPRFKSYAYTQ

AAYVTTSDPTRSPFPSQHLEAPEDKSFGSSLMESEVNLDRYQTALEEVLSWLLSAEDTLQA

QGEISNDVEVVKDQFHTHEGYMMDLTAHQGRVGNILQLGSKLIGTGKLSEDEETEVQEQM

NLLNSRWECLRVASMEKQSNLHRVLMDLQNQKLKELNDWLTKTEERTRKMEEEPLGPDL

EDLKRQVQQHKVLQEDLEQEQVRVNSLTHMVVVVDESSGDHATAALEEQLKVLGDRWAN

ICRWTEDRWVLLQDILLKWQRLTEEQCLFSAWLSEKEDAVNKIHTTGFKDQNEMLSSLQK

LAVLKADLEKKKQSMGKLYSLKQDLLSTLKNKSVTQKTEAWLDNFARCWDNLVQKLEKS

TAQISQAVTTTQPSLTQTTVMETVTTVTTREQILVKHAQEELPPPPPQKKRQITVDSEIRKRL

DVDITELHSWITRSEAVLQSPEFAIFRKEGNFSDLKEKVNAIEREKAEKFRKLQDASRSAQA

LVEQMVNEGVNADSIKQASEQLNSRWIEFCQLLSERLNWLEYQNNIIAFYNQLQQLEQMT

TTAENWLKIQPTTPSEPTAIKSQLKICKDEVNRLSGLQPQIERLKIQSIALKEKGQGPMFLDA

DFVAFTNHFKQVFSDVQAREKELQTIFDTLPPMRYQETMSAIRTWVQQSETKLSIPQLSVT

DYEIMEQRLGELQALQSSLQEQQSGLYYLSTTVKEMSKKAPSEISRKYQSEFEEIEGRWKK

LSSQLVEHCQKLEEQMNKLRKIQNHIQTLKKWMAEVDVFLKEEWPALGDSEILKKQLKQC

RLLVSDIQTIQPSLNSVNEGGQKIKNEAEPEFASRLETELKELNTQWDHMCQQVYARKEAL

KGGLEKTVSLQKDLSEMHEWMTQAEEEYLERDFEYKTPDELQKAVEEMKRAKEEAQQKE

AKVKLLTESVNSVIAQAPPVAQEALKKELETLTTNYQWLCTRLNGKCKTLEEVWACWHEL

LSYLEKANKWLNEVEFKLKTTENIPGGAEEISEVLDSLENLMRHSEDNPNQIRILAQTLTD

GGVMDELINEELETFNSRWRELHEEAVRRQKLLEQSIQSAQETEKSLHLIQESLTFIDKQLA

AYIADKVDAAQMPQEAQKIQSDLTSHEISLEEMKKHNQGKEAAQRVLSQIDVAQKKLQDV

SMKFRLFQKPANFEQRLQESKMILDEVKMHLPALETKSVEQEVVQSQLNHCVNLYKSLSE

VKSEVEMVIKTGRQIVQKKQTENPKELDERVTALKLHYNELGAKVTERKQQLEKCLKLSR

KMRKEMNVLTEWLAATDMELTKRSAVEGMPSNLDSEVAWGKATQKEIEKQKVHLKSITE

VGEALKTVLGKKETLVEDKLSLLNSNWIAVTSRAEEWLNLLLEYQKHMETFDQNVDHITK

WIIQADTLLDESEKKKPQQKEDVLKRLKAELNDIRPKVDSTRDQAANLMANRGDHCRKLV

EPQISELNHRFAAISHRIKTGKASIPLKELEQFNSDIQKLLEPLEAEIQQGVNLKEEDFNKD

MNEDNEGTVKELLQRGDNLQQRITDERKREEIKIKQQLLQTKHNALKDLRSQRRKKALEIS

HQWYQYKRQADDLLKCLDDIEKKLASLPEPRDERKIKEIDRELQKKKEELNAVRRQAEGL

SEDGAAMAVEPTQIQLSKRWREIESKFAQFRRLNFAQIHTVREETMMVMTEDMPLEISYVP

STYLTEITHVSQALLEVEQLLNAPDLCAKDFEDLFKQEESLKNIKDSLQQSSGRIDIIHSKKT

AALQSATPVERVKLQEALSQLDFQWEKVNKMYKDRQGRFDRSVEKWRRFHYDIKIFNQW

LTEAEQFLRKTQIPENWEHAKYKWYLKELQDGIGQRQTVVRTLNATGEEIIQQSSKTDASIL

QEKLGSLNLRWQEVCKQLSDRKKRLEEQKNILSEFQRDLNEFVLWLEEADNIASIPLEPGK

EQQLKEKLEQVKLLVEELPLRQGILKQLNETGGPVLVSAPISPEEQDKLENKLKQTNLQWI

KVSRALPEKQGEIEAQIKDLGQLEKKLEDLEEQLNHLLLWLSPIRNQLEIYNQPNQEGPFD

VQETEIAVQAKQPDVEEILSKGQHLYKEKPATQPVKRKLEDLSSEWKAVNRLLQELRAKQP

DLAPGLTTIGASPTQTVTLVTQPVVTKETAISKLEMPSSLMLEVPALADFNRAWTELTDWLS

LLDQVIKSQRVMVGDLEDINEMIIKQKATMQDLEQRRPQLEELITAAQNLKNKTSNQEART

IITDRIERIQNQWDEVQEHLQNRRQQLNEMLKDSTQWLEAKEEAEQVLGQARAKLESWKE

-continued

GPYTVDAIQKKITETKQLAKDLRQWQTNVDVANDLALKLLRDYSADDTRKVHMITENINAS
WRSIHKRVSEREAALEETHRLLQQFPLDLEKFLAWLTEAETTANVLQDATRKERLLEDSKG
VKELMKQWQDLQGEIEAHTDVYHNLDENSQKILRSLEGSDDAVLLQRRLDNMNFKWSEL
RKKSLNIRSHLEASSDQWKRLHLSLQELLVWLQLKDDELSRQAPIGGDFPAVQKQNDVHR
AFKRELKTKEPVIMSTLETVRIFLTEQPLEGLEKLYQEPRELPPEERAQNVTRLLRKQAEEV
NTEWEKLNLHSADWQRKIDETLERLQELQEATDELDLKLRQAEVIKGSWQPVGDLLIDSL
QDHLEKVKALRGEIAPLKENVSHVNDLARQLTTLGIQLSPYNLSTLEDLNTRWKLLQVAVE
DRVRQLHEAHRDFGPASQHFLSTSVQGPWERAISPNKVPYYINHETQTTCWDHPKMTELY
QSLADLNNVRFSAYRTAMKLRRLQKALCLDLLSLSAACDALDQHNLKQNDQPMDILQIINC
LTTIYDRLEQEHNNLVNVPLCVDMCLNWLLNVYDTGRTGRIRVLSFKTGIISLCKAHLEDK
YRYLFKQVASSTGFCDQRRLGLLLHDSIQIPRQLGEVASFGGSNIEPSVRSCFQFANNKPEIE
AALFLDWMRLEPQSMVWLPVLHRVAAAETAKHQAKCNICKECPIIGFRYRSLKHFNYDICQ
SCFFSGRVAKGHKMHYPMVEYCTPTTSGEDVRDFAKVLKNKFRTKRYFAKHPRMGYLPV
QTVLEGDNMETPVTLINFWPVDSAPASSPQLSHDDTHSRIEHYASRLAEMENSNGSYLNDS
ISPNESIDDEHLLIQHYCQSLNQDSPLSQPRSPAQILISLESEERGELERILADLEEENRNLQ
AEYDRLKQQHEHKGLSPLPSPPEMMPTSPQSPRDAELIAEAKLLRQHKGRLEARMQILED
HNKQLESQLHRLRQLLEQPQAEAKVNGTTVSSPSTSLQRSDSSQPMLLRVVGSQTSDSMGE
EDLLSPPQDTSTGLEEVMEQLNNSFPSSRGRNTPGKPMREDTM

---

The invention claimed is:

1. An isolated antisense oligonucleotide consisting of 7, 8, 9, or 10 nucleotides and comprising the base sequence of 5'-UCAGCUUCUGUUAGCCACUG-3' (SEQ ID NO: 5), said oligonucleotide comprising a modification.

2. The oligonucleotide according to claim 1, consisting of 20 nucleotides having the base sequence of 5'-UCAGCU-UCUGUUAGCCACUG-3' (SEQ ID NO: 5).

3. The oligonucleotide according to claim 1, wherein said nucleotides comprise one or more DNA bases.

4. The oligonucleotide according to claim 1, wherein said modification is selected from the group consisting of: a modified base, a modified sugar moiety, and a modified internucleoside linkage.

5. The oligonucleotide of claim 1, having a modified backbone.

6. The oligonucleotide of claim 4, comprising a ribose moiety that is mono- or di-substituted at the 2', 3' and/or 5' position.

7. The oligonucleotide according to claim 6, comprising a 2'-O substituted ribose and a phosphorothioate modified internucleoside linkage.

8. The antisense oligonucleotide of claim 6, comprising a 2'-O-methyl ribose and a phosphorothioate modified internucleoside linkage.

9. The oligonucleotide according to claim 1, comprising a phosphorothioate modified internucleoside linkage ribose, wherein ribose moieties are each 2'-O-methyl substituted.

10. An isolated antisense oligonucleotide comprising a phosphorothioate backbone consisting of 20 nucleotides having the base sequence of 5'-UCAGCUUCUGUUAGC-CACUG-3' (SEQ ID NO: 5), wherein each of the sugar moieties is 2'-O-methyl substituted.

11. A viral-based vector comprising an expression cassette for expression of the oligonucleotide consisting of 7, 8, 9 or 10 nucleotides and comprising the base sequence of 5'-UCAGCUUCUGUUAGCCACUG-3' (SEQ ID NO: 5).

12. A pharmaceutical composition comprising the oligonucleotide of claim 1 or the vector of claim 11 and a pharmaceutically acceptable carrier.

13. A method for inducing skipping of exon 44 of pre-mRNA of the dystrophin gene in a DMD or BMD patient, wherein the genome of said patient comprises a mutation in the DMD gene selected from the group consisting of: one of a deletion of exon 03-43, exon 05-43, exon 06-43, exon 10-43, exon 13-43, exon 14-43, exon 17-43, exon 19-43, exon 28-43, exon 30-43, exon 31-43, exon 33-43, exon 34-43, exon 35-43, exon 36-43, exon 37-43, exon 38-43, exon 40-43, exon 41-43, exon 42-43, exon 43-45, exon 45-54 and exon 45-68, a duplication of exon 44, a deletion of exon 43, and a deletion of exon 45, a nonsense point mutation in exon 43, and a nonsense point mutation in exon 45 of the dystrophin pre-mRNA, wherein the method comprises administering to said patient an amount of the oligonucleotide of claim 1, the vector of claim 11 or the pharmaceutical composition of claim 12 effective to induce the skipping of said exon 44.

14. A method for inducing skipping of exon 44 of the pre-mRNA of the dystrophin gene in a cell comprising providing the cell with the oligonucleotide of claim 1, the vector of claim 11 or the pharmaceutical composition of claim 12.

15. The oligonucleotide according to claim 1, wherein said oligonucleotide induces skipping of exon 44 of the dystrophin pre-mRNA.

* * * * *

UNITED STATES PATENT AND TRADEMARK OFFICE
CERTIFICATE OF CORRECTION

PATENT NO.         : 9,139,828 B2
APPLICATION NO.    : 12/992218
DATED              : September 22, 2015
INVENTOR(S)        : Platenburg et al.

Page 1 of 1

It is certified that error appears in the above-identified patent and that said Letters Patent is hereby corrected as shown below:

In The Claims

In Col. 66, lines 2, 3
replace "oligonucleotide consisting of 7, 8, 9 or 10 nucleotides"
with "oligonucleotide consisting of 20, 21, 22 or 23 nucleotides"

In Col. 67, lines 26, 27
replace "oligonucleotide consisting of 7, 8, 9 or 10 nucleotides"
with "oligonucleotide consisting of 20, 21, 22 or 23 nucleotides"

Signed and Sealed this
Twenty-sixth Day of January, 2016

Michelle K. Lee
*Director of the United States Patent and Trademark Office*

SEQUENCE LISTING

<160> NUMBER OF SEQ ID NOS: 55

<210> SEQ ID NO 1
<211> LENGTH: 16
<212> TYPE: DNA
<213> ORGANISM: Homo sapiens

<400> SEQUENCE: 1
guggcuaaca gaagcu                                                         16

<210> SEQ ID NO 2
<211> LENGTH: 17
<212> TYPE: DNA
<213> ORGANISM: Homo sapiens

<400> SEQUENCE: 2
gggaacaugc uaaauac                                                        17

<210> SEQ ID NO 3
<211> LENGTH: 18
<212> TYPE: DNA
<213> ORGANISM: Homo sapiens

<400> SEQUENCE: 3
agacacaaau uccugaga                                                       18

<210> SEQ ID NO 4
<211> LENGTH: 11
<212> TYPE: DNA
<213> ORGANISM: Homo sapiens

<400> SEQUENCE: 4

```
cuguugagaa a                                                                11

<210> SEQ ID NO 5
<211> LENGTH: 20
<212> TYPE: RNA
<213> ORGANISM: Artificial
<220> FEATURE:
<223> OTHER INFORMATION: AON

<400> SEQUENCE: 5
ucagcuucug uuagccacug                                                       20

<210> SEQ ID NO 6
<211> LENGTH: 20
<212> TYPE: RNA
<213> ORGANISM: Artificial
<220> FEATURE:
<223> OTHER INFORMATION: AON

<400> SEQUENCE: 6
uucagcuucu guuagccacu                                                       20

<210> SEQ ID NO 7
<211> LENGTH: 21
<212> TYPE: RNA
<213> ORGANISM: Artificial
<220> FEATURE:
<223> OTHER INFORMATION: AON

<400> SEQUENCE: 7
uucagcuucu guuagccacu g                                                     21

<210> SEQ ID NO 8
<211> LENGTH: 21
<212> TYPE: RNA
<213> ORGANISM: Artificial
<220> FEATURE:
<223> OTHER INFORMATION: AON

<400> SEQUENCE: 8
ucagcuucug uuagccacug a                                                     21

<210> SEQ ID NO 9
<211> LENGTH: 22
<212> TYPE: RNA
<213> ORGANISM: Artificial
<220> FEATURE:
<223> OTHER INFORMATION: AON

<400> SEQUENCE: 9
uucagcuucu guuagccacu ga                                                    22

<210> SEQ ID NO 10
<211> LENGTH: 21
<212> TYPE: RNA
<213> ORGANISM: Artificial
<220> FEATURE:
<223> OTHER INFORMATION: AON

<400> SEQUENCE: 10
ucagcuucug uuagccacug a                                                     21

<210> SEQ ID NO 11
<211> LENGTH: 22
<212> TYPE: RNA
```

```
<213> ORGANISM: Artificial
<220> FEATURE:
<223> OTHER INFORMATION: AON

<400> SEQUENCE: 11
uucagcuucu guuagccacu ga                                             22

<210> SEQ ID NO 12
<211> LENGTH: 22
<212> TYPE: RNA
<213> ORGANISM: Artificial
<220> FEATURE:
<223> OTHER INFORMATION: AON

<400> SEQUENCE: 12
ucagcuucug uuagccacug au                                             22

<210> SEQ ID NO 13
<211> LENGTH: 23
<212> TYPE: RNA
<213> ORGANISM: Artificial
<220> FEATURE:
<223> OTHER INFORMATION: AON

<400> SEQUENCE: 13
uucagcuucu guuagccacu gau                                            23

<210> SEQ ID NO 14
<211> LENGTH: 23
<212> TYPE: RNA
<213> ORGANISM: Artificial
<220> FEATURE:
<223> OTHER INFORMATION: AON

<400> SEQUENCE: 14
ucagcuucug uuagccacug auu                                            23

<210> SEQ ID NO 15
<211> LENGTH: 24
<212> TYPE: RNA
<213> ORGANISM: Artificial
<220> FEATURE:
<223> OTHER INFORMATION: AON

<400> SEQUENCE: 15
uucagcuucu guuagccacu gauu                                           24

<210> SEQ ID NO 16
<211> LENGTH: 24
<212> TYPE: RNA
<213> ORGANISM: Artificial
<220> FEATURE:
<223> OTHER INFORMATION: AON

<400> SEQUENCE: 16
ucagcuucug uuagccacug auua                                           24

<210> SEQ ID NO 17
<211> LENGTH: 24
<212> TYPE: RNA
<213> ORGANISM: Artificial
<220> FEATURE:
<223> OTHER INFORMATION: AON

<400> SEQUENCE: 17
uucagcuucu guuagccacu gaua                                           24
```

```
<210> SEQ ID NO 18
<211> LENGTH: 25
<212> TYPE: RNA
<213> ORGANISM: Artificial
<220> FEATURE:
<223> OTHER INFORMATION: AON

<400> SEQUENCE: 18
ucagcuucug uuagccacug auuaa                                           25

<210> SEQ ID NO 19
<211> LENGTH: 26
<212> TYPE: RNA
<213> ORGANISM: Artificial
<220> FEATURE:
<223> OTHER INFORMATION: AON

<400> SEQUENCE: 19
uucagcuucu guuagccacu gauuaa                                          26

<210> SEQ ID NO 20
<211> LENGTH: 26
<212> TYPE: RNA
<213> ORGANISM: Artificial
<220> FEATURE:
<223> OTHER INFORMATION: AON

<400> SEQUENCE: 20
ucagcuucug uuagccacug auuaaa                                          26

<210> SEQ ID NO 21
<211> LENGTH: 27
<212> TYPE: RNA
<213> ORGANISM: Artificial
<220> FEATURE:
<223> OTHER INFORMATION: AON

<400> SEQUENCE: 21
uucagcuucu guuagccacu gauuaaa                                         27

<210> SEQ ID NO 22
<211> LENGTH: 19
<212> TYPE: RNA
<213> ORGANISM: Artificial
<220> FEATURE:
<223> OTHER INFORMATION: AON

<400> SEQUENCE: 22
cagcuucugu uagccacug                                                  19

<210> SEQ ID NO 23
<211> LENGTH: 21
<212> TYPE: RNA
<213> ORGANISM: Artificial
<220> FEATURE:
<223> OTHER INFORMATION: AON

<400> SEQUENCE: 23
cagcuucugu uagccacuga u                                               21

<210> SEQ ID NO 24
<211> LENGTH: 21
<212> TYPE: RNA
<213> ORGANISM: Artificial
<220> FEATURE:
```

<223> OTHER INFORMATION: AON

<400> SEQUENCE: 24
agcuucuguu agccacugau u                                      21

<210> SEQ ID NO 25
<211> LENGTH: 22
<212> TYPE: RNA
<213> ORGANISM: Artificial
<220> FEATURE:
<223> OTHER INFORMATION: AON

<400> SEQUENCE: 25
cagcuucugu uagccacuga uu                                     22

<210> SEQ ID NO 26
<211> LENGTH: 22
<212> TYPE: RNA
<213> ORGANISM: Artificial
<220> FEATURE:
<223> OTHER INFORMATION: AON

<400> SEQUENCE: 26
agcuucuguu agccacugau ua                                     22

<210> SEQ ID NO 27
<211> LENGTH: 23
<212> TYPE: RNA
<213> ORGANISM: Artificial
<220> FEATURE:
<223> OTHER INFORMATION: AON

<400> SEQUENCE: 27
cagcuucugu uagccacuga uua                                    23

<210> SEQ ID NO 28
<211> LENGTH: 23
<212> TYPE: RNA
<213> ORGANISM: Artificial
<220> FEATURE:
<223> OTHER INFORMATION: AON

<400> SEQUENCE: 28
agcuucuguu agccacugau uaa                                    23

<210> SEQ ID NO 29
<211> LENGTH: 24
<212> TYPE: RNA
<213> ORGANISM: Artificial
<220> FEATURE:
<223> OTHER INFORMATION: AON

<400> SEQUENCE: 29
cagcuucugu uagccacuga uuaa                                   24

<210> SEQ ID NO 30
<211> LENGTH: 24
<212> TYPE: RNA
<213> ORGANISM: Artificial
<220> FEATURE:
<223> OTHER INFORMATION: AON

<400> SEQUENCE: 30
agcuucuguu agccacugau uaaa                                   24

```
<210> SEQ ID NO 31
<211> LENGTH: 25
<212> TYPE: RNA
<213> ORGANISM: Artificial
<220> FEATURE:
<223> OTHER INFORMATION: AON

<400> SEQUENCE: 31
cagcuucugu uagccacuga uuaaa                                            25

<210> SEQ ID NO 32
<211> LENGTH: 24
<212> TYPE: RNA
<213> ORGANISM: Artificial
<220> FEATURE:
<223> OTHER INFORMATION: AON

<400> SEQUENCE: 32
agcuucuguu agccacugau uaaa                                             24

<210> SEQ ID NO 33
<211> LENGTH: 20
<212> TYPE: RNA
<213> ORGANISM: Artificial
<220> FEATURE:
<223> OTHER INFORMATION: AON

<400> SEQUENCE: 33
agcuucuguu agccacugau                                                  20

<210> SEQ ID NO 34
<211> LENGTH: 20
<212> TYPE: RNA
<213> ORGANISM: Artificial
<220> FEATURE:
<223> OTHER INFORMATION: AON

<400> SEQUENCE: 34
gcuucuguua gccacugauu                                                  20

<210> SEQ ID NO 35
<211> LENGTH: 21
<212> TYPE: RNA
<213> ORGANISM: Artificial
<220> FEATURE:
<223> OTHER INFORMATION: AON

<400> SEQUENCE: 35
agcuucuguu agccacugau u                                                21

<210> SEQ ID NO 36
<211> LENGTH: 21
<212> TYPE: RNA
<213> ORGANISM: Artificial
<220> FEATURE:
<223> OTHER INFORMATION: AON

<400> SEQUENCE: 36
gcuucuguua gccacugauu a                                                21

<210> SEQ ID NO 37
<211> LENGTH: 22
<212> TYPE: RNA
<213> ORGANISM: Artificial
<220> FEATURE:
<223> OTHER INFORMATION: AON
```

```
<400> SEQUENCE: 37
agcuucuguu agccacugau ua                                              22

<210> SEQ ID NO 38
<211> LENGTH: 22
<212> TYPE: RNA
<213> ORGANISM: Artificial
<220> FEATURE:
<223> OTHER INFORMATION: AON

<400> SEQUENCE: 38
gcuucuguua gccacugauu aa                                              22

<210> SEQ ID NO 39
<211> LENGTH: 23
<212> TYPE: RNA
<213> ORGANISM: Artificial
<220> FEATURE:
<223> OTHER INFORMATION: AON

<400> SEQUENCE: 39
agcuucuguu agccacugau uaa                                             23

<210> SEQ ID NO 40
<211> LENGTH: 23
<212> TYPE: RNA
<213> ORGANISM: Artificial
<220> FEATURE:
<223> OTHER INFORMATION: AON

<400> SEQUENCE: 40
gcuucuguua gccacugauu aaa                                             23

<210> SEQ ID NO 41
<211> LENGTH: 24
<212> TYPE: RNA
<213> ORGANISM: Artificial
<220> FEATURE:
<223> OTHER INFORMATION: AON

<400> SEQUENCE: 41
agcuucuguu agccacugau uaaa                                            24

<210> SEQ ID NO 42
<211> LENGTH: 23
<212> TYPE: RNA
<213> ORGANISM: Artificial
<220> FEATURE:
<223> OTHER INFORMATION: AON

<400> SEQUENCE: 42
gcuucuguua gccacugauu aaa                                             23

<210> SEQ ID NO 43
<211> LENGTH: 23
<212> TYPE: RNA
<213> ORGANISM: Artificial
<220> FEATURE:
<223> OTHER INFORMATION: AON

<400> SEQUENCE: 43
ccauuuguau uuagcauguu ccc                                             23

<210> SEQ ID NO 44
<211> LENGTH: 20
```

```
<212> TYPE: RNA
<213> ORGANISM: Artificial
<220> FEATURE:
<223> OTHER INFORMATION: AON

<400> SEQUENCE: 44
agauaccauu uguauuuagc                                              20

<210> SEQ ID NO 45
<211> LENGTH: 19
<212> TYPE: RNA
<213> ORGANISM: Artificial
<220> FEATURE:
<223> OTHER INFORMATION: AON

<400> SEQUENCE: 45
gccauuucuc aacagaucu                                               19

<210> SEQ ID NO 46
<211> LENGTH: 23
<212> TYPE: RNA
<213> ORGANISM: Artificial
<220> FEATURE:
<223> OTHER INFORMATION: AON

<400> SEQUENCE: 46
gccauuucuc aacagaucug uca                                          23

<210> SEQ ID NO 47
<211> LENGTH: 23
<212> TYPE: RNA
<213> ORGANISM: Artificial
<220> FEATURE:
<223> OTHER INFORMATION: AON

<400> SEQUENCE: 47
auucucagga auugugucu uuc                                           23

<210> SEQ ID NO 48
<211> LENGTH: 21
<212> TYPE: RNA
<213> ORGANISM: Artificial
<220> FEATURE:
<223> OTHER INFORMATION: AON

<400> SEQUENCE: 48
ucucaggaau uugugucuuu c                                            21

<210> SEQ ID NO 49
<211> LENGTH: 18
<212> TYPE: RNA
<213> ORGANISM: Artificial
<220> FEATURE:
<223> OTHER INFORMATION: AON

<400> SEQUENCE: 49
guucagcuuc uguuagcc                                                18

<210> SEQ ID NO 50
<211> LENGTH: 21
<212> TYPE: RNA
<213> ORGANISM: Artificial
<220> FEATURE:
<223> OTHER INFORMATION: AON

<400> SEQUENCE: 50
```
cugauuaaau aucuuuauau c                                              21

<210> SEQ ID NO 51
<211> LENGTH: 18
<212> TYPE: RNA
<213> ORGANISM: Artificial
<220> FEATURE:
<223> OTHER INFORMATION: AON

<400> SEQUENCE: 51
gccgccauuu cucaacag                                                  18

<210> SEQ ID NO 52
<211> LENGTH: 18
<212> TYPE: RNA
<213> ORGANISM: Artificial
<220> FEATURE:
<223> OTHER INFORMATION: AON

<400> SEQUENCE: 52
guauuuagca uguuccca                                                  18

<210> SEQ ID NO 53
<211> LENGTH: 18
<212> TYPE: RNA
<213> ORGANISM: Artificial
<220> FEATURE:
<223> OTHER INFORMATION: AON

<400> SEQUENCE: 53
caggaauuug ugucuuuc                                                  18

<210> SEQ ID NO 54
<211> LENGTH: 21
<212> TYPE: DNA
<213> ORGANISM: Artificial
<220> FEATURE:
<223> OTHER INFORMATION: AON

<400> SEQUENCE: 54
ucuguuagcc acugauuaaa u                                              21

<210> SEQ ID NO 55
<211> LENGTH: 3685
<212> TYPE: PRT
<213> ORGANISM: Homo sapiens

<400> SEQUENCE: 55

Met Leu Trp Trp Glu Glu Val Glu Asp Cys Tyr Glu Arg Glu Asp Val
 1               5                  10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

-continued

```
Asn Ile Ile Leu His Trp Gln Val Lys Asn Val Met Lys Asn Ile Met
            115                 120                 125
Ala Gly Leu Gln Gln Thr Asn Ser Glu Lys Ile Leu Leu Ser Trp Val
130                 135                 140
Arg Gln Ser Thr Arg Asn Tyr Pro Gln Val Asn Val Ile Asn Phe Thr
145                 150                 155                 160
Thr Ser Trp Ser Asp Gly Leu Ala Leu Asn Ala Leu Ile His Ser His
                165                 170                 175
Arg Pro Asp Leu Phe Asp Trp Asn Ser Val Val Cys Gln Gln Ser Ala
            180                 185                 190
Thr Gln Arg Leu Glu His Ala Phe Asn Ile Ala Arg Tyr Gln Leu Gly
        195                 200                 205
Ile Glu Lys Leu Leu Asp Pro Glu Asp Val Asp Thr Thr Tyr Pro Asp
210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Glu Met Leu Pro Arg
                245                 250                 255
Pro Pro Lys Val Thr Lys Glu Glu His Phe Gln Leu His His Gln Met
            260                 265                 270
His Tyr Ser Gln Gln Ile Thr Val Ser Leu Ala Gln Gly Tyr Glu Arg
        275                 280                 285
Thr Ser Ser Pro Lys Pro Arg Phe Lys Ser Tyr Ala Tyr Thr Gln Ala
290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
            340                 345                 350
Ser Trp Leu Leu Ser Ala Glu Asp Thr Leu Gln Ala Gln Gly Glu Ile
        355                 360                 365
Ser Asn Asp Val Glu Val Val Lys Asp Gln Phe His Thr His Glu Gly
370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
            420                 425                 430
Cys Leu Arg Val Ala Ser Met Glu Lys Gln Ser Asn Leu His Arg Val
        435                 440                 445
Leu Met Asp Leu Gln Asn Gln Lys Leu Lys Glu Leu Asn Asp Trp Leu
450                 455                 460
Thr Lys Thr Glu Glu Arg Thr Arg Lys Met Glu Glu Pro Leu Gly
465                 470                 475                 480
Pro Asp Leu Glu Asp Leu Lys Arg Gln Val Gln Gln His Lys Val Leu
                485                 490                 495
Gln Glu Asp Leu Glu Gln Glu Gln Val Arg Val Asn Ser Leu Thr His
            500                 505                 510
Met Val Val Val Asp Glu Ser Ser Gly Asp His Ala Thr Ala Ala
        515                 520                 525
Leu Glu Glu Gln Leu Lys Val Leu Gly Asp Arg Trp Ala Asn Ile Cys
```

-continued

```
            530                 535                 540
Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                    565                 570                 575

Glu Lys Glu Asp Ala Val Asn Lys Ile His Thr Thr Gly Phe Lys Asp
                580                 585                 590

Gln Asn Glu Met Leu Ser Ser Leu Gln Lys Leu Ala Val Leu Lys Ala
                    595                 600                 605

Asp Leu Glu Lys Lys Lys Gln Ser Met Gly Lys Leu Tyr Ser Leu Lys
                610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                    645                 650                 655

Lys Leu Glu Lys Ser Thr Ala Gln Ile Ser Gln Ala Val Thr Thr Thr
                    660                 665                 670

Gln Pro Ser Leu Thr Gln Thr Thr Val Met Glu Thr Val Thr Thr Val
                675                 680                 685

Thr Thr Arg Glu Gln Ile Leu Val Lys His Ala Gln Glu Glu Leu Pro
690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                    725                 730                 735

Arg Ser Glu Ala Val Leu Gln Ser Pro Glu Phe Ala Ile Phe Arg Lys
                740                 745                 750

Glu Gly Asn Phe Ser Asp Leu Lys Glu Lys Val Asn Ala Ile Glu Arg
                    755                 760                 765

Glu Lys Ala Glu Lys Phe Arg Lys Leu Gln Asp Ala Ser Arg Ser Ala
                770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                    805                 810                 815

Gln Leu Leu Ser Glu Arg Leu Asn Trp Leu Glu Tyr Gln Asn Asn Ile
                820                 825                 830

Ile Ala Phe Tyr Asn Gln Leu Gln Gln Leu Glu Gln Met Thr Thr Thr
                835                 840                 845

Ala Glu Asn Trp Leu Lys Ile Gln Pro Thr Thr Pro Ser Glu Pro Thr
850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                    885                 890                 895

Leu Lys Glu Lys Gly Gln Gly Pro Met Phe Leu Asp Ala Asp Phe Val
                900                 905                 910

Ala Phe Thr Asn His Phe Lys Gln Val Phe Ser Asp Val Gln Ala Arg
                915                 920                 925

Glu Lys Glu Leu Gln Thr Ile Phe Asp Thr Leu Pro Pro Met Arg Tyr
                930                 935                 940

Gln Glu Thr Met Ser Ala Ile Arg Thr Trp Val Gln Gln Ser Glu Thr
945                 950                 955                 960
```

-continued

```
Lys Leu Ser Ile Pro Gln Leu Ser Val Thr Asp Tyr Glu Ile Met Glu
            965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser Thr Thr Val Lys Glu Met Ser Lys
            995                1000                1005

Lys Ala Pro Ser Glu Ile Ser Arg Lys Tyr Gln Ser Glu Phe Glu
        1010                1015                1020

Glu Ile Glu Gly Arg Trp Lys Lys Leu Ser Ser Gln Leu Val Glu
        1025                1030                1035

His Cys Gln Lys Leu Glu Glu Gln Met Asn Lys Leu Arg Lys Ile
        1040                1045                1050

Gln Asn His Ile Gln Thr Leu Lys Lys Trp Met Ala Glu Val Asp
        1055                1060                1065

Val Phe Leu Lys Glu Glu Trp Pro Ala Leu Gly Asp Ser Glu Ile
        1070                1075                1080

Leu Lys Lys Gln Leu Lys Gln Cys Arg Leu Leu Val Ser Asp Ile
        1085                1090                1095

Gln Thr Ile Gln Pro Ser Leu Asn Ser Val Asn Glu Gly Gly Gln
        1100                1105                1110

Lys Ile Lys Asn Glu Ala Glu Pro Glu Phe Ala Ser Arg Leu Glu
        1115                1120                1125

Thr Glu Leu Lys Glu Leu Asn Thr Gln Trp Asp His Met Cys Gln
        1130                1135                1140

Gln Val Tyr Ala Arg Lys Glu Ala Leu Lys Gly Gly Leu Glu Lys
        1145                1150                1155

Thr Val Ser Leu Gln Lys Asp Leu Ser Glu Met His Glu Trp Met
        1160                1165                1170

Thr Gln Ala Glu Glu Glu Tyr Leu Glu Arg Asp Phe Glu Tyr Lys
        1175                1180                1185

Thr Pro Asp Glu Leu Gln Lys Ala Val Glu Glu Met Lys Arg Ala
        1190                1195                1200

Lys Glu Glu Ala Gln Gln Lys Glu Ala Lys Val Lys Leu Leu Thr
        1205                1210                1215

Glu Ser Val Asn Ser Val Ile Ala Gln Ala Pro Pro Val Ala Gln
        1220                1225                1230

Glu Ala Leu Lys Lys Glu Leu Glu Thr Leu Thr Thr Asn Tyr Gln
        1235                1240                1245

Trp Leu Cys Thr Arg Leu Asn Gly Lys Cys Lys Thr Leu Glu Glu
        1250                1255                1260

Val Trp Ala Cys Trp His Glu Leu Leu Ser Tyr Leu Glu Lys Ala
        1265                1270                1275

Asn Lys Trp Leu Asn Glu Val Glu Phe Lys Leu Lys Thr Thr Glu
        1280                1285                1290

Asn Ile Pro Gly Gly Ala Glu Glu Ile Ser Glu Val Leu Asp Ser
        1295                1300                1305

Leu Glu Asn Leu Met Arg His Ser Glu Asp Asn Pro Asn Gln Ile
        1310                1315                1320

Arg Ile Leu Ala Gln Thr Leu Thr Asp Gly Gly Val Met Asp Glu
        1325                1330                1335

Leu Ile Asn Glu Glu Leu Glu Thr Phe Asn Ser Arg Trp Arg Glu
        1340                1345                1350
```

```
Leu His Glu Glu Ala Val Arg  Arg Gln Lys Leu Leu  Gln Gln Ser
    1355                1360               1365

Ile Gln Ser Ala Gln Glu Thr  Glu Lys Ser Leu His  Leu Ile Gln
    1370                1375               1380

Glu Ser Leu Thr Phe Ile Asp  Lys Gln Leu Ala Ala  Tyr Ile Ala
    1385                1390               1395

Asp Lys Val Asp Ala Ala Gln  Met Pro Gln Glu Ala  Gln Lys Ile
    1400                1405               1410

Gln Ser Asp Leu Thr Ser His  Glu Ile Ser Leu Glu  Glu Met Lys
    1415                1420               1425

Lys His Asn Gln Gly Lys Glu  Ala Ala Gln Arg Val  Leu Ser Gln
    1430                1435               1440

Ile Asp Val Ala Gln Lys Lys  Leu Gln Asp Val Ser  Met Lys Phe
    1445                1450               1455

Arg Leu Phe Gln Lys Pro Ala  Asn Phe Glu Gln Arg  Leu Gln Glu
    1460                1465               1470

Ser Lys Met Ile Leu Asp Glu  Val Lys Met His Leu  Pro Ala Leu
    1475                1480               1485

Glu Thr Lys Ser Val Glu Gln  Glu Val Val Gln Ser  Gln Leu Asn
    1490                1495               1500

His Cys Val Asn Leu Tyr Lys  Ser Leu Ser Glu Val  Lys Ser Glu
    1505                1510               1515

Val Glu Met Val Ile Lys Thr  Gly Arg Gln Ile Val  Gln Lys Lys
    1520                1525               1530

Gln Thr Glu Asn Pro Lys Glu  Leu Asp Glu Arg Val  Thr Ala Leu
    1535                1540               1545

Lys Leu His Tyr Asn Glu Leu  Gly Ala Lys Val Thr  Glu Arg Lys
    1550                1555               1560

Gln Gln Leu Glu Lys Cys Leu  Lys Leu Ser Arg Lys  Met Arg Lys
    1565                1570               1575

Glu Met Asn Val Leu Thr Glu  Trp Leu Ala Ala Thr  Asp Met Glu
    1580                1585               1590

Leu Thr Lys Arg Ser Ala Val  Glu Gly Met Pro Ser  Asn Leu Asp
    1595                1600               1605

Ser Glu Val Ala Trp Gly Lys  Ala Thr Gln Lys Glu  Ile Glu Lys
    1610                1615               1620

Gln Lys Val His Leu Lys Ser  Ile Thr Glu Val Gly  Glu Ala Leu
    1625                1630               1635

Lys Thr Val Leu Gly Lys Lys  Glu Thr Leu Val Glu  Asp Lys Leu
    1640                1645               1650

Ser Leu Leu Asn Ser Asn Trp  Ile Ala Val Thr Ser  Arg Ala Glu
    1655                1660               1665

Glu Trp Leu Asn Leu Leu Leu  Glu Tyr Gln Lys His  Met Glu Thr
    1670                1675               1680

Phe Asp Gln Asn Val Asp His  Ile Thr Lys Trp Ile  Ile Gln Ala
    1685                1690               1695

Asp Thr Leu Leu Asp Glu Ser  Glu Lys Lys Lys Pro  Gln Gln Lys
    1700                1705               1710

Glu Asp Val Leu Lys Arg Leu  Lys Ala Glu Leu Asn  Asp Ile Arg
    1715                1720               1725

Pro Lys Val Asp Ser Thr Arg  Asp Gln Ala Ala Asn  Leu Met Ala
    1730                1735               1740

Asn Arg Gly Asp His Cys Arg  Lys Leu Val Glu Pro  Gln Ile Ser
```

-continued

```
           1745                1750               1755
Glu Leu Asn His Arg Phe Ala Ala Ile Ser His Arg Ile Lys Thr
       1760                1765               1770
Gly Lys Ala Ser Ile Pro Leu Lys Glu Leu Glu Gln Phe Asn Ser
       1775                1780               1785
Asp Ile Gln Lys Leu Leu Glu Pro Leu Glu Ala Glu Ile Gln Gln
       1790                1795               1800
Gly Val Asn Leu Lys Glu Glu Asp Phe Asn Lys Asp Met Asn Glu
       1805                1810               1815
Asp Asn Glu Gly Thr Val Lys Glu Leu Leu Gln Arg Gly Asp Asn
       1820                1825               1830
Leu Gln Gln Arg Ile Thr Asp Glu Arg Lys Arg Glu Glu Ile Lys
       1835                1840               1845
Ile Lys Gln Gln Leu Leu Gln Thr Lys His Asn Ala Leu Lys Asp
       1850                1855               1860
Leu Arg Ser Gln Arg Arg Lys Lys Ala Leu Glu Ile Ser His Gln
       1865                1870               1875
Trp Tyr Gln Tyr Lys Arg Gln Ala Asp Asp Leu Leu Lys Cys Leu
       1880                1885               1890
Asp Asp Ile Glu Lys Lys Leu Ala Ser Leu Pro Glu Pro Arg Asp
       1895                1900               1905
Glu Arg Lys Ile Lys Glu Ile Asp Arg Glu Leu Gln Lys Lys Lys
       1910                1915               1920
Glu Glu Leu Asn Ala Val Arg Arg Gln Ala Glu Gly Leu Ser Glu
       1925                1930               1935
Asp Gly Ala Ala Met Ala Val Glu Pro Thr Gln Ile Gln Leu Ser
       1940                1945               1950
Lys Arg Trp Arg Glu Ile Glu Ser Lys Phe Ala Gln Phe Arg Arg
       1955                1960               1965
Leu Asn Phe Ala Gln Ile His Thr Val Arg Glu Glu Thr Met Met
       1970                1975               1980
Val Met Thr Glu Asp Met Pro Leu Glu Ile Ser Tyr Val Pro Ser
       1985                1990               1995
Thr Tyr Leu Thr Glu Ile Thr His Val Ser Gln Ala Leu Leu Glu
       2000                2005               2010
Val Glu Gln Leu Leu Asn Ala Pro Asp Leu Cys Ala Lys Asp Phe
       2015                2020               2025
Glu Asp Leu Phe Lys Gln Glu Glu Ser Leu Lys Asn Ile Lys Asp
       2030                2035               2040
Ser Leu Gln Gln Ser Ser Gly Arg Ile Asp Ile Ile His Ser Lys
       2045                2050               2055
Lys Thr Ala Ala Leu Gln Ser Ala Thr Pro Val Glu Arg Val Lys
       2060                2065               2070
Leu Gln Glu Ala Leu Ser Gln Leu Asp Phe Gln Trp Glu Lys Val
       2075                2080               2085
Asn Lys Met Tyr Lys Asp Arg Gln Gly Arg Phe Asp Arg Ser Val
       2090                2095               2100
Glu Lys Trp Arg Arg Phe His Tyr Asp Ile Lys Ile Phe Asn Gln
       2105                2110               2115
Trp Leu Thr Glu Ala Glu Gln Phe Leu Arg Lys Thr Gln Ile Pro
       2120                2125               2130
Glu Asn Trp Glu His Ala Lys Tyr Lys Trp Tyr Leu Lys Glu Leu
       2135                2140               2145
```

```
Gln Asp Gly Ile Gly Gln Arg Gln Thr Val Val Arg Thr Leu Asn
    2150                2155                2160

Ala Thr Gly Glu Glu Ile Ile Gln Gln Ser Ser Lys Thr Asp Ala
    2165                2170                2175

Ser Ile Leu Gln Glu Lys Leu Gly Ser Leu Asn Leu Arg Trp Gln
    2180                2185                2190

Glu Val Cys Lys Gln Leu Ser Asp Arg Lys Lys Arg Leu Glu Glu
    2195                2200                2205

Gln Lys Asn Ile Leu Ser Glu Phe Gln Arg Asp Leu Asn Glu Phe
    2210                2215                2220

Val Leu Trp Leu Glu Glu Ala Asp Asn Ile Ala Ser Ile Pro Leu
    2225                2230                2235

Glu Pro Gly Lys Glu Gln Gln Leu Lys Glu Lys Leu Glu Gln Val
    2240                2245                2250

Lys Leu Leu Val Glu Glu Leu Pro Leu Arg Gln Gly Ile Leu Lys
    2255                2260                2265

Gln Leu Asn Glu Thr Gly Gly Pro Val Leu Val Ser Ala Pro Ile
    2270                2275                2280

Ser Pro Glu Glu Gln Asp Lys Leu Glu Asn Lys Leu Lys Gln Thr
    2285                2290                2295

Asn Leu Gln Trp Ile Lys Val Ser Arg Ala Leu Pro Glu Lys Gln
    2300                2305                2310

Gly Glu Ile Glu Ala Gln Ile Lys Asp Leu Gly Gln Leu Glu Lys
    2315                2320                2325

Lys Leu Glu Asp Leu Glu Glu Gln Leu Asn His Leu Leu Leu Trp
    2330                2335                2340

Leu Ser Pro Ile Arg Asn Gln Leu Glu Ile Tyr Asn Gln Pro Asn
    2345                2350                2355

Gln Glu Gly Pro Phe Asp Val Gln Glu Thr Glu Ile Ala Val Gln
    2360                2365                2370

Ala Lys Gln Pro Asp Val Glu Glu Ile Leu Ser Lys Gly Gln His
    2375                2380                2385

Leu Tyr Lys Glu Lys Pro Ala Thr Gln Pro Val Lys Arg Lys Leu
    2390                2395                2400

Glu Asp Leu Ser Ser Glu Trp Lys Ala Val Asn Arg Leu Leu Gln
    2405                2410                2415

Glu Leu Arg Ala Lys Gln Pro Asp Leu Ala Pro Gly Leu Thr Thr
    2420                2425                2430

Ile Gly Ala Ser Pro Thr Gln Thr Val Thr Leu Val Thr Gln Pro
    2435                2440                2445

Val Val Thr Lys Glu Thr Ala Ile Ser Lys Leu Glu Met Pro Ser
    2450                2455                2460

Ser Leu Met Leu Glu Val Pro Ala Leu Ala Asp Phe Asn Arg Ala
    2465                2470                2475

Trp Thr Glu Leu Thr Asp Trp Leu Ser Leu Leu Asp Gln Val Ile
    2480                2485                2490

Lys Ser Gln Arg Val Met Val Gly Asp Leu Glu Asp Ile Asn Glu
    2495                2500                2505

Met Ile Ile Lys Gln Lys Ala Thr Met Gln Asp Leu Glu Gln Arg
    2510                2515                2520

Arg Pro Gln Leu Glu Glu Leu Ile Thr Ala Ala Gln Asn Leu Lys
    2525                2530                2535
```

-continued

```
Asn Lys Thr Ser Asn Gln Glu Ala Arg Thr Ile Ile Thr Asp Arg
2540                2545                2550

Ile Glu Arg Ile Gln Asn Gln Trp Asp Glu Val Gln Glu His Leu
2555                2560                2565

Gln Asn Arg Arg Gln Gln Leu Asn Glu Met Leu Lys Asp Ser Thr
2570                2575                2580

Gln Trp Leu Glu Ala Lys Glu Glu Ala Glu Gln Val Leu Gly Gln
2585                2590                2595

Ala Arg Ala Lys Leu Glu Ser Trp Lys Glu Gly Pro Tyr Thr Val
2600                2605                2610

Asp Ala Ile Gln Lys Lys Ile Thr Glu Thr Lys Gln Leu Ala Lys
2615                2620                2625

Asp Leu Arg Gln Trp Gln Thr Asn Val Asp Val Ala Asn Asp Leu
2630                2635                2640

Ala Leu Lys Leu Leu Arg Asp Tyr Ser Ala Asp Asp Thr Arg Lys
2645                2650                2655

Val His Met Ile Thr Glu Asn Ile Asn Ala Ser Trp Arg Ser Ile
2660                2665                2670

His Lys Arg Val Ser Glu Arg Glu Ala Ala Leu Glu Glu Thr His
2675                2680                2685

Arg Leu Leu Gln Gln Phe Pro Leu Asp Leu Glu Lys Phe Leu Ala
2690                2695                2700

Trp Leu Thr Glu Ala Glu Thr Thr Ala Asn Val Leu Gln Asp Ala
2705                2710                2715

Thr Arg Lys Glu Arg Leu Leu Glu Asp Ser Lys Gly Val Lys Glu
2720                2725                2730

Leu Met Lys Gln Trp Gln Asp Leu Gln Gly Glu Ile Glu Ala His
2735                2740                2745

Thr Asp Val Tyr His Asn Leu Asp Glu Asn Ser Gln Lys Ile Leu
2750                2755                2760

Arg Ser Leu Glu Gly Ser Asp Asp Ala Val Leu Leu Gln Arg Arg
2765                2770                2775

Leu Asp Asn Met Asn Phe Lys Trp Ser Glu Leu Arg Lys Lys Ser
2780                2785                2790

Leu Asn Ile Arg Ser His Leu Glu Ala Ser Ser Asp Gln Trp Lys
2795                2800                2805

Arg Leu His Leu Ser Leu Gln Glu Leu Leu Val Trp Leu Gln Leu
2810                2815                2820

Lys Asp Asp Glu Leu Ser Arg Gln Ala Pro Ile Gly Gly Asp Phe
2825                2830                2835

Pro Ala Val Gln Lys Gln Asn Asp Val His Arg Ala Phe Lys Arg
2840                2845                2850

Glu Leu Lys Thr Lys Glu Pro Val Ile Met Ser Thr Leu Glu Thr
2855                2860                2865

Val Arg Ile Phe Leu Thr Glu Gln Pro Leu Glu Gly Leu Glu Lys
2870                2875                2880

Leu Tyr Gln Glu Pro Arg Glu Leu Pro Pro Glu Glu Arg Ala Gln
2885                2890                2895

Asn Val Thr Arg Leu Leu Arg Lys Gln Ala Glu Glu Val Asn Thr
2900                2905                2910

Glu Trp Glu Lys Leu Asn Leu His Ser Ala Asp Trp Gln Arg Lys
2915                2920                2925

Ile Asp Glu Thr Leu Glu Arg Leu Gln Glu Leu Gln Glu Ala Thr
```

```
            2930                2935                2940

Asp Glu Leu Asp Leu Lys Leu Arg Gln Ala Glu Val Ile Lys Gly
            2945                2950                2955

Ser Trp Gln Pro Val Gly Asp Leu Leu Ile Asp Ser Leu Gln Asp
            2960                2965                2970

His Leu Glu Lys Val Lys Ala Leu Arg Gly Glu Ile Ala Pro Leu
            2975                2980                2985

Lys Glu Asn Val Ser His Val Asn Asp Leu Ala Arg Gln Leu Thr
            2990                2995                3000

Thr Leu Gly Ile Gln Leu Ser Pro Tyr Asn Leu Ser Thr Leu Glu
            3005                3010                3015

Asp Leu Asn Thr Arg Trp Lys Leu Leu Gln Val Ala Val Glu Asp
            3020                3025                3030

Arg Val Arg Gln Leu His Glu Ala His Arg Asp Phe Gly Pro Ala
            3035                3040                3045

Ser Gln His Phe Leu Ser Thr Ser Val Gln Gly Pro Trp Glu Arg
            3050                3055                3060

Ala Ile Ser Pro Asn Lys Val Pro Tyr Tyr Ile Asn His Glu Thr
            3065                3070                3075

Gln Thr Thr Cys Trp Asp His Pro Lys Met Thr Glu Leu Tyr Gln
            3080                3085                3090

Ser Leu Ala Asp Leu Asn Asn Val Arg Phe Ser Ala Tyr Arg Thr
            3095                3100                3105

Ala Met Lys Leu Arg Arg Leu Gln Lys Ala Leu Cys Leu Asp Leu
            3110                3115                3120

Leu Ser Leu Ser Ala Ala Cys Asp Ala Leu Asp Gln His Asn Leu
            3125                3130                3135

Lys Gln Asn Asp Gln Pro Met Asp Ile Leu Gln Ile Ile Asn Cys
            3140                3145                3150

Leu Thr Thr Ile Tyr Asp Arg Leu Glu Gln Glu His Asn Asn Leu
            3155                3160                3165

Val Asn Val Pro Leu Cys Val Asp Met Cys Leu Asn Trp Leu Leu
            3170                3175                3180

Asn Val Tyr Asp Thr Gly Arg Thr Gly Arg Ile Arg Val Leu Ser
            3185                3190                3195

Phe Lys Thr Gly Ile Ile Ser Leu Cys Lys Ala His Leu Glu Asp
            3200                3205                3210

Lys Tyr Arg Tyr Leu Phe Lys Gln Val Ala Ser Ser Thr Gly Phe
            3215                3220                3225

Cys Asp Gln Arg Arg Leu Gly Leu Leu Leu His Asp Ser Ile Gln
            3230                3235                3240

Ile Pro Arg Gln Leu Gly Glu Val Ala Ser Phe Gly Gly Ser Asn
            3245                3250                3255

Ile Glu Pro Ser Val Arg Ser Cys Phe Gln Phe Ala Asn Asn Lys
            3260                3265                3270

Pro Glu Ile Glu Ala Ala Leu Phe Leu Asp Trp Met Arg Leu Glu
            3275                3280                3285

Pro Gln Ser Met Val Trp Leu Pro Val Leu His Arg Val Ala Ala
            3290                3295                3300

Ala Glu Thr Ala Lys His Gln Ala Lys Cys Asn Ile Cys Lys Glu
            3305                3310                3315

Cys Pro Ile Ile Gly Phe Arg Tyr Arg Ser Leu Lys His Phe Asn
            3320                3325                3330
```

Tyr Asp Ile Cys Gln Ser Cys Phe Phe Ser Gly Arg Val Ala Lys
3335        3340                3345

Gly His Lys Met His Tyr Pro Met Val Glu Tyr Cys Thr Pro Thr
3350        3355                3360

Thr Ser Gly Glu Asp Val Arg Asp Phe Ala Lys Val Leu Lys Asn
3365        3370                3375

Lys Phe Arg Thr Lys Arg Tyr Phe Ala Lys His Pro Arg Met Gly
3380        3385                3390

Tyr Leu Pro Val Gln Thr Val Leu Glu Gly Asp Asn Met Glu Thr
3395        3400                3405

Pro Val Thr Leu Ile Asn Phe Trp Pro Val Asp Ser Ala Pro Ala
3410        3415                3420

Ser Ser Pro Gln Leu Ser His Asp Asp Thr His Ser Arg Ile Glu
3425        3430                3435

His Tyr Ala Ser Arg Leu Ala Glu Met Glu Asn Ser Asn Gly Ser
3440        3445                3450

Tyr Leu Asn Asp Ser Ile Ser Pro Asn Glu Ser Ile Asp Asp Glu
3455        3460                3465

His Leu Leu Ile Gln His Tyr Cys Gln Ser Leu Asn Gln Asp Ser
3470        3475                3480

Pro Leu Ser Gln Pro Arg Ser Pro Ala Gln Ile Leu Ile Ser Leu
3485        3490                3495

Glu Ser Glu Glu Arg Gly Glu Leu Glu Arg Ile Leu Ala Asp Leu
3500        3505                3510

Glu Glu Glu Asn Arg Asn Leu Gln Ala Glu Tyr Asp Arg Leu Lys
3515        3520                3525

Gln Gln His Glu His Lys Gly Leu Ser Pro Leu Pro Ser Pro Pro
3530        3535                3540

Glu Met Met Pro Thr Ser Pro Gln Ser Pro Arg Asp Ala Glu Leu
3545        3550                3555

Ile Ala Glu Ala Lys Leu Leu Arg Gln His Lys Gly Arg Leu Glu
3560        3565                3570

Ala Arg Met Gln Ile Leu Glu Asp His Asn Lys Gln Leu Glu Ser
3575        3580                3585

Gln Leu His Arg Leu Arg Gln Leu Leu Glu Gln Pro Gln Ala Glu
3590        3595                3600

Ala Lys Val Asn Gly Thr Thr Val Ser Ser Pro Ser Thr Ser Leu
3605        3610                3615

Gln Arg Ser Asp Ser Ser Gln Pro Met Leu Leu Arg Val Val Gly
3620        3625                3630

Ser Gln Thr Ser Asp Ser Met Gly Glu Glu Asp Leu Leu Ser Pro
3635        3640                3645

Pro Gln Asp Thr Ser Thr Gly Leu Glu Glu Val Met Glu Gln Leu
3650        3655                3660

Asn Asn Ser Phe Pro Ser Ser Arg Gly Arg Asn Thr Pro Gly Lys
3665        3670                3675

Pro Met Arg Glu Asp Thr Met
3680        3685